(12) United States Patent
Neya et al.

(10) Patent No.: US 6,207,686 B1
(45) Date of Patent: Mar. 27, 2001

(54) ENDOTHELIN ANTAGONISTS

(75) Inventors: Masahiro Neya, Tsuchiura; Tatsuya Zenkoh, Toride; Hitoshi Sawada, Tsukuba; Chiyoshi Kasahara, Sanda; Masayoshi Murata, Osaka; Keiji Hemmi, deceased, late of Tsukuba; by Mitsue Hemmi, heir, Tsukuba, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 08/836,198

(22) PCT Filed: Nov. 13, 1995

(86) PCT No.: PCT/JP95/02306

§ 371 Date: Jun. 20, 1997

§ 102(e) Date: Jun. 20, 1997

(87) PCT Pub. No.: WO96/15109

PCT Pub. Date: May 23, 1996

(30) Foreign Application Priority Data

Nov. 14, 1994 (GB) .................................... 9422948
May 17, 1995 (GB) .................................... 9509962

(51) Int. Cl.$^7$ .......................... A61K 31/38; A61K 31/40; A61K 31/415; A61K 31/49

(52) U.S. Cl. .......................... 514/338; 514/300; 514/397; 514/414; 514/418; 514/419; 514/443; 514/466; 546/277.4; 548/311.1; 548/453; 548/467; 548/484; 548/485; 548/492; 548/493; 548/496; 548/497; 549/53; 549/58; 549/441

(58) Field of Search ..................................... 514/414, 418, 514/419, 300, 338, 397, 443, 466; 548/467, 484, 485, 492, 493, 496, 497, 311.1, 453; 546/277.4; 549/53, 58, 441

(56) References Cited

PUBLICATIONS

Mock et al. Biochemistry Journal (1994) 302, 57–68.*
Fromsen. J. Med. Chem. (1992) 35, 1246–1259.*

* cited by examiner

Primary Examiner—Peter O'Sullivan
(74) Attorney, Agent, or Firm—Oblon, Spivak, McClelland, Maier & Neustadt, P.C.

(57) ABSTRACT

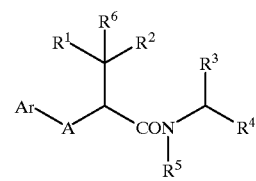

A compound of formula (I), in which: $R^1$ is lower alkyl, cyclo(lower)alkyl, optionally substituted aryl, optionally substituted heterocyclic group, cyclo(lower)alkyl(lower) alkyl, or ar(lower)alkyl; $R^2$ is hydrogen, hydroxy or protected hydroxy; $R^3$ is lower alkyl, aryl, ar(lower)alkyl or optionally substituted heterocyclic(lower)alkyl; $R^4$ is carboxy, protected carboxy or lower alkylsufonylcarbamoyl; $R^5$ is hydrogen or lower alkyl; $R^6$ is hydrogen or heterocyclic group; A is a single bond or lower alkylene, and Ar is optionally substituted aryl, or pharmaceutically acceptable salts thereof, having endothelin antagonistic activity.

11 Claims, No Drawings

ENDOTHELIN ANTAGONISTS

TECHNICAL FIELD

The present invention relates to novel compound and a pharmaceutically acceptable salt thereof.

More particularly, it relates to novel compound and a pharmaceutically acceptable salt thereof which have pharmacological activities such as endothelin (ET) antagonistic activity and the like, to processes for its preparation, to a pharmaceutical composition comprising the same, and to a method of using the same therapeutically in the treatment and the prevention of endothelin mediated diseases such as hypertension, and the like.

Pharmacological and structural evidence supports the existence of at least two endothelin receptor subtypes, i.e., $ET_A$ and $ET_B$. $ET_A$ receptors are distributed predominantly in vascular smooth muscle, heart and intestine, whereas $ET_B$ receptors are found in cerebral cortex, lung and kidney. Recently, it is found that in addition to $ET_A$ receptors, vasoconstrictor $ET_B$ receptors are also present on vascular smooth muscle. $ET_A$ receptors have a higher affinity to ET-1 than ET-3 and sarafotoxin S6c, while $ET_B$ receptors show nearly the same affinity to all isoforms of ET and sarafotoxin peptides.

The compounds of this invention may have $ET_A$ and/or $ET_B$ antagonistic activity.

One object of the present invention is to provide new and useful compound and a pharmaceutically acceptable salt thereof which have pharmacological activities such as endothelin, particularly $ET_A$ and $ET_B$ dual antagonistic activity, and the like.

Another object of the present invention is to provide processes for the preparation of said compound and a salt thereof.

A further object of the present invention is to provide a pharmaceutical composition comprising, as an active ingredient, said compound or a pharmaceutically acceptable salt thereof.

Still further object of the present invention is to provide a method of using the same for the treatment and the prevention of endothelin mediated diseases such as hypertension, and the like.

DISCLOSURE OF INVENTION

The object compound of the present invention can be represented by the following general formula (I).

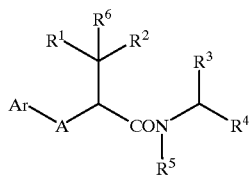
(I)

in which $R^1$ is lower alkyl, cyclo(lower)alkyl, optionally substituted aryl, optionally substituted heterocyclic group, cyclo(lower)alkyl(lower)alkyl, or ar(lower)alkyl, $R^2$ is hydrogen, hydroxy or protected hydroxy, $R^3$ is lower alkyl, aryl, ar(lower)alkyl or optionally substituted heterocyclic(lower)alkyl, $R^4$ is carboxy, protected carboxy or lower alkylsulfonylcarbamoyl, $R^5$ is hydrogen or lower alkyl, $R^6$ is hydrogen or heterocyclic group, A is a single bond or lower alkylene, and Ar is optionally substituted aryl, or pharmaceutically acceptable salts thereof.

The compound having the following formula (IA) is preferable.

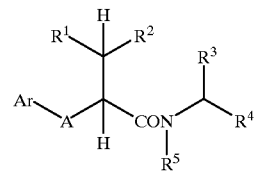
(IA)

Further, the compound having the relative configuration of the following formula (IB) is more preferable.

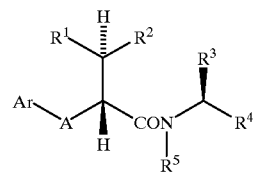
(IB)

in which $R^1$, $R^2$, $R^3$, $R^4$, $R^5$, A and Ar are each as defined above.

According to the present invention, the novel compound (I) and a salt thereof can be prepared by the processes as shown in the following schemes.

Process 1

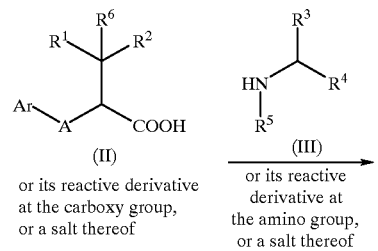

(II)
or its reactive derivative at the carboxy group, or a salt thereof (III)
or its reactive derivative at the amino group, or a salt thereof

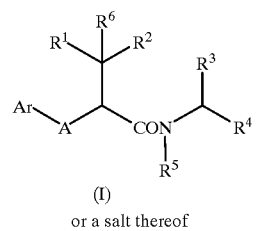
(I)
or a salt thereof

-continued

Process 2

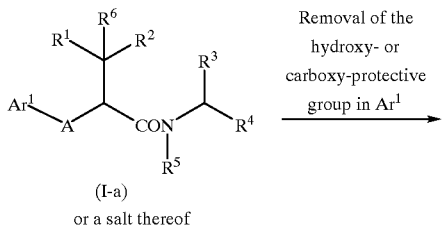

(I-a)
or a salt thereof

Removal of the
hydroxy- or
carboxy-protective
group in Ar¹
→

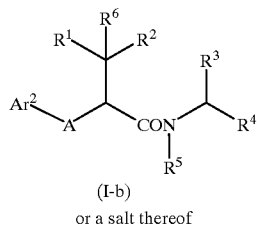

(I-b)
or a salt thereof

Process 3

(I-c)
or a salt thereof

Removal of the
carboxy-protective
group in $R^4_a$
→

(I-d)
or a salt thereof

Process 4

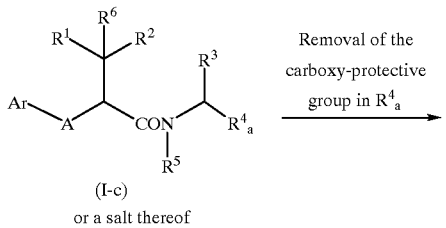

(I-e)
or a salt thereof

Removal of the
imino- and/or
carboxy-protective
group in $R^1_a$
→

(I-f)
or a salt thereof

-continued

Process 5

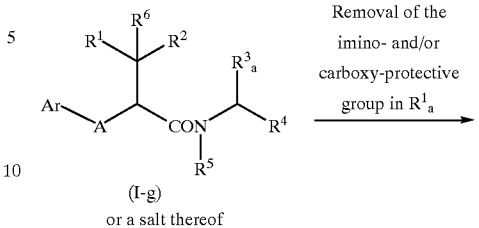

(I-g)
or a salt thereof

Removal of the
imino- and/or
carboxy-protective
group in $R^1_a$
→

(I-h)
or a salt thereof

Process 6

(I-d)
or a salt thereof

Introduction of
a carboxy-
protective group
→

(I-c)
or a salt thereof

Process 7

(I-i)
or a salt thereof

Introduction of
a carboxy-
protective group
into $R^3_c$
→

(I-j)
or a salt thereof

Process 8

(I-k) or a salt thereof
→ Introduction of a hydroxy-protective group →
(I-l) or a salt thereof Process 9

(I-m) or a salt thereof
→ Oxidation of the thia moiety in $R_d^4$ →
(I-n) or a salt thereof wherein $R^1$, $R^2$, $R^3$, $R^4$, $R^5$, $R^6$, A and Ar are each as defined above, $R_a^1$ is aryl substituted at least by protected carboxy; or heterocyclic group containing at least a protected imino moiety and optionally substituted by suitable substituent(s);

$R_b^1$ is aryl substituted at least by carboxy; or heterocyclic group containing at least an imino moiety and optionally substituted by suitable substituent(s);

$R_a^2$ is protected hydroxy, $R_a^3$ is heterocyclic(lower)alkyl substituted at least by protected carboxy(lower)alkyl; or heterocyclic(lower)alkyl containing at least a protected imino moiety and optionally substituted by suitable substituent(s);

$R_b^3$ is heterocyclic(lower)alkyl substituted at least by carboxy(lower)alkyl; or heterocyclic(lower)alkyl containing at least an imino moiety and optionally substituted by suitable substituent(s);

$R_c^3$ is heterocyclic(lower)alkyl substituted at least by carboxy(lower)alkyl, $R_d^3$ is heterocyclic(lower)alkyl substituted at least by protected carboxy(lower)alkyl, $R_e^3$ is heterocyclic(lower)alkyl containing at least a thia moiety and optionally substituted by suitable substituent(s), $R_f^3$ is heterocyclic(lower)alkyl containing at least thia moiety and its dioxide, and optionally substituted by suitable substituent(s), $R_a^4$ is protected carboxy, $Ar^1$ is aryl substituted by the group consisting of protected hydroxy and protected carboxy, and optionally by suitable substituent(s), and $Ar^2$ is aryl substituted by the group consisting of hydroxy and carboxy, and optionally by suitable substituent(s).

Some of the starting compounds used in the above Processes are novel and can be prepared according to the procedures described in the following Preparations and/or by a conventional manner.

Suitable pharmaceutically acceptable salts of the object compound (I) may be a conventional non-toxic salt and include an acid addition salt such as an organic acid salt (e.g. acetate, trifluoroacetate, maleate, tartrate fumarate, methanesulfonate, benzenesulfonate, formate, toluenesulfonate, etc.), an inorganic acid salt (e.g. hydrochloride, hydrobromide, hydriodide, sulfate, nitrate, phosphate, etc.), or a salt with a base such as an amino acid (e.g. arginine, aspartic acid, glutamic acid, etc.), an alkali metal salt (e.g. sodium salt, potassium salt, etc.), an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention includes within the scope thereof are explained in detail as follows.

The term "lower" is intended to mean 1 to 6, preferably 1 to 4 carbon atoms, unless otherwise indicated.

Suitable "cyclo(lower)alkyl" may include cyclo-($C_3$–$C_7$) alkyl such as cyclopropyl, cyclobutyl, cyclopentyl, cyclohexyl, and the like, in which the most preferred example may be cyclopropyl and cyclohexyl.

Suitable "lower alkyl" may include a straight or branched one such as methyl, ethyl, propyl, isopropyl, butyl, isobutyl, tert-butyl, 1-ethylpropyl, pentyl, neopentyl, hexyl, and the like, in which the most preferable one may be ethyl, propyl, isopropyl, butyl, pentyl, 1-ethylpropyl, isobutyl and neopentyl as $R^1$, and isobutyl as $R^3$.

Suitable "protected carboxy" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-)-acetoxybutyl ester, 1-(or 2-)propionyloxyethyl ester, 1-(or 2- or 3-)propionyloxypropyl ester, 1-(or 2-)-butyryloxyethyl ester, 1-(or 2-)isobutyryloxyethyl ester, 1-(or 2-)pyvaloyloxyethyl ester, 1-(or 2-)hexanoyloxyethyl ester isobutyryloxymethyl ester, 2-ethylbutyryloxymethyl ester, 3,3-dimethylbutyryloxymethyl ester, 1-(or 2-)-pentanoyloxyethyl ester, etc.], lower alkanesulfonyl(lower) alkyl ester (e.g. 2-mesylethyl ester, etc.), mono(or di or tri)halo(lower)alkyl ester (e.g. 2-iodoethyl ester, 2,2,2-trichloroethyl ester, etc.); lower alkoxycarbonyloxy(lower)

alkyl ester [e.g. methoxycarbonyloxymethyl ester, ethoxycarbonyloxymethyl ester, propoxycarbonyloxymethyl ester, t-butoxycarbonyloxymethyl ester, 1-(or 2-)-methoxycarbonyloxyethyl ester, 1-(or 2-)-ethoxycarbonyloxyethyl ester, 1-(or 2-)-isopropoxycarbonyloxyethyl ester, etc.], phthalidylidene (lower)alkyl ester, or (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

More preferable example of the protected carboxy thus defined may be lower alkoxycarbonyl and phenyl(or nitrophenyl)($C_1$–$C_4$)alkoxycarbonyl, and the most preferable one may be methoxycarbonyl, ethoxycarbonyl and benzyloxycarbonyl.

Suitable heterocyclic group moiety of "optionally substituted heterocyclic group" or "optionally substituted heterocyclic(lower)alkyl" means saturated or unsaturated, monocyclic or polycyclic heterocyclic group containing at least one hetero-atom such as an oxygen, sulfur, nitrogen atom and the like.

More preferable heterocyclic group may be:
  unsaturated condensed (preferably bicyclic) 7- to 12-membered, preferably 9- or 10-membered, heterocyclic group containing 1 to 5 nitrogen atom(s), for example, indolyl, isoindolyl, indolizinyl, benzimidazolyl, quinolyl, isoquinolyl, indazolyl, benzotriazolyl, tetrazolopyridyl, tetrazolopyridazinyl (e.g., tetrazolo[1,5-b]pyridazinyl, etc.), dihydrotriazolopyridazinyl, etc.;
  unsaturated condensed (preferably bicyclic) 7- to 12-membered, preferably 9- or 10-membered heterocyclic group containing 1 to 3 sulfur atoms or its S,S-dioxide, for example, dithianaphthalenyl (e.g. 4H-1,3-dithianaphthalenyl, 1,4-dithianaphthalenyl, etc.), benzothiophenyl or its S,S-dioxide (e.g. benzo[a]thiophenyl or its S,S-dioxide, benzo[b]thiophenyl or its S,S-dioxide, etc.), etc.,
  unsaturated 3- to 8-membered, preferably 5- or 6-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.;
  saturated 3- to 8-membered, preferably 5- or 6-membered heteromonocyclic group containing 1 to 4 nitrogen atom(s), for example, azetidinyl, pyrrolidinyl, imidazolidinyl, piperidinyl, pyrazolidinyl, piperazinyl, etc.;
  unsaturated condensed (preferably bicyclic) 7- to 12-membered, preferably 9- or 10-membered, heterocyclic group containing 1 to 2 oxygen atom(s) and 1 to 3 nitrogen atom(s), for example, benzoxazolyl, benzoxadiazolyl, etc.;
  unsaturated 3- to 8-membered, preferably 5- or 6-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.), etc.;
  saturated 3- to 8-membered, preferably 5- or 6-membered heteromonocyclic group containing 1 to 2 oxygen atom(s) and 1 to 3 nitrogen atom(s), for example, morpholinyl, etc.;
  unsaturated condensed (preferably bicyclic) 7- to 12-membered, preferably 9- or 10-membered heterocyclic group containing 1 to 2 sulfur atom(s) and 1 to 3 nitrogen atom(s), for example, benzothiazolyl, benzothiadiazolyl, etc.
  unsaturated 3- to 8-membered, preferably 5- or 6-membered heteromonocyclic group containing 1 to 2 sulfur atom(s) and 1 to 3 nitrogen atom(s), for example, thiazolyl, 1,2-thiazolyl, thiazolyl, thiadiazolyl (e.g., 1,2,4-thiadiazolyl, 1,3,4-thiadiazolyl, 1,2,5-thiadiazolyl, 1,2,3-thiadiazolyl), etc.;
  saturated 3- to 8-membered, preferably 5- or 6-membered heteromonocyclic group containing 1 to 2 sulfur atom(s) and 1 to 3 nitrogen atom(s), for example, thiazolidinyl, etc.;
  unsaturated 3- to 8-membered, preferably 5- or 6-membered heteromonocyclic group containing a sulfur atom, for example, thienyl, etc.; and the like;
wherein said heterocyclic group may be substituted by one or more, preferably one or two suitable substituent(s) such as
  hydroxy;
  protected hydroxy, in which the hydroxy group is protected by a conventional hydroxy-protective group such as acyl, ar(lower)alkyl as mentioned below (e.g. benzyl, etc.), tri(lower)alkylsilyl, etc.;
  halogen such as chlorine, bromine, iodine, fluorine, etc.;
  lower alkoxy, which may be straight or branched one such as methoxy, ethoxy, propoxy, isopropoxy, butoxy, pentyloxy, hexyloxy, etc., more preferably $C_1$–$C_4$ alkoxy (e.g. methoxy, etc.);
  carboxy;
  protected carboxy such as lower alkoxycarbonyl (e.g. methoxycarbonyl, t-butoxycarbonyl, etc.), phenyl (or nitrophenyl)(lower)alkoxycarbonyl (e.g. benzyloxycarbonyl, etc.), etc.;
  lower alkylenedioxy, more preferably $C_1$–$C_4$ alkylenedioxy (e.g. methylenedioxy, ethylenedioxy, etc.);
  carbamoyl(lower)alkyl (e.g. carbamoylmethyl, etc.);
  N- or N,N-di(lower)alkylcarbamoyl(lower)alkyl, preferably N,N-di($C_1$–$C_4$)alkylcarbamoyl($C_1$–$C_4$)alkyl (e.g. N,N-dimethylcarbamoylmethyl, etc.);
  carboxy(lower)alkyl, preferably carboxy($C_1$–$C_4$)alkyl (e.g. carboxymethyl, 2-carboxyethyl, etc.);
  protected carboxy(lower)alkyl such as lower alkoxycarbonyl(lower)alkyl (e.g. methoxycarbonylmethyl, 2-ethoxycarbonylethyl, t-butoxycarbonylmethyl, 2-ethoxycarbonylethyl, etc.), ar(lower)alkoxycarbonyl(lower)alkyl (e.g. benzyloxycarbonylmethyl, etc.), etc.;
  $C_6$–$C_{10}$ ar(lower)alkyl such as mono- or di- or triphenyl(lower)alkyl (e.g. triphenylmethyl, etc.);
  halo(lower)alkyl, which is aforementioned lower alkyl group substituted by one or more, preferably one to three halogen as mentioned above;

halo(lower)alkoxy, which is hydroxy group substituted by aforementioned halo(lower)alkyl;

lower alkanoyl as mentioned below (e.g. formyl, etc.); lower alkyl as mentioned above, more preferably $C_1$–$C_4$ alkyl (e.g. methyl, ethyl, isopropyl„ etc.); -amino; -nitro; -cyano; and the like.

And further when said heterocyclic group has imino-moiety(ies) in its ring, the imino-moiety(ies) may be substituted by suitable substituent(s) such as;

-imino-protective group such as acyl, more preferably lower alkanoyl (e.g. formyl, acetyl, etc.) lower alkoxycarbonyl (e.g. t-butoxycarbonyl, etc.), nitroar(lower) alkoxycarbonyl; and the like.

Preferable examples of optionally substituted heterocyclic (lower)alkyl thus defined may be lower alkyl substituted by unsaturated 9- or 10-membered bicyclic heterocyclic group containing 1 to 5 nitrogen atom(s) (e.g. indolyl, etc.) optionally substituted by lower alkanoyl, carbamoyl(lower)alkyl, N- or N,N-di(lower)alkylcarbamoyl(lower)alkyl, hydroxy, $C_6$–$C_{10}$ ar(lower)alkoxy, lower alkoxy, carboxy, lower alkoxycarbonyl(lower)alkyl, carboxy(lower)alkyl, ar(lower) alkoxycarbonyl(lower)alkyl, lower alkoxycarbonyl, phenyl (lower)alkoxycarbonyl, lower alkylenedioxy or lower alkyl; lower alkyl substituted by unsaturated 9- or 10-membered bicyclic heterocyclic group containing 1 to 3 sulfur atoms or its S,S-dioxide (e.g. benzothiophenyl, benzothiophenyl S,S-dioxide, etc.) optionally substituted by lower alkanoyl, carbamoyl(lower)alkanoyl, N- or N,N-di(lower) alkylcarbamoyl(lower)alkyl, hydroxy, $C_6$–$C_{10}$ ar(lower) alkoxy, lower alkoxy, carboxy, lower alkoxycarbonyl(lower) alkyl, carboxy(lower)alkyl, ar(lower)alkoxycarbonyl(lower) alkyl, lower alkoxycarbonyl, phenyl(lower)alkoxycarbonyl, lower alkylenedioxy or lower alkyl; in which the most preferable one may be indol-3-ylmethyl optionally 4-, 5-, 6-, or 7-substituted by methyl or optionally N-substituted by the group consisting of methyl, ethyl, isopropyl, formyl, carbamoylmethyl, N,N-dimethylcarbamoylmethyl, methoxycarbonyl, methoxycarbonylmethyl, ethoxycarbonylmethyl, t-butoxycarbonylmethyl, 2-ethoxycarbonylethyl, benzyloxycarbonylmethyl, carboxymethyl and 2-carboxyethyl, and benzo[b]thiophen-3-ylmethyl or its S,S-dioxide as $R^3$.

Preferable examples of "heterocyclic group" or "optionally substituted heterocyclic group" thus defined may be unsaturated 5- or 6- membered heteromonocyclic group containing 1 to 4 nitrogen atom(s) (e.g. pyridyl, imidazolyl, etc.), optionally substituted by hydroxy, $C_6$–$C_{10}$ ar(lower) alkoxy, lower alkoxy, carboxy, lower alkoxycarbonyl, phenyl(lower)alkoxycarbonyl, triphenyl(lower)alkyl, lower alkylenedioxy or lower alkyl, in which the most preferable one may be pyridin-2-yl, and imidazol-4(or 5)-yl optionally substituted by the group consisting of methyl, ethyl, propyl, butyl, pentyl, triphenylmethyl and t-butoxycarbonyl as $R^1$ and pyridin-2-yl as $R^6$.

Suitable "lower alkylene" means straight or branched one such as methylene, ethylene, trimethylene, methylethylene, and the like, in which more preferable example may be $C_1$–$C_4$ alkylene, and the most preferable one may be methylene and ethylene.

Suitable aryl moiety of "aryl" or "optionally substituted aryl" may include $C_6$–$C_{10}$ aryl such as phenyl, tolyl, xylyl, cumenyl, naphthyl, and the like, wherein said aryl may be substituted by suitable substituent(s) such as those mentioned in the explanation of "optionally substituted heterocyclic group" as mentioned above, and aryl as mentioned above, and the like.

Preferable examples of aryl or optionally substituted aryl thus defined may be phenyl and naphthyl, each of which being optionally substituted by hydroxy, protected hydroxy as mentioned below (e.g. $C_6$–$C_{10}$ ar(lower)alkoxy, etc.), lower alkylenedioxy, carboxy, protected carboxy (e.g. lower alkoxycarbonyl, $C_6$–$C_{10}$ ar(lower)alkoxycarbonyl, etc.), lower alkoxy, aryl, and the like, in which the most preferable one may be phenyl, 3,4-methylenedioxyphenyl, 4-carboxyphenyl, 4-methoxycarbonylphenyl, 3,4,5-trimethoxyphenyl and 4-(or 2-)biphenylyl as $R^1$, phenyl as $R^3$, and 2-hydroxyphenyl, 2-benzyloxyphenyl, 2-methoxyphenyl, 3,4-dimethoxyphenyl, 3,4-methylenedioxyphenyl, 3,4-ethylenedioxyphenyl, 2-(or 4-)carboxyphenyl, 4-methoxycarbonylphenyl, 2-benzyloxycarbonylphenyl and 2-naphthyl as Ar.

Preferable "protected hydroxy" means hydroxy group protected by a conventional hydroxy-protective group such as acyl as mentioned below; ($C_6$–$C_{10}$)ar(lower)alkyl such as mono- or di- or triphenyl(lower)alkyl (e.g. benzyl, benzhydryl, trityl, etc.), etc.; trisubstituted silyl such as tri(lower)alkylsilyl (e.g. trimethylsilyl, triethylsilyl, isopropyldimethylsilyl, t-butyldimethylsilyl, diisopropylmethylsilyl, etc.), tri($C_6$–$C_{10}$)arylsilyl (e.g. triphenylsilyl, etc.), tris[($C_6$–$C_{10}$)ar(lower)alkyl]silyl, for example, tris[phenyl(lower)alkyl]silyl (e.g. tribenzylsilyl, etc.), etc.; and the like, in which more preferable example may be lower alkanoyloxy and $C_6$–$C_{10}$ ar(lower)alkoxy, and the most preferable one may be acetoxy as $R^2$ and benzyloxy in Ar.

Preferable acyl may include aliphatic acyl, aromatic acyl, heterocyclic acyl and aliphatic acyl substituted with aromatic or heterocyclic group(s) derived from carboxylic, carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkylsulfonyl (e.g. mesyl, ethylsulfonyl, propylsulfonyl, isopropylsulfonyl, butylsulfonyl, isobutylsulfonyl, pentylsulfonyl, hexylsulfonyl, etc.), carbamoyl, N-alkylcarbamoyl (e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, t-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cyclohexanecarbonyl, etc.), and the like.

The aromatic acyl may include $C_6$–$C_{10}$ aroyl (e.g. benzoyl, toluoyl, xyloyl, etc.), N-($C_6$–$C_{10}$)arylcarbamoyl (e.g. N-phenylcarbamoyl, N-tolylcarbamoyl, N-naphthylcarbamoyl, etc.), $C_6$–$C_{10}$ arenesulfonyl (e.g. benzenesulfonyl, tosyl, etc.), and the like.

The aliphatic acyl substituted with aromatic group(s) may include aralkoxycarbonyl such as phenyl(lower) alkoxycarbonyl (e.g. benzyloxycarbonyl, phenethyloxycarbonyl, etc.), and the like.

These acyl groups may be further substituted with one or more suitable substituent(s) such as nitro, and the like, and preferable acyl having such substituent(s) may be nitroaralkoxycarbonyl (e.g. nitrobenzyloxycarbonyl, etc.), and the like.

Suitable "cyclo(lower)alkyl(lower)alkyl" means aforementioned lower alkyl which is substituted by $C_3$–$C_7$ cyclo (lower)alkyl such as cyclopropyl, cyclobutyl, cyclopentyl, cyclohexyl, cycloheptyl, and the like, wherein more preferable example may be $C_4$–$C_6$ cyclo(lower)alkyl(lower)alkyl and the most preferable one may be cyclohexylmethyl.

Suitable "ar(lower)alkyl" may include $C_6$-$C_{10}$ ar(lower) alkyl such as phenyl(lower)alkyl (e.g. benzyl, phenethyl, etc.), tolyl(lower)alkyl, xylyl(lower)alkyl, cumenyl(lower) alkyl, naphthyl(lower)alkyl, and the like, in which more preferable example may be phenyl($C_1$-$C_4$)alkyl, and the most preferable one may be benzyl as $R^1$ or $R^3$, 1-(or 2-)-naphthylmethyl as $R^3$.

Suitable "lower alkoxy" means conventional straight or branched one such as methoxy, ethoxy, propoxy, butoxy, t-butoxy, pentyloxy, hexyloxy, and the like, in which the most preferable example may be methoxy.

Suitable "lower alkylsulfonylcarbamoyl" may include carbamoyl substituted by lower alkylsulfonyl such as methyl sulfonyl, etc., in which more preferable example may be $C_1$-$C_4$ alkylsulfonylcarbamoyl, and the most preferable one may be methylsulfonylcarbamoyl.

Preferred embodiment of $R^1$, $R^2$, $R^3$, $R^4$, $R^5$, $R^6$, A and Ar may be:

$R^1$ is cyclo($C_3$-$C_7$)alkyl, $R^2$ is hydroxy, $R^3$ is lower alkyl substituted by unsaturated bicyclic 7- to 12-membered heterocyclic group containing 1 to 5 nitrogen atom(s), optionally N-substituted by lower alkyl (e.g. indol-3-ylmethyl optionally N-substituted by methyl, etc.), $R^4$ is carboxy or $C_6$-$C_{10}$ ar(lower)alkoxycarbonyl, $R^5$ is hydrogen, $R^6$ is hydrogen, A is a single bond or lower alkylene, and Ar is phenyl, hydroxyphenyl, $C_6$-$C_{10}$ ar(lower) alkoxyphenyl, lower alkoxyphenyl, carboxyphenyl or $C_6$-$C_{10}$ ar(lower)alkoxycarbonylphenyl.

Another preferred embodiment of $R^1$, $R^2$, $R^3$, $R^4$, $R^5$, $R^6$, A and Ar may be:

$R^1$ is lower alkyl, cyclo(lower)alkyl, aryl optionally substituted by the group consisting of lower alkylenedioxy, carboxy, lower alkoxycarbonyl, lower alkoxy and aryl, unsaturated 5- or 6-membered heteromonocyclic group containing 1 to 4 nitrogen atom(s) optionally substituted by the group consisting of lower alkyl and lower alkoxycarbonyl, cyclo(lower)alkyl(lower)alkyl, or ar(lower)alkyl, $R^2$ is hydrogen or hydroxy, $R^3$ is lower alkyl, aryl, ar(lower)alkyl, lower alkyl substituted by unsaturated 9- or 10-membered bicyclic heterocyclic group containing 1 to 5 nitrogen atom(s), said heterocyclic group being optionally substituted by lower alkyl, $R^4$ is carboxy, lower alkoxycarbonyl or $C_6$-$C_{10}$ ar(lower)-alkoxycarbonyl, $R^5$ is hydrogen, $R^6$ is hydrogen, A is single bond or lower alkylene, and Ar is aryl optionally substituted by the group consisting of hydroxy, $C_6$-$C_{10}$ ar(lower)alkoxy, lower alkylenedioxy, carboxy, $C_6$-$C_{10}$ ar(lower) alkoxycarbonyl and lower alkoxy.

A further preferred embodiment of $R^1$, $R^2$, $R^3$, $R^4$, $R^5$, $R^6$, A and Ar may be:

$R^1$ is lower alkyl, cyclo(lower)alkyl, aryl optionally substituted by the group consisting of lower alkylenedioxy, carboxy, lower alkoxycarbonyl, lower alkoxy and aryl, unsaturated 5- or 6-membered heteromonocyclic group containing 1 to 4 nitrogen atom(s) optionally substituted by the group consisting of lower alkyl, lower alkoxycarbonyl and triphenyl(lower)alkyl, cyclo (lower)alkyl(lower)alkyl, or ar (lower) alkyl, $R^2$ is hydrogen, hydroxy or protected hydroxy, $R^3$ is lower alkyl, $C_6$-$C_{10}$ aryl, $C_6$-$C_{10}$ ar(lower)alkyl, lower alkyl substituted by the group consisting of unsaturated 9- or 10 membered bicyclic heterocyclic group containing 1 to 5 nitrogen atom(s), said heterocyclic group being optionally 4-, 5-, 6- or 7-substituted by lower alkyl or optionally N-substituted by the group consisting of lower alkyl, carbamoyl(lower)alkyl, N,N-di(lower)alkylcarbamoyl, lower alkoxycarbonyl, carboxy(lower)alkyl, lower alkoxycarbonyl(lower) alkyl and $C_6$-$C_{10}$ ar(lower)alkoxycarbonyl(lower) alkyl, lower alkyl substituted by unsaturated 9- or 10-membered bicyclic heterocyclic group containing 1 to 3 sulfur atom(s) or its S,S-dioxide, $R^4$ is carboxy, lower alkoxycarbonyl, $C_6$-$C_{10}$ ar(lower) alkoxycarbonyl or lower alkylsulfonylcarbamoyl, $R^5$ is hydrogen, $R^6$ is hydrogen or unsaturated 5- or 6-membered heteromonocyclic group containing 1 to 4 nitrogen atom(s), A is a single bond or lower alkylene, and Ar is $C_6$-$C_{10}$ aryl optionally substituted by the group consisting of hydroxy, $C_6$-$C_{10}$ ar(lower)alkoxy, lower alkylenedioxy, carboxy, $C_6$-$C_{10}$ ar(lower) alkoxycarbonyl and lower alkoxy.

The processes for preparing the object compound (I) are explained in detail in the following.

Process 1

The object compound (I) or a salt thereof can be prepared by reacting the compound (II) or its reactive derivative at the carboxy group, or a salt thereof with the compound (III) or its reactive derivative at the amino group, or a salt thereof.

Suitable reactive derivative at the amino group of the compound (III) may include Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as bis(trimethylsilyl)acetamide, mono(trimethylsilyl) acetamide, bis(trimethylsilyl)urea or the like; a derivative formed by reaction of the compound (III) with phosphorus trichloride or phosgene, and the like.

Suitable salts of the compound (III) and its reactive derivative can be referred to the acid addition salts as exemplified for the compound (I).

Suitable reactive derivative at the carboxy group of the compound (II) may include an acid halide, an acid anhydride, an activated amide, an activated ester, and the like. Suitable examples of the reactive derivatives may be an acid chloride; an acid azide; a mixed acid anhydride with acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl

ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like.

These reactive derivatives can optionally be selected from them according to the kind of the compound (II) to be used.

Suitable salts of the compound (II) and its reactive derivative may be a base salt such as an alkali metal salt [e.g. sodium salt, potassium salt, etc.], an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.] or the like.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carboxiimide; N,N'-diethylcarbodiimide, N,N'-diisopropylcarbodiimide; N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; N-hydroxybenzotriazole; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine (e.g. N-methylmorpholine, etc.), N,N-di(lower)alkylbenzylamine, or the like.

The reaction temperature is not critical, and the reaction is usually carried out under cooling to warming.

Process 2

The object compound (I-b) or a salt thereof can be prepared by subjecting the compound (I-a) or a salt thereof to a removal reaction of the hydroxy- or carboxy-protective group in $Ar^1$.

Suitable salts of the compounds (I-a) and (I-b) can be referred to the ones as exemplified for the compound (I).

This reaction is carried out in accordance with a conventional method such as hydrolysis, reduction, or the like.

This hydrolysis is preferably carried out in the presence of a base or an acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, hydrazine, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.].

The reaction is usually carried out in a solvent such as water, an alcohol [e.g. methanol, ethanol, etc.], methylene chloride, chloroform, carbon tetrachloride, tetrahydrofuran, N,N-dimethylformamide, a mixture thereof or any other solvent which does not adversely influence the reaction. A liquid base or acid can be also used as the solvent.

The reaction temperature is not critical and the reaction is usually carried out under cooling to heating.

The reduction method applicable for the removal reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acid to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to heating.

Process 3

The object compound (I-d) or a salt thereof can be prepared by subjecting the compound (I-c) or a salt thereof to a removal reaction of the carboxy-protective group(s) in $R_a^4$.

Suitable salts of the compounds (I-c) and (I-d) can be referred to the ones as exemplified for the compound (I).

This removal reaction can be carried out by a conventional method in this field such as hydrolysis, reduction, and the like, and the details of which can be referred to those of Process 2.

Process 4

The object compound (I-f) or a salt thereof can be prepared by subjecting the compound (I-e) or a salt thereof to a removal reaction of the imino- and/or carboxy-protective group(s) in $R_a^1$.

Suitable salts of the compounds (I-e) and (I-f) can be referred to the ones as exemplified for the compound (I).

This removal reaction can be carried out by a conventional method in this field such as hydrolysis, reduction, and the like, and the details of which can be referred to those of Process 2.

Process 5

The object compound (I-h) or a salt thereof can be prepared by subjecting the compound (I-g) or a salt thereof to a removal reaction of the carboxy-protective group in $R_a^3$.

Suitable salts of the compounds (I-g) and (I-h) can be referred to the ones as exemplified for the compound (I).

This removal reaction can be carried out by a conventional method in this field such as hydrolysis, reduction, and the like, and the details of which can be referred to those of Process 2.

Process 6

The object compound (I-c) or a salt thereof can be prepared by introducing a carboxy-protective group into the compound (I-d) or a salt thereof.

This reaction can be carried out by a conventional method used in this field which can introduce a conventional carboxy-protective group as mentioned above, such as reacting with alcohol or its reactive equivalence (e.g. halide thereof, etc.) in the presence of a suitable base as mentioned above, or by reacting with tri(lower)alkylsilyldiazomethane (e.g. trimethylsilyldiazomethane, etc.) in the presence of a suitable alcohol (e.g. methanol, etc.).

The reduction is usually carried out in a conventional solvent which does not adversely influence the reaction such as benzene, hexane, alcohol (e.g. methanol, ethanol, propanol, etc.), N,N-dimethylformamide, diethyl ether, dioxane, tetrahydrofuran, etc., or a mixture thereof.

The reaction temperature is not critical and the reaction is usually carried out under cooling o heating.

Process 7

The object compound (I-j) or a salt thereof can be prepared by introducing a carboxy-protective group into $R_c^3$ of the compound (I-i) or a salt thereof.

Suitable salts of the compounds (I-i) and (I-j) can be referred to the ones as exemplified for the compound (I).

This removal reaction can be carried out in a similar manner as that of Process 6, therefore the details of which can be referred to those of Process 6.

Process 8

The compound (I-l) or a salt thereof can be prepared by introducing a hydroxy-protective group into the compound (I-k) or a salt thereof.

Suitable salts of the compounds (I-k) and (I-l) may be the same as those for the compound (I).

Suitable introducing agent of the hydroxy-protective group used in this reaction may be a conventional acylating agent which is capable of introducing the acyl group as mentioned before such as carboxylic acid, carbonic acid, sulfonic acid and their reactive derivative, for example, an acid halide, an acid anhydride, an activated amide, an activated ester, and the like.

Preferable example of such reactive derivative may include acid chloride, acid bromide, a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g. methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.), a symmetrical acid anhydride, an activated acid amide with a heterocyclic compound containing imino function such as imidazole, 4-substituted imidazole, dimethylpyrazole, triazole and tetrazole, an activated ester (e.g. p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

This reaction can be carried out in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, 4-dimethylaminopyridine, etc.), quinoline, and the like.

In case that the introducing agent of the hydroxy-protective group is used in a free form or its salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2-methylimidazole), pentamethyleneketene-N-cyclohexylimine, diphenylketene-N-cyclohexylimine, etc.); an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to as so-called "Vilsmeier reagent") formed by the reaction of an amide compound such as N,N-di(lower)alkylformamide (e.g. dimethylformamide, etc.), N-methylformamide or the like with a halogen compound such as thionyl chloride, phosphoryl chloride, phosgene or the like.

The reaction is usually carried out in a conventional solvent which does not adversely influence the reaction such as water, acetone, dichloromethane, alcohol (e.g. methanol, ethanol, etc.), tetrahydrofuran, pyridine, N,N-dimethylformamide, etc., or a mixture thereof, and further in case that the hydroxy-protective group introducing agent is in liquid, it can also be used as a solvent.

The reaction temperature is not critical and the reaction is usually carried out under from cooling to heating.

Process 9

The object compound (I-n) or a salt thereof can be prepared by oxidizing the thia moiety in $R_d^3$ of the compound (I-m) or a salt thereof.

Suitable salts of the compounds (I-m) and (I-n) can be referred to the ones as exemplified for the compound (I).

This reaction can be carried out by a conventional oxidizing method used in this field such as reacting with a suitable oxidizing agent (e.g. m-chloroperbenzoic acid, etc.).

The reduction is usually carried out in a conventional solvent which does not adversely influence the reaction such as benzene, hexane, dichloromethane, N,N-dimethylformamide, diethyl ether, dioxane, tetrahydrofuran, etc., or a mixture thereof.

The reaction temperature is not critical and the reaction is usually carried out under cooling to heating.

The compounds obtained by the above processes can be isolated and purified by a conventional method such as pulverization, recrystallization, column chromatography, reprecipitation, or the like.

The object compound (I) can be transformed into its salt in a conventional manner.

The object compound (I) and intermediate compound (II), and pharmaceutically acceptable salts thereof have pharmacological activities such as endothelin antagonistic activity (Generally, the compound (I) has $ET_A$ and $ET_B$ dual antagonistic activity, and the compound (II) has mainly $ET_A$ antagonistic activity.), for example, relaxating activity of blood vessel, and the like, and useful for therapeutical treatment and prevention of endothelin mediated diseases such as hypertension, heart disease such as angina pectoris, cardiomyopathy, myocardial infarction or the like, cerebral stroke such as cerebral arterial spasm, cerebral ischemia, cerebrovascular twitch or the like, late phase cerebral spasm after subarachnoid hemorrhage, asthma such as bronchoconstruction or the like, renal failure such as acute renal failure, renal insufficiency caused by pharmaceuticals (e.g. Cisplatin, Cyclosporins, etc.), peripheral circulatory failure, such as Raynaud's disease, Buerger's disease, etc., arteriosclerosis, diabetic nephropathy, diabetic retinopathy, shock such as hemorrhagic shock, shock induced by endotoxins, etc., hemangioendothelioma, organopathy after re-perfusion [e.g. after organ and tissue transplantation, percutaneous transluminal coronary angiopathy (PTCA), or percutaneous transluminal coronary recanalization (PTCR), etc.], bloodstream disturbance after an operation, ulcer, irritable bowel syndrome (IBS), dysuria, retinopathy, dysmenorrheal, premature birth such as premature labor, threatened abortion, or the like, glaucoma, re-occlusion after operation of PTCA, and the like.

For therapeutic purpose, the compounds (I) and (II) and pharmaceutically acceptable salts thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral or external (topical) administration.

The pharmaceutical preparations may be capsules, tablets, dragees, granules, solution, suspension, emulsion, sublingual tablet, suppositories, ointment, aerosol, infusion, ophthalmic solutions, vaginal suppository, and the like. If desired, there may be included in these preparations, auxiliary substance, stabilizing agents, wetting or emulsifying agents, buffers and other commonly used additives.

While the dosage of the compounds (I) and (II) will vary depending upon the age and condition of the patient, in the case of intravenous administration, a daily dose of 0.01–100 mg of the active ingredient per kg weight of human being, in the case of intramuscular administration, a daily dose of 0.05–100 mg of the same per kg weight of human being, in case of oral administration, a daily dose of 0.1–100 mg of the same per kg weight of human being is generally given for the treatment of endothelin-mediated diseases.

In order to illustrate the usefulness of the compounds (I) and (II), the pharmacological test data of a representative compound of the compounds (I) and (II) are shown in the following.

Test 1

($ET_B$ Antagonistic Activity)

Radioligand binding assay:

(1) Test Compounds a. Compound A [The compound of Example 12-2)]

b. Compound B [The compound of Example 14-10)]

(2) Test Method (a) Crude receptor membrane preparation:

Membranes as endothelin receptors were isolated from inner medulla of porcine kidney. The inner medulla of porcine kidney was placed in ice-cold buffer (0.25M sucrose, 5 mM Tris-HCl, 0.1 mM EDTA, pH 7.5). The inner medulla was homogenized in five volumes (w/v) of ice-cold buffer using a Brinkman Polytron PT-10 at a setting of 16,000 rpm for three 10-sec periods. The homogenate was centrifuged at 10,000× g for 20 minutes at 4° C. The pellet was discarded and the supernatant was centrifuged at 100, 000× g for 60 minutes at 4° C. The final pellet was resuspended in three volumes of original wet weight of 50 mM Tris-HCl, pH 7.5 buffer (buffer 1) containing 100 MM NaCl, 5 mM $MgCl_2$, 1.5 µg/ml of (p-amidinophenyl) methanesulfonyl fluoride, 120 µg/ml of bacitracin, 12 µg/ml of leupeptin, 6 µg/ml of chymostatin and 10 µg/ml of phosphoramidon for use in the assay.

(b) $^{125}$I-endothelin(ET)-1-binding assay:

To determine [$^{125}$I]ET-1 binding to kidney, membrane suspensions prepared from kidney (10 µg of protein) were incubated by constant shaking for 60 minutes at 23° C. with [$^{125}$I]ET-1 (range, 4–900 pM) in a total volume of 250 µl of buffer 1 that contained 0.1 mg/ml of bovine serum albumin. In this study, a wide range of [$^{125}$I]ET-1 concentrations was used in order to ascertain that [$^{125}$I]ET-1 has a single class of binding sites in each preparation. The incubation, which was performed in duplicate, was terminated by rapid filtration through a Whatman GF/C glass filter disk. The filter disks were washed three times with 0.1 ml of ice-cold 50 mM Tris-HCl buffer (pH 7.5), and the radioactivity was counted in a gamma counter (Hewlett-Packard) with an efficiency of 71%. Nonspecific binding was defined as nondisplaceable binding of 3.2 µMET-1, and specific binding was defined as the difference between total and nonspecific binding. The $K_d$ was determined by Scatchard analysis.

For determination of inhibition curves of test compounds, the membrane suspensions prepared from inner medulla of porcine kidney were incubated with increasing concentrations of test compounds and [$^{125}$I]ET-1 (16 pM). Specific binding represented 85% of total binding with 16 pM [$^{125}$I]ET-1 in porcine kidney. Protein concentration was determined by the dye-binding assay method (Bio-Rad protein assay kit). The $k_i$ for interaction of each compound with the binding sites was calculated from the equation of Williams et al. (J. Biol. Chem. 251, 6915–6923, 1976).

(3) Test Results

The results are shown in Table 1.

TABLE 1

Effect on specific binding of [$^{125}$I]ET-1 in porcine kidney membrane

| Test Compounds | IC$_{50}$ (M) |
| --- | --- |
| Compound A | $7.5 \times 10^{-8}$ |
| Compound B | $<1.0 \times 10^{-8}$ |

Test 2

(ET$_A$ Antagonistic Activity)

Radioligand binding assay:

(1) Test Compounds a. Compound B b. Compound C [The compound of Preparation 11-2)]

(2) Test Method (a) Crude receptor membrane preparation:

Porcine aorta was purchased from Pel-Freez Biologicals (U.S.A.) and stored at −80° C. until use.

Porcine aorta (50 g) was thawed and dissected free from fatty tissue, minced with scissors and then homogenized with a polytron (Brinkmann PT-20, maximal speed for 3×10 sec) in 100 ml buffer (0.25M sucrose, 10 mM Tris-HCl, 0.1 mM EDTA).

The homogenate was centrifuged at 10,000 g for 20 minutes at 4° C.

The supernatant, containing the plasma membrane fraction, was centrifuged at 100,000 g for 60 minutes at 4° C., and then resultant pellets were referred to as crude membrane fractions.

The pellets were resuspended in 25 ml of binding assay buffer (50 mM Tris-HCl, 100 mM NaCl, 5 mM MgCl$_2$, 1.5 μg/ml phenylmethylsulfonyl fluoride (PMSF), 120 μg/ml bacitracin, 12 μg/ml leupepcin, 6 μg/ml chymostain, 0.1% bovine serum albumin (BSA), pH 7.5).

The aorta membrane fractions were stored at −80° C. until use.

(b) $^{125}$I-endothelin-1 binding assay:

$^{125}$I-Endothelin-1 ($1.67 \times 10^{-11}$ M) (Amersham Japan, specific activity: 2000 Ci/m mol) was incubated with 50 μl of aorta membrane preparation in binding assay buffer at room temperature (20–22° C.) for 60 minutes in a final volume of 250 μl.

After incubation, the incubation mixture were filtered through Glass-fiber GF/C filter (pretreated with 0.1% polyethylene imine for 3 hours prior to use) using cell harvester (Brandel M-24S). The filters were then washed ten times with a total of 3 ml of the washing buffer (50 mM Tris-HCl, pH 7.5) at 0° C. The filters were counted in a gamma counter (Packard Auto Gamma Model 5650).

(3) Test Results

The results are shown in Table 2.

TABLE 2

Effect on specific binding of $^{125}$I-endothelin-1 in porcine aorta membrane

| Test Compounds | IC$_{50}$ (M) |
| --- | --- |
| Compound B | $4.0 \times 10^{-8}$ |
| Compound C | $5.3 \times 10^{-7}$ |

From the results of the above-mentioned biological test, it is clear that compound (I) has endothelin antagonistic activity, therefore are useful for the treatment and prevention of endothelin mediated diseases, for example, hypertension, heart disease such as angina pectoris, cardiomyopathy, myocardial infarction of the like, organopathy after reperfusion [e.g. after organ and tissue plantation, myocardial reperfusion injury, PTCA, PTCR, etc.], cerebral stroke such as cerebral arterial spasm, cerebral ischemia, cerebrovascular twitch or the like, late phase cerebral spasm after subarachnoid hemorrhage, asthma such as bronchial asthma, or the like, renal failure such as chronic or acute renal failure renal insufficiency caused by pharmaceutical (e.g. Cisplatin, Cyclosporins, etc.), or the like.

Throughout the present specification, the amino acids, peptides, protective groups, condensing agents, etc. are indicated by the abbreviations according to the IUPAC-IUB (Commission on Biological Nomenclature) which are in common use in a field of the art.

Moreover, other abbreviations used in this specifications are, for example, as follows.

HCl: hydrogen chloride
HPLC: High Performance Liquid Chromatography
HOBT: N-Hydroxybenzotriazole
—OMe: methoxy
WSCD: 1-ethyl-3-(3-dimethylaminopropyl) carbodiimide
Me: methyl
Et: ethyl
$^i$Pr: isopropyl
$^t$Bu: tert-butyl
Bzl: benzyl
TLC: thin layer chromatography The following Preparations and Examples are given for the purpose of illustrating the present invention in detail.

Preparation 1-1)

To a solution of 2-hydroxybenzaldehyde (2.44 g) in toluene (25 ml) was added methoxycarbonylmethylenetriphenylphosphorane (6.68 g) and the mixture was stirred for 3 hours at ambient temperature. The mixture was filtered and the filtrate was concentrated under reduced pressure. The residue was purified by silica gel column chromatography [eluting with ethyl acetate - n-hexane (1:1)] to give methyl 3-(2-hydroxyphenyl)acrylate (2.47 g).

NMR (CDCl$_3$, δ): 3.83 (3H, s), 6.64 (1H, d, J=16.2 Hz), 6.89–6.95 (2H, m), 7.19–7.26 (1H, m), 7.21 (1H, dd, J=7.7 and 1.6 Hz), 8.05 (1H, d, J=16.2 Hz)

Preparation 1-2)

A mixture of methyl 3-(2-hydroxyphenyl)acrylate (2.47 g) and 10% palladium on carbon (0.50 g) in methanol (30 ml) was stirred under hydrogen atmosphere for 3 hours. The mixture was filtered and the filtrate was evaporated under reduced pressure to afford methyl 3-(2-hydroxyphenyl) propionate (2.50 g).

NMR (CDCl$_3$, δ): 1.65 (1H, s), 2.69–2.80 (2H, m), 2.88–3.01 (2H, m), 3.69 (3H, s), 6.82–6.90 (2H, m), 7.07–7.16 (2H, m)

Preparation 1-3)

To an ice-bath cooled suspension of sodium hydride (60% dispersion in mineral oil, 0.40 g) in dimethylformamide (18 ml) were added dropwise methyl 3-(2-hydroxyphenyl) propionate (1.80 g) and benzyl bromide successively. After being stirred for 30 minutes, the mixture was poured into a mixture of diethyl ether (20 ml) and 1N hydrochloric acid solution (90 ml). The organic layer was separated and the aqueous layer was extracted by diethyl ether. The combined organic layer was washed with aqueous sodium bicarbonate solution, dried and concentrated in vacuo. The residue was purified by silica gel column chromatography [eluting with ethyl acetate n-hexane (1:1)] to provide methyl 3-(2-benzyloxyphenyl)-propionate (2.33 g).

NMR (CDCl$_3$, δ): 2.65 (2H, t, J=7.4 Hz), 3.01 (2H, t, J=7.4 Hz), 3.65 (3H, s), 5.10 (2H, s), 6.86–6.93 (2H, m), 7.13–7.20 (2H, m), 7.31–7.45 (5H, m)

Preparation 1-4)

To a cooled (−78° C.) solution of lithium diisopropylamide (1.55M in n-hexane) in tetrahydrofuran (2 ml) was added a solution of 3-(2-benzyloxyphenyl)propionate (140 mg) in tetrahydrofuran (1.4 ml) and the mixture was stirred for 30 minutes. Cyclohexanecarbaldehyde (80 mg) was added. After being stirred for 30 minutes at the same temperature, the mixture was quenched by 1N hydrochloric acid. The organic layer was separated and the aqueous layer was extracted with diethyl ether. The combined organic layer was washed with aqueous sodium bicarbonate solution and brine successively, dried and evaporated under reduced pressure. The residue was purified by preparative thin layer chromatography (silica gel, 60% diethyl ether - hexane) to afford less polar isomer of methyl (2RS,3SR)-2-(2-benzyloxyphenylmethyl)-3-cyclohexyl-3-hydroxypropionate (isomer A) (56.2 mg) and more polar isomer of methyl (2RS,3RS)-2-(2-benzyloxyphenylmethyl)-3-cyclohexyl-3-hydroxypropionate (isomer B) (74.4 mg).

isomer A:

NMR (CDCl$_3$, δ): 0.80–1.80 (10H, m), 2.01 (1 H, d, J=19.9 Hz), 2.87–2.94 (1H, m), 3.03–3.18 (3H, m), 3.44 (3H, s), 3.51–3.55 (1H, m), 5.07 (2H, s), 6.82–7.01 (2H, m), 7.07–7.43 (7H, m)

isomer B:

NMR (CDCl$_3$, δ): 0.88–1.32 (5H, m), 1.55–1.70 (5H, m), 1.87 (1H, d, J=13.2 Hz), 2.90–3.17 (3H, m), 3.29–3.42 (1H, m), 3.53 (3H, s), 5.09 (2H, s), 6.82–6.92 (1H, m), 7.10–7.46 (8H, m)

Preparation 1-5)

(2RS,3RS)-2-(2-Benzyloxyphenylmethyl)-3-cyclohexyl-3-hydroxypropionic acid (711 mg) was obtained in substantially the same manner as that of Preparation 1-6).

NMR (CDCl$_3$, δ): 0.75–1.62 (10H, m), 1.90 (1H, d, J=11.4 Hz), 2.93–3.26 (4H, m), 5.09 (2H, s), 6.86–6.97 (2H, m), 7.13–7.44 (7H, m)

Preparation 1-6)

Methyl (2RS,3SR)-2-(2-benzyloxyphenylmethyl)-3-cyclohexyl-3-hydroxypropionate (1.14 g) was dissolved in a methanolic 1M solution of potassium hydroxide (11 ml) and the mixture was heated under reflux for 4 hours. The solution was concentrated in vacuo and the residue was dissolved in water and washed with diethyl ether. The aqueous layer was acidified by aqueous 1N hydrochloric acid solution and extracted with ethyl acetate. The organic layer was washed with brine, dried and evaporated under reduced pressure to give (2RS,3SR)-2-(2-benzyloxyphenylmethyl)-3-cyclohexyl-3-hydroxypropionic acid (0.998 g).

NMR (CDCl$_3$, δ): 0.92–1.26 (5H, m), 1.26–1.80 (5H, m), 1.90 (1H, d, J=12 Hz), 2.83–3.19 (3H, m), 3.55–3.60 (1), 5.08 (2H, s), 6.82–6.98 (2H, m), 7.14–7.44 (7H, m)

Preparation 2-1)

To a solution of (2-hydroxyphenyl)acetic acid (125 g) in dimethylformamide (1.9 l) was added potassium carbonate (909 g) and benzyl bromide (281 g) successively. After being stirred for 18 hours, the mixture was filtered, and the filtrate was concentrated under reduced pressure. The residue was dissolved in ethyl acetate, washed with 1N aqueous sodium hydroxide solution and brine, dried and evaporated in vacuo. Dichloromethane was added to the residue and the solution was treated with activated carbon. The mixture was filtered and evaporated to give benzyl (2-benzyloxyphenyl) acetate (132 g).

NMR (CDCl$_3$, δ): 3.73 (2H, s), 5.05 (2H, s), 5.09 (2H, s), 6.71–7.39 (14H, m)

Preparation 2-2)

To a suspension of benzyl (2-benzyloxyphenyl)acetate (100 g) in ethanol (500 ml) was added a solution of sodium hydroxide (36 g) in water (300 ml). After being stirred for 16 hours, the mixture was concentrated under reduced pressure. Water was added to the residue and the mixture was washed with diethyl ether. The aqueous layer was acidified by concentrated-hydrochloric acid solution and extracted with ethyl acetate. The organic layer was washed with brine, dried and evaporated in vacuo. The residual oil was crystallized from diisopropyl ether to afford (2-benzyloxyphenyl)acetic acid (28 g).

NMR (CDCl$_3$, δ): 3.71 (2H, s), 5.07 (2H, s), 6.90–7.40 (9H, m)

Process 2-3)

To a solution of (2-benzyloxyphenyl)acetic acid (36 g) in dimethylformamide (360 ml) were added potassium carbonate (61.2 g) and methyl iodide (31.6 g) successively. After being stirred for 17 hours, the mixture was filtered and the filtrate was poured into aqueous 1N hydrochloric acid solution (1.8 l). The separated oil was extracted with diethyl ether and the organic layer was washed with brine, dried and evaporated under reduced pressure. The residue was purified by column chromatography on silica gel [eluting with ethyl acetate - n-hexane (1:1)] to afford methyl (2-benzyloxyphenyl)acetate (23 g).

NMR (CDCl$_3$, δ): 3.63 (3H, s), 3.69 (2H, s), 5.08 (2H, s), 6.90–7.41 (9H, m)

Preparation 2-4)

To a dry ice-acetone bath cooled solution of diisopropylamine (4.84 g) in tetrahydrofuran (100 ml) was added a 1.61M solution of n-butyl lithium in n-hexane (24.8 ml) and the mixture was stirred for 30 minutes at the same temperature. Methyl (2-benzyloxyphenyl)acetate (5.12 g) was added and the mixture was stirred at −70° C. for 30 minutes and allowed to warm to 0° C. Cyclohexanecarbaldehyde (2.24 g) was added and the solution was stirred for 30 minutes. The reaction mixture was quenched by 1N aqueous hydrochloric acid solution (80 ml), washed with aqueous sodium bicarbonate solution and brine, dried, and concentrated in vacuo. The residue was purified by chromatography on silica gel (eluting with 20% diethyl ether in hexane) to afford less polar isomer of methyl (2RS,3SR)-2-(2-benzyloxyphenyl)-3-cyclohexyl-3-hydroxypropionate (isomer A) (394 mg) and more polar isomer of methyl (2RS,3RS)-2-(2-benzyloxyphenyl)-3-cyclohexyl-3-hydroxypropionate (isomer B) (2.67 g).

isomer A:

NMR (CDCl$_3$, δ): 0.9–1.95 (11H, m), 2.46 (1H, d, J=4.3 Hz), 3.63 (3H, s), 3.97–4.05 (1H, m), 4.57 (1H, d, J=5.7 Hz), 5.06 (1H, d, J=11.8 Hz), 5.13 (1H, d, J=11.8 Hz), 6.94–7.01 (2H, m), 7.16–7.53 (7H, m).

isomer B:

NMR (CDCl$_3$, δ): 0.85–1.90 (11H, m), 3.16 (1H, d, J=5.8 Hz), 3.64 (3H, s), 3.93–3.99 (1H, m), 4.32 (1H, d, J=7.9 Hz), 5.05 (1H, d, J=11.8 Hz), 5.10 (1H, d, J=11.8 Hz), 6.90–6.98 (2H, m), 7.19–7.42 (7H, m)

Preparation 2-5)

To a solution of methyl (2RS,3SR)-2-(2-benzyloxyphenyl)-3-cyclohexyl-3-hydroxypropionate (500 mg) in ethanol (10 ml) was added a 1N aqueous solution of sodium hydroxide (5 ml). After being stirred for 24 hours the mixture was concentrated under reduced pressure. The residue was washed with diethyl ether and acidified by 1N aqueous hydrochloric acid solution. The separated oily product was extracted by ethyl acetate. The organic layer was washed with brine, dried and evaporated under reduced pressure to afford (2RS,3SR)-2-(2-benzyloxyphenyl)-3-cyclohexyl-3-hydroxypropionic acid (321 mg).

NMR (CDCl$_3$, δ): 0.90–1.40 (5H, m), 1.40–1.80 (5H, m), 1.80–2.04 (1H, m), 3.99–4.05 (1H, m), 4.46 (1H, d, J=5.4 Hz), 5.06 (1H, d, J=13 Hz), 5.13 (1H, d, J=12 Hz), 6.9–7.01 (2H, m), 7.20–7.56 (7H, m)

Preparation 2-6)

(2RS,3RS)-2-(2-Benzyloxyphenyl)-3-cyclohexyl-3-hydroxypropionic acid (964 mg) was obtained in substantially the same manner as that of Preparation 2-5).

NMR (CDCl$_3$, δ): 0.90–1.40 (5H, m), 1.40–1.85 (6H, m), 3.98 (1H, d, J=6.4 Hz), 4.31 (1H, d, J=7.8 Hz), 5.03 (1H, d, J=11.6 Hz), 5.10 (1H, d, J=11.6 Hz), 6.91–6.98 (2H, m), 7.22–7.40 (7H, m)

Preparation 3-1)

To a solution of methyl (2-benzyloxyphenyl)acetate (935 mg) in tetrahydrofuran (9.4 ml) was added sodium borohydride (600 mg) and the suspension was heated to 45° C. A mixture of methanol (3 ml) and tetrahydrofuran (6 ml) was added dropwise to the mixture and the mixture was stirred for 2 hours. The reaction mixture was concentrated under reduced pressure. The residue was dissolved in dichloromethane and quenched by 1 N aqueous hydrochloric acid solution. The organic layer was washed with brine, dried and evaporated under reduced pressure. The residue was purified by column chromatography on silica gel [eluting with ethyl acetate - n-hexane (1:1)] to afford 2-(2-benzyloxyphenyl)ethanol (764 mg).

IR (Neat): 3350, 1610, 1500, 1460, 1250, 1130, 1050, 1030 cm$^{-1}$

Preparation 3-2)

To an ice-water bath cooled solution of 2-(2-benzyloxyphenyl)ethanol (1.0 g) in dimethyl sulfoxide (11 ml) were added sulfur trioxide pyridine complex (2.47 g) and N,N-diisopropyl-N-ethylamine (2.0 g) successively and the mixture was stirred for 1 hour at ambient temperature. The mixture was poured into water and extracted with diethyl ether. The organic layer was washed with 1N aqueous hydrochloric acid solution and brine, dried, and evaporated under reduced pressure. The residue was dissolved in tetrahydrofuran (10 ml) and to the solution was added methoxycarbonylmethylene triphenylphosphorane (1.47 g). After being stirred for 14 hours, the mixture was concentrated under reduced pressure. The residue was purified by column chromatography on silica gel [eluting with ethyl acetate - n-hexane (1:1)] to afford methyl 4-(2-benzyloxyphenyl)crotonate (0.60 g).

NMR (CDCl$_3$, δ): 3.57 (2H, dd, J=1.5 and 6.7 Hz), 3.71 (3H, s), 5.08 (2H, s), 5.78 (1H, dt, J=15.6 and 1.5 Hz), 6.88–7.43 (10H, m)

Preparation 3-3)

To a mixture of methyl 4-(2-benzyloxyphenyl)crotonate (14.4 g) and nickel chloride hexahydrate (1.19 g) in methanol (200 ml) was added portionwise sodium borohydride (3.78 g). During addition, the reaction temperature was kept at 20° C. by ice cooling. After the addition was completed, the mixture was stirred at ambient temperature for 1 hour and filtered. The filtrate was concentrated under reduced pressure. To the residue, water (100 ml) was added and the solution was extracted with diethyl ether. The organic layer was washed with brine, dried and evaporated in vacuo and the residue was purified by column chromatography on silica gel [eluting with ethyl acetate - n-hexane (1:1)] to give methyl 4-(2-benzyloxyphenyl)butyrate (11.5 g).

NMR (CDCl$_3$, δ): 1.89–2.12 (2H, m), 2.33 (2H, t, J=7.7 Hz), 2.72 (2H, t, J=7.7 Hz), 3.62 (3H, s), 5.08 (2H, s), 6.86–7.45 (9H, m)

Preparation 3-4)

To a dry ice-acetone bath cooled solution of lithium diisopropylamide, prepared from diisopropylamine (222 mg) and 1.61M hexane solution of n-butyllithium (1.24 ml) in tetrahydrofuran (5.6 ml), was added methyl 4-(2-benzyloxyphenyl)butyrate (284 mg) and the mixture was stirred for 30 minutes at the same temperature. Cyclohexanecarbonyl chloride (176 mg) was added. After being stirred for 30 minutes the reaction mixture was quenched by 1N hydrochloric acid solution and the organic layer was separated. The aqueous layer was extracted with ethyl acetate. The combined organic layer was washed with aqueous sodium bicarbonate solution and brine, and dried. The solvent was evaporated in vacuo and the residue was purified by preparative thin layer chromatography [silica gel, ether - n-hexane (1:4)] to afford methyl 4-(2-benzyloxyphenyl)-2-(cyclohexylcarbonyl)butyrate (190 mg).

NMR (CDCl$_3$, δ): 1.05–1.45 (5H, m), 1.57–1.80 (5H, m), 2.08–2.26 (2H, m), 2.26–2.52 (1H, m), 2.68 (2H, t, J=7.2 Hz), 3.61 (1H, t, J=6.5 Hz), 3.64 (3H, s), 5.07 (2H, s), 6.87–7.45 (9H, m)

Preparation 3-5)

To a solution of methyl 4-(2-benzyloxyphenyl)-2-(cyclohexylcarbonyl)butyrate (1.19 g) in methanol (50 ml)

was added calcium chloride (1.11 g) and the mixture was stirred for 30 minutes at ambient temperature. Sodium borohydride (0.20 g) was added dropwise with ice cooling. After being stirred for 15 minutes the mixture was poured into a mixture of ethyl acetate and 1N aqueous hydrochloric acid solution. The aqueous layer was separated and the aqueous solution was extracted with ethyl acetate. The combined organic layer was washed with sodium bicarbonate solution, dried and evaporated in vacuo. The residue was purified by column chromatography on silica gel (eluting with 1–4% diethyl ether in n-hexane) to give less polar isomer of methyl (2RS,3SR)-4-(2-benzyloxyphenyl)-2-[1-cyclohexyl-1-(hydroxy)methyl]-butyrate (isomer A) (1.14 g) and more polar isomer of (2RS,3RS)-isomer of the same (isomer B) (0.10 g).

isomer A:

NMR (CDCl$_3$, δ): 0.80–1.80 (11H, m), 1.91–2.06 (2H, m), 2.30 (1H, d, J=4.2 Hz), 2.55–2.83 (2H, m), 3.49–3.56 (1H, m), 3.63 (3H, s), 5.10 (2H, s), 6.86–7.46 (9H, m)

isomer B:

NMR (CDCl$_3$, δ): 0.80–1.80 (11H, m), 1.80–2.10 (2H, m), 2.45 (1H, d, J=8.7 Hz), 2.60–2.72 (2H, m), 3.36–3.43 (1H, m), 3.64 (3H, s), 5.08 (2H, s), 6.86–7.46 (9H, m)

Preparation 3-6)

To a solution of methyl 4-(2-benzyloxyphenyl)-2-(cyclohexylcarbonyl)butyrate (2.8 g) in methanol (28 ml) was added tetrabutylammonium borohydride (2.2 g) with ice cooling. After being stirred for 1.5 hours at the same temperature, the reaction mixture was quenched by 1N aqueous hydrochloric acid solution, and extracted with ethyl acetate. The organic layer was washed with aqueous sodium bicarbonate solution, dried and evaporated under reduced pressure to afford a mixture of diastereoisomers of methyl (2RS,3RS)- and (2RS,3SR)-4-(2-benzyloxyphenyl)-2-[1-cyclohexyl-1-(hydroxy)methyl]butyrate (2.9 g) ((2RS,3RS):(2RS,3SR)=3.37:1). Purification of the products by column chromatography on silica gel (eluting with ethyl acetate - n-hexane (1:1) provided pure (2RS,3RS)-isomer of the same (712 mg).

(2RS,3RS)-isomer:

NMR (CDCl$_3$, δ): 0.80–1.80 (11H, m), 1.80–2.10 (2H, m), 2.45 (1H, d, J=8.7 Hz), 2.60–2.72 (2H, m), 3.36–3.43 (1H, m), 3.64 (3H, s), 5.08 (2H, s), 6.86–7.46 (9H, m)

Preparation 3-7)

(2RS,3SR)-4-(2-Benzyloxyphenyl)-2-[1-cyclohexyl-1-(hydroxy)methyl]butyric acid (1.05 g) was obtained in substantially the same manner as that of Preparation 2-5).

NMR (CDCl$_3$, δ): 0.80–1.80 (11H, m), 1.80–2.10 (2H, m), 2.61–2.86 (3H, m), 3.55–3.65 (1H, m), 5.07 (2H, s), 6.86–7.45 (9H, m)

Preparation 3-8)

(2RS,3RS)-4-(2-Benzyloxyphenyl)-2-(1-cyclohexyl-1-(hydroxy)methyl]butyric acid (563 mg) was obtained in substantially the same manner as that of Preparation 3-7).

NMR (CDCl$_3$, δ): 0.80–1.82 (11H, m), 1.92–2.08 (2H, m), 2.60–2.78 (3H, m), 3.41–3.47 (1H, m), 5.06 (2H, s), 6.84–7.47 (9H, m)

Preparation 4-1)

Methyl-3-(2-methoxyphenyl)propionate (5.01 g) was obtained from methyl 3-(2-hydroxyphenyl)propionate (4.95 g) and methyl iodide (3.9 g) in substantially the same manner as that of Preparation 2-1).

NMR (CDCl$_3$, δ): 2.61 (2H, q, J=7.4 and 11.2 Hz), 2.93 (2H, q, J=7.4 and 11.2 Hz), 3.66 (3H, s), 3.82 (3H, s), 6.82–6.91 (2H, m), 7.12–7.25 (2H, m)

Preparation 4-2)

Methyl 3-(2-methoxyphenyl)propionate (1.80 g) was reacted with cyclohexane carbaldehyde (1.25 g) in substantially the same manner as that of Preparation 1-4) to give less polar isomer of methyl (2RS,3SR)-3-cyclohexyl-3-hydroxy-2-(2-methoxyphenylmethyl)propionate (isomer A) (0.706 g) and more polar isomer of (2RS,3RS)-isomer of the same (isomer B) (0.940 g).

isomer A:

NMR (CDCl$_3$, δ): 0.95–1.78 (10 H, m), 2.04 (1H, d, J=12.7 Hz), 2.64–3.14 (4H, m), 3.51 (3H, s), 3.57–3.61 (1H, m), 3.87 (3H, s), 6.81–6.88 (2H, m), 7.05–7.23 (2H, m)

isomer B:

NMR (CDCl$_3$, δ): 0.95–1.82 (10H, m), 1.96 (1H, d, J=13.4 Hz), 2.66 (1H, d, J=9.0 Hz), 2.93–3.01 (3H, m), 3.20–3.38 (1H, m), 3.57 (3H, s), 3.94 (3H, s), 6.82–6.90 (2H, m), 7.08–7.25 (2H, m)

Preparation 4-3)

(2RS,3SR)-3-Cyclohexyl-3-hydroxy-2-(2-methoxyphenyl-methyl)propionic acid (340 mg) was obtained in substantially the same manner as that of Preparation 1-6).

NMR (CDCl$_3$, δ): 0.85–1.40 (5H, m), 1.40–1.85 (5H, m), 2.03 (1H, d, J=12.4 Hz), 2.83–3.10 (3H, m), 3.64 (1H, dd, J=3.3 and 7.4 Hz), 3.79 (3H, s), 6.81–6.89 (2H, m), 7.12–7.25 (2H, m)

Preparation 5-1)

To a suspension of (t-butoxycarbonylmethyl)-triphenylphosphonium chloride (20.7 g) in tetrahydrofuran (200 ml) was added potassium t-butoxide (5.60 g) portion-wise and the mixture was stirred for 30 minutes at ambient temperature. 2-Carboxybenzaldehyde was added to the mixture. After being stirred for 1 hour the reaction mixture was filtered and the filtrate was evaporated under reduced pressure. The residue was dissolved in 1N aqueous sodium hydroxide solution and washed with ethyl acetate. The aqueous layer was acidified by conc. hydrochloric acid solution and extracted with ethyl acetate. The organic layer was washed with brine, dried and concentrated under reduced pressure to afford t-butyl 3-(2-carboxyphenyl) acrylate (8.3 g).

NMR (CDCl$_3$, δ): 1.55 (9H, s), 6.27 (1H, d, J=15.9 Hz), 7.26–7.65 (3H, m), 8.09 (1H, dd, J=0.8 and 7.5 Hz), 8.47 (1H, d, J=15.9 Hz)

Preparation 5-2)

t-Butyl 3-(2-carboxyphenyl)propionate was obtained in substantially the same manner as that of Preparation 1-2).

NMR (CDCl$_3$, δ): 1.42 (9H, s), 2.58–2.83 (2H, m), 3.24–3.50 (2H, m), 7.26–7.53 (3H, m), 8.04–8.11 (1H, m)

Preparation 5-3)

A diastereisomeric mixture of t-butyl 2-(2-carboxyphenylmethyl)-3-cyclohexyl-3-hydroxypropionate (1.4 g) was obtained in substantially the same manner as that of Preparation 1-4).

NMR (CDCl$_3$, δ): 0.80–1.50 (5H, m), 1.21 (4.5H, s), 1.29 (4.5H, s), 1.35–1.85 (5H, m), 1.85–2.10 (1H, m), 3.01–3.70 (4H, m), 7.25–7.49 (3H, m), 8.06 (1H, d, J=7.5 Hz)

Preparation 5-4

To a solution of t-butyl 2-(2-carboxyphenylmethyl)-3-cyclohexyl-3-hydroxypropionate (200 mg) in dimethylformamide (2 ml) were added benzyl bromide (100 mg) and potassium carbonate (270 mg) successively. After being stirred for 30 minutes the mixture was filtered and the filtrate was evaporated under reduced pressure. The residue was purified by preparative thin layer chromatography [silica gel, ethyl acetate - n-hexane (1:1)] to afford t-butyl 2-(2-benzyloxycarbonylphenylmethyl)-3-cyclohexyl-3-hydroxypropionate (108 mg).

NMR (CDCl$_3$, δ): 0.80–1.25 (5H, m), 1.20 (4.5H, s), 1.25 (4.5H, s), 1.50–1.80 (5H, m), 1.80–2.07 (1H, m), 2.81–3.75 (4H, m), 5.28–5.41 (2H, m), 7.22–7.46 (8H, m), 7.96 (1H, d, J=7.3 Hz)

Preparation 5-5 t-Butyl 2-(2-benzyloxycarbonylphenylmethyl)-3-cyclohexyl-3-hydroxypropionate (100 mg) was dissolved in a solution of 10% trifluoroacetic acid in dichloromethane (1 ml) and the mixture was stirred for 5 hours. The solution was evaporated under reduced pressure and the residue was purified by chromatography [eluting with methanol-dichloromethane (1:19)] to give 2-(2-benzyloxycarbonyl-phenylmethyl)-3-cyclohexyl-3-hydroxypropionic acid (35 mg).

NMR (CDCl$_3$, δ): 0.75–2.10 (11H, m), 2.95–3.30 (2H, m), 3.47–3.66 (1H, m), 5.32 and 5.35 (2H, each s), 7.26–7.42 (8H, m), 7.92 (1H, d, J=7.7 Hz)

Preparation 6-1

To a solution of (2RS,3RS)-2-(2-benzyloxyphenyl)-3-cyclohexyl-3-hydroxypropionic acid (354 mg) in dichloromethane (7 ml) was added hydroquinine (326 mg) and the mixture was stirred to be a clear solution. The solvent was evaporated under reduced pressure and the residue was crystallized from ethyl acetate. Precipitates were recrystallized from a mixture of ethyl acetate and ethanol (50:1) to afford hydroquinine salt of (2S,3S)-2-(2-benzyloxyphenyl)-3-cyclohexyl-3-hydroxypropionic acid as crystals (150 mg).

NMR (CDCl$_3$, δ): 0.75 (3H, t, J=7.0 Hz), 0.90–1.30 10H, m), 1.45–1.80 (8H, m), 1.80–2.05 (3H, m), 2.45–2.60 (1H, m), 2.70–2.90 (1H, m), 3.10–3.30 (2H, m), 3.52 (3H, s), 3.83–3.87 (1H, m), 4.00–4.20 (2H, m), 4.82 (1H, d, J=11.7 Hz), 4.96 (1H, d, J=11.7 Hz), 6.03 (1H, s), 6.80–6.89 (2H, m), 7.08–7.49 (9H, m), 7.86 (1H, d, J=9.2 Hz), 8.62 (1H, d, J=4.5 Hz)

$[α]_D^{21}$: –46.6° (C=1.0, CH$_2$Cl$_2$)

Mother liquid of the recrystallization was evaporated under reduced pressure to give hydroquinine salt of (2R,3R)-isomer of the same as a main component in an oily form.

NMR (CDCl$_3$, δ): 0.75 (3H, t, J=7.0 Hz), 0.95–1.30 (10H, m), 1.45–1.80 (8H, m), 1.80–2.10 (3H, m), 2.45–2.60 (1H, m), 2.85–2.95 (1H, m), 3.10–3.20 (1H, m), 3.34 (3H, s), 3.65–3.70 (1H, m), 4.83–5.09 (2H, m), 6.05 (1H, s), 6.67 (1H, d, J=2.5 Hz), 6.82–7.48 (10H, m), 7.75 (1H, d, J=9.2 Hz), 8.52 (1H, d, J=4.5 Hz)

$[α]_D^{21}$: –17.6° (C=1.0, CH$_2$Cl$_2$)

Preparation 6-2

The hydroquinine salt of (2S,3S)-2-(2-benzyloxyphenyl)-3-cyclohexyl-3-hydroxypropionic acid (40 mg) was suspended in ethyl acetate and washed with 1N aqueous hydrochloric acid solution. The organic layer was washed with brine, dried and evaporated under reduced pressure to give (2S,3S)-2-(2-benzyloxyphenylmethyl)-2-carboxy-2-hydroxypropionic acid (21 mg).

$[α]_D^{21}$: –64.3° (C=1.2, CH$_2$Cl$_2$)

The hydroquinine salt of (2R,3R)-2-(2-benzyloxyphenylmethyl)-3-cyclohexyl-3-hydroxypropionic acid (40 mg) obtained in Preparation 6-1 was dissolved in ethyl acetate. The solution was washed with 1N aqueous hydrochloric acid solution and brine, dried, and evaporated in vacuo to afford a product which contains (2R,3R)-2-(2-benzyloxyphenylmethyl)-3-cyclohexyl-3-hydroxypropionic acid as a main isomer (20 mg).

$[α]_D^{21}$: 22.2° (C=1.0, CH$_2$Cl$_2$)

Preparation 7

To a dry ice-acetone bath cooled 1.45M solution of lithium diisopropylamide in a mixture of tetrahydrofuran and n-hexane (1.4 ml) was added methyl (2-benzyloxyphenyl)acetate (256 mg). The mixture was stirred for 30 minutes at the same temperature and then for 30 minutes at 0° C. After cooling the solution to –78° C. chlorotrimethylsilane (0.3 ml) was added and the mixture was allowed to warm to room temperature. The solution was diluted with n-hexane (50 ml), filtered through celite, and concentrated under reduced pressure to afford 2-(2-benzyloxyphenyl)-1-methoxy-1-trimethylsilyloxyethylene. To an ice bath cooled solution of (2S)-3-methyl-2-(p-tolylsulfonylamino)butanol (288 mg) in dichloromethane (10 ml) was added a 1M solution of borane-tetrahydrofuran complex in tetrahydrofuran (1.0 ml) and the mixture was stirred for 30 minutes at ambient temperature. After cooling the solution to –78° C., cyclohexanecarbaldehyde (112 mg) and a solution of 2-(2-benzyloxyphenyl)-1-methoxy-1-trimethylsilyloxyethylene prepared above in dichloromethane (1 ml) were added. The solution was stirred for one hour at –78° C. and then quenched by an aqueous solution of sodium bicarbonate at 0° C. The mixture was extracted with diethyl ether, dried and evaporated in vacuo. The residue was dissolved in a mixture of tetrahydrofuran (4 ml) and aqueous 1M solution of hydrochloric acid (2 ml), and the resulting solution was allowed to stand for 30 minutes. Aqueous solution of sodium bicarbonate was added thereto and the mixture was extracted with ether. The organic layer was dried and evaporated. Preparative thin layer chromatography [silica gel, ether - hexane (1:4)] afforded methyl (2R,3R)-2-(2-benzyloxyphenyl)-3-cyclohexyl-3-hydroxypropionate (187 mg). High pressure liquid chromatography analysis (Daicel AD column eluting with 20% isopropyl alcohol - hexane) indicated an enantiomeric excess of 95% (Rt: major 10.51 minutes, minor 8.60 minutes).

NMR (CDCl$_3$, δ): 0.85–1.90 (11H, m), 3.16 (1H, d, J=5.8 Hz), 3.64 (3H, s), 3.93–3.99 (1H, m), 4.32 (1H, d, J=7.9 Hz), 5.05 (1H, d, J=11.8 Hz), 5.10 (1H, d, J=11.8 Hz), 6.90–6.98 (2H, m), 7.19–7.42 (7H, m)

Preparation 8-1

To a solution of 3,4-methylenedioxyphenylacetic acid (10 g) in ethanol (100 ml) was added conc. sulfuric acid (3 ml). After being refluxed for 90 minutes, the mixture was concentrated in vacuo. The residue was dissolved in diethyl ether (150 ml). The solution was washed with 1M aqueous sodium bicarbonate solution and brine successively and dried over magnesium sulfate, and concentrated in vacuo to give ethyl 3,4-methylenedioxyphenylacetate (11.0 g) as an oil.

NMR (CDCl$_3$, δ): 1.25 (3H, t, J=7 Hz), 3.52 (2H, s), 4.15 (2H, q, J=7 Hz), 5.94 (2H, s), 6.70–6.82 (3H, m)

Preparation 8-2)

To a solution of N,N-diisopropyl-N-ethylamine (4.49 g) in tetrahydrofuran (50 ml) was added with stirring 1.6M n-butyl lithium in n-hexane solution (27.6 ml) below 0° C. under a nitrogen atmosphere. After the mixture was stirred in an ice-bath for 30 minutes, a solution of ethyl 3,4-methylenedioxyphenylacetate (3.85 g) in tetrahydrofuran (40 ml) was added at −78° C. The mixture was stirred for 30 minutes and cyclohexanecarbaldehyde (2.49 g) was added. After being stirred for 15 minutes at the same temperature, the mixture was quenched by saturated aqueous ammonium acetate. The mixture was extracted with diethyl ether (100 ml), and the solution was washed with 1M hydrochloric acid and brine successively, dried over magnesium sulfate and concentrated in vacuo. The residue was purified by silica gel column chromatography (eluent; n-hexane:ethyl acetate= 6:1) to give ethyl (2RS,3RS)-2-(3,4-methylenedioxyphenyl)-3-cyclohexyl-3-hydroxypropionate (4.45 g) as an oil.

NMR (CDCl$_3$, δ): 0.92–1.80 (14H, m), 2.55 (1H, d, J=6.5 Hz), 3.62–3.70 (1H, m), 3.85–3.95 (1H, m), 4.02–4.22 (2H, m), 5.94 (1H, s), 6.75 (2H, s), 6.80 (1H, s)

FAB MS m/z: 321 [M+H]$^+$

Preparation 8-3)

To a solution of ethyl (2RS,3RS)-2-(3,4-methylenedioxyphenyl)-3-cyclohexyl-3-hydroxypropionate (4.2 g) in ethanol (50 ml) was added 1M sodium hydroxide solution (26.2 ml) at room temperature. After being stirred for 1.5 hours at the same temperature, the mixture was concentrated in vacuo. The residue was dissolved in 1N hydrochloric acid (50 ml) and ethyl acetate (100 ml) and the organic layer was washed with brine, dried over magnesium sulfate, and concentrated in vacuo. The residue was crystallized from n-hexane to give (2RS,3RS)-2-(3,4-methylenedioxyphenyl)-3-cyclohexyl-3-hydroxypropionic acid (1.43 g).

mp: 162–163° C.

NMR (CDCl$_3$, δ): 0.96–1.76 (11H, m), 3.72 (1H, d, J=8 Hz), 3.94 (1H, d, J=8 Hz), 5.93 (1H, s), 6.75 (2H, s), 6.82 (1H, s)

FAB MS m/z: 293 [M+H]$^+$

Preparation 9

Ethyl (2-methoxyphenyl)acetic acid (11.1 g) was obtained in substantially the same manner as that of Preparation 8-1).

This product was immediately used for the next step.

Preparation 9-2)

Ethyl (2RS,3RS)-2-(2-methoxyphenyl)-3-cyclohexyl-3-hydroxypropionate (2.56 g) was obtained in substantially the same manner as that of Preparation 8-2).

NMR (CDCl$_3$, δ): 0.96–1.41 (6H, m), 1.18 (3H, t, J=8 Hz), 1.48–1.90 (5H, m), 3.20 (1H, d, J=7 Hz), 3.82 (3H, s), 3.86–3.95 (1H, m), 4.10–4.20 (2H, m), 4.22 (1H, d, J=8 Hz), 6.88 (1H, d, J=8 Hz), 9.64 (1H, d, J=8 Hz), 7.20–7.32 (2H, m)

FAB MS m/z: 307 [M+H]$^+$

Preparation 9-3)

(2RS,3RS)-2-(2-Methoxyphenyl)-3-cyclohexyl-3-hydroxypropionic acid (1.34 g) was obtained in substantially the same manner as that of Preparation 8-3).

mp: 99–101° C.

NMR (CDCl$_3$, δ): 0.98–1.38 (6H, m), 1.48–1.85 (5H, m), 3.82 (1H, s), 3.94 (1H, m), 4.28 (1H, d, J=7 Hz), 7.86–7.96 (2H, m), 7.18–7.30 (2H, m)

FAB MS m/z: 279 [M+H]$^+$

The following compounds were obtained in substantially the same manner as that of Preparation 8-2).

Preparation 10-1)

Ethyl (2RS,3RS)-2-(3,4-methylenedioxyphenyl)-3-hydroxyheptanoate (370 mg)

NMR (CDCl$_3$, δ): 0.84 (3H, t, J=7 Hz), 1.21 (3H, t, J=7 Hz), 1.20–1.55 (6H, m), 2.70 (1H, d, J=6.5 Hz), 3.45 (1H, d, J=8 Hz), 4.00–4.25 (3H, m), 5.95 (2H, s), 6.70–6.82 (3H, m)

FAB MS m/z: 295 [M+H]$^+$

Preparation 10-2)

Ethyl (2RS,3RS)-2-(3,4-methylenedioxyphenyl)-3-hydroxyhexanoate (350 mg)

NMR (CDCl$_3$, δ): 0.84 (3H, t, J=8 Hz), 1.22 (3H, t, J=7 Hz), 1.24–1.60 (4H, m), 3.45 (1H, d, J=8 Hz), 4.02–4.22 (3H, m), 5.95 (2H, s), 6.70–6.80 (3H, m)

FAB MS m/z: 281 [M+H]$^+$

Preparation 10-3)

Ethyl (2RS,3RS)-2-(3,4-methylenedioxyphenyl)-3-hydroxyoctanoate (415 mg)

NMR (CDCl$_3$, δ): 0.84 (3H, t, J=8 Hz), 1.14–1.55 (8H, m), 2.70 (1H, d, J=7 Hz), 3.45 (1H, d, J=8 Hz), 4.02–4.28 (3H, m), 5.95 (2H, s), 6.70–6.82 (3H, m)

FAB MS m/z: 309 [M+H]$^+$

Preparation 10-4)

Ethyl (2RS,3RS)-2-(3,4-methylenedioxyphenyl)-3-hydroxy-4-ethylhexanoate (677 mg)

NMR (CDCl$_3$, δ): 0.80–1.02 (7H, m), 1.15–1.60 (7H, m), 2.45 (1H, d, J=7 Hz), 3.70 (1H, d, J=8 Hz), 4.05–4.28 (3H, m), 5.95 (2H, s), 6.70–6.85 (3H, m)

FAB MS m/z: 309 [M+H]$^+$

Preparation 10-5)

Ethyl (2RS,3RS)-2-(3,4-methylenedioxyphenyl)-3-hydroxy-5-methylhexanoate (339 mg)

NMR (CDCl$_3$, δ): 0.88–0.90 (6H, m), 0.90–1.06 (1H, m), 1.18–1.37 (4H, m), 1.76–1.90 (1H, m), 2.64 (1H, d, J=6 Hz), 3.40 (1H, d, J=8 Hz), 4.02–4.22 (3H, m), 5.95 (2H, s), 6.68–6.80 (3H, m)

FAB MS m/z: 295 [M+H]$^+$

Preparation 10-6)

Ethyl (2RS,3RS)-2-(3,4-methylenedioxyphenyl)-3-hydroxy-4-cyclohexylbutyrate (352 mg)

NMR (CDCl$_3$, δ): 0.60–1.80 (16H, m), 2.64 (1H, d, J=6 Hz), 3.40 (1H, d, J=8 Hz), 4.05–4.25 (3H, m), 5.94 (2H, s), 6.65–6.80 (3H, m)

FAB MS m/z: 335 [M+H]$^+$

Preparation 10-7)

Ethyl (2RS,3RS)-2-(3,4-methylenedioxyphenyl)-3-hydroxyvalerate (555 mg)

NMR (CDCl₃, δ): 0.92 (3H, t, J=7 Hz), 1.22 (3H, t, J=8 Hz), 1.25–1.50 (2H, m), 2.19 (1H, d, J=6 Hz), 3.48 (1H, d, J=8 Hz), 3.95–4.25 (3H, m), 5.95 (2H, s), 6.70–6.80 (3H, m)

FAB MS m/z: 267 [M+H]⁺

Preparation 10-8)

Ethyl (2RS,3RS)-2-(3,4-methylenedioxyphenyl)-3-hydroxy-5,5-dimethylhexanoate (930 mg)

NMR (CDCl₃, δ): 0.87 (9H, s), 1.21 (3H, t, J=7 Hz), 1.20–1.33 (2H, m), 2.57 (1H, d, J=7 Hz), 3.40 (1H, d, J=8 Hz), 4.02–4.25 (3H, m), 5.95 (2H, s), 6.70–6.80 (3H, m)

FAB MS m/z: 309 [M+H]⁺

Preparation 10-9)

Ethyl (2RS,3RS)- and (2RS,3SR)-3-hydroxy-4-methyl-2-(3,4-methylenedioxyphenyl)valerate was obtained in substantially the same manner as that of Preparation 8-2).

The stereoisomers were separated by silica gel column chromatography (30 g)(eluent; n-hexane:ethyl acetate=9:1) to give more polar isomer (1.02 g) and less polar isomer (330 mg). The stereostructures of the more polar and the less polar isomers were assigned as (2RS,3RS)- and (2RS,3SR)-configurations respectively.

More polar isomer:

NMR (CDCl₃, δ): 0.87 (3H, d, J=8 Hz), 0.96 (3H, d, J=8 Hz), 1.22 (3H, t, J=8 Hz), 1.44–1.53 (1H, m), 2.50 (1H, d, J=7 Hz), 3.61 (1H, d, J=10 Hz), 3.93–4.00 (1H, m), 4.06–4.22 (2H, m), 5.95 (2H, s), 6.76 (2H, s), 6.82 (1H, s)

Less polar isomer:

NMR (CDCl₃, δ): 0.98 (3H, d, J=4 Hz), 1.00 (3H, d, J=4 Hz), 1.02 (3H, t, J=8 Hz), 1.59–1.70 (1H, m), 2.26 (1H, d, J=4 Hz), 3.62 (1H, d, J=8 Hz), 3.87–3.94 (1H, m), 4.06–4.21 (2H, m), 5.95 (2H, s), 6.77 (1H, d, J=9 Hz), 6.85 (1H, d, J=9 Hz), 6.99 (1H, s)

The following compounds were obtained in substantially the same manner as that of Preparation 8-2).

Preparation 10-10)

Benzyl 3-hydroxy-2-(3,4-methylenedioxyphenyl)-3-phenylpropionate (1.16 g)

NMR (CDCl₃, δ): 2.40 (0.3H, d, J=1 Hz), 2.99 (0.7H, d, J=3 Hz), 3.82–3.86 (1H, m), 4.84–5.26 (3H, m), 5.88–5.95 (2H, m), 6.48–7.03 (3H, m), 7.10–7.34 (10H, m)

Preparation 10-11)

Benzyl 3-hydroxy-2-(3,4-methylenedioxybenzyl)-3-phenylpropionate (2.88 g)

NMR (CDCl₃, δ): 2.65–3.10 (4H, m), 4.81–5.05 (3H, m), 5.89, 5.90 (total 2H, s), 6.49–6.68 (3H, m), 6.96–7.06 (2H, m), 7.25–7.39 (8H, m)

Preparation 10-12)

Ethyl (2RS)-2-(3,4-methylenedioxyphenyl)-3-phenylpropionate

NMR (CDCl₃, δ): 1.13 (3H, t, J=8 Hz), 2.98 (1H, dd, J=7, 14 Hz), 3.34 (1H, dd, J=9, 14 Hz), 3.74 (1H, dd, J=7, 9 Hz), 4.00–4.12 (2H, m), 5.95 (2H, s), 6.74 (2H, s), 6.88 (1H, s), 7.10–7.17 (2H, m), 7.18–7.28 (3H, m)

FAB MS: 298.3 [M]⁺

The following compounds were obtained in substantially the same manner as that of Preparation 8-3).

Preparation 11-1)

(2RS,3RS)-2-(3,4-Methylenedioxyphenyl)-3-hydroxyheptanoic acid (300 mg)

mp: 107–108° C.

NMR (CDCl₃, δ): 0.84 (3H, t, J=8 Hz), 1.16–1.55 (6H, m), 3.50 (1H, d, J=8 Hz), 4.10 (1H, m), 5.95 (2H, s), 6.70–6.85 (3H, m)

FAB MS m/z: 267 [M+H]⁺

Preparation 11-2)

(2RS,3RS)-2-(3,4-Methylenedioxyphenyl)-3-hydroxyhexanoic acid (174 mg)

mp: 138–139° C.

NMR (CDCl₃, δ): 0.85 (3H, t, J=8 Hz), 1.29 (3H, m), 1.42–1.60 (1H, m), 3.50 (1H, d, J=8 Hz), 4.05–4.20 (1H, m), 5.96 (2H, s), 6.70–6.88 (3H, m)

FAB MS m/z: 253 [M+H]⁺

Preparation 11-3)

(2RS,3RS)-2-(3,4-Methylenedioxyphenyl)-3-hydroxyoctanoic acid (300 mg)

mp: 121–122° C.

NMR (CDCl₃, δ): 0.84 (3H, t, J=8 Hz), 1.10–1.55 (8H, m), 3.50 (1H, d, J=8 Hz), 4.05–4.15 (1H, m), 5.96 (2H, s), 6.70–6.85 (3H, m)

FAB MS m/z: 281 [M+H]⁺

Preparation 11-4)

(2RS,3RS)-2-(3,4-Methylenedioxyphenyl)-3-hydroxy-4-ethylhexanoic acid (330 mg)

mp: 155–156° C.

NMR (CDCl₃, δ): 0.82 (6H, t, J=7 Hz), 0.90–1.00 (1H, m), 1.13–1.58 (4H, m), 3.74 (1H, d, J=8 Hz), 4.22 (1H, dd, J=3, 8 Hz), 5.97 (2H, s), 6.72–6.80 (2H, m), 6.82 (1H, s)

FAB MS m/z: 281 [M+H]⁺

Preparation 11-5)

(2RS,3RS)-2-(3,4-Methylenedioxyphenyl)-3-hydroxy-5-methylhexanoic acid (229 mg)

mp: 141–143° C.

NMR (CDCl₃, δ): 0.78–0.90 (6H, m), 0.95–1.08 (1H, m), 1.18–1.37 (1H, m), 1.73–1.90 (1H, m), 3.46 (1H, d, J=8 Hz), 4.10–4.19 (1H, m), 5.95 (2H, s), 6.70–6.90 (3H, m)

FAB MS m/z: 267 [M+H]⁺

Preparation 11-6)

(2RS,3RS)-2-(3,4-Methylenedioxyphenyl)-3-hydroxy-4-cyclohexylbutyric acid (175 mg)

mp: 171° C.

NMR (CDCl₃, δ): 0.60–1.80 (13H, m), 3.45 (1H, d, J=9 Hz), 4.15–4.25 (1H, m), 5.94 (2H, s), 6.70–6.80 (3H, m)

FAB MS m/z: 307 [M+H]⁺

Preparation 11-7

(2RS,3RS)-2-(3,4-Methylenedioxyphenyl)-3-hydroxyvaleric acid (362 mg)

mp: 124–126° C.

NMR (CDCl₃, δ): 0.92 (3H, t, J=8 Hz), 1.20–1.50 (2H, m), 3.50 (1H, d, J=8 Hz), 4.00–4.10 (1H, m), 5.95 (2H, s), 6.70–6.80 (3H, m)

FAB MS m/z: 239 [M+H]⁺

Preparation 11-8)

(2RS,3RS)-2-(3,4-Methylenedioxyphenyl)-3-hydroxy-5,5-dimethylhexanoic acid (320 mg)

mp: 186–187° C.

NMR (CDCl$_3$, δ): 0.87 (9H, s), 1.27 (2H, t, J=8 Hz), 3.48 (1H, d, J=8 Hz), 4.15–4.25 (1H, m), 5.95 (2H, s), 6.70–6.80 (3H, m)

FAB MS m/z: 279 [M–H]$^-$

Preparation 11-9)

(2RS,3RS)-3-Hydroxy-4-methyl-2-(3,4-methylenedioxyphenyl)valeric acid (710 mg)

mp: 105–110° C.

NMR (DMSO-d$_6$, δ): 0.68 (3H, d, J=8 Hz), 0.81 (3H, d, J=8 Hz), 3.40 (1H, d, J=10 Hz), 3.88 (1H, dd, J=1, 10 Hz), 5.98 (2H, s), 6.78 (1H, d, J=8 Hz), 6.84 (1H, d, J=8 Hz), 6.90 (1H, s)

FAB MS: 252 [M+H]$^+$

Preparation 11-10)

(2RS,3SR)- and (2RS,3RS)-3-Hydroxy-2-(3,4-methylenedioxyphenyl)-3-phenylpropionic acid was obtained in substantially the same manner as that of Preparation 14-1).

The stereoisomers were separated by silica gel column chromatography (eluent; n-hexane:ethyl acetate=2:1) to give more polar isomer (220 mg) and less polar isomer (164 mg). The stereostructures of the more polar and the less polar isomers were assigned as (2RS,3SR)- and (2RS,3RS)-configurations respectively.

More polar isomer:

NMR (CDCl$_3$, δ): 3.84 (1H, d, J=9 Hz), 5.12 (1H, d, J=9 Hz), 5.88 (2H, d, J=5 Hz), 6.53 (1H, dd, J=1, 8 Hz), 6.60 (1H, d, J=8 Hz), 6.69 (1H, d, J=1 Hz), 7.12–7.17 (2H, m), 7.18–7.25 (3H, m)

FAB MS: 269.2 [M–OH]$^+$

Less polar isomer:

mp: 145–148° C.

NMR (CDCl$_3$, δ): 3.80 (1H, d, J=8 Hz), 5.22 (1H, d, J=8 Hz), 5.96 (2H, s), 6.76 (2H, s), 6.92 (1H, s), 7.25–7.34 (5H, m)

FAB MS: 269.1 [M–OH]$^+$

Preparation 11-11)

(2RS,3SR)- and (2RS,3RS)-3-Hydroxy-2-(3,4-methylenedioxybenzyl)-3-phenylpropionic acid was obtained in substantially the same manner as that of Preparation 14-1).

The stereoisomers were separated by silica gel column chromatography (eluent; n-hexane:ethyl acetate=3:2) to give more polar isomer (335 mg) and less polar isomer (615 mg). The stereostructures of the more polar and the less polar isomers were assigned as (2RS,3SR)- and (2RS,3RS)-configurations respectively.

More polar isomer:

mp: 130–133° C.

NMR (DMSO-d$_6$, δ): 2.20 (1H, dd, J=4, 14 Hz), 2.54 (1H, d, J=14 Hz), 2.74–2.81 (1H, m), 4.63 (1H, d, J=8 Hz), 5.93 (2H, s), 6.47 (1H, dd, J=1, 8 Hz), 6.57 (1H, d, J=1 Hz), 6.73 (1H, d, J=8 Hz), 7.22–7.40 (5H, m)

FAB MS: 300 [M]$^+$

Less polar isomer:

NMR (DMSO-d$_6$, δ): 2.70–2.82 (2H, m), 2.93–3.03 (1H, m), 4.65 (1H, d, J=8 Hz), 5.93 (2H, s), 6.57 (1H, d, J=8 Hz), 6.66 (1H, d, J=1 Hz), 6.76 (1H, d, J=8 Hz), 7.19–7.37 (5H, m)

FAB MS: 300 [M]$^+$

Preparation 11-12)

(2RS)-2-(3,4-Methylenedioxyphenyl)-3-phenylpropionic acid (422 mg) was obtained in substantially the same manner as that of Preparation 8-3).

NMR (CDCl$_3$, δ): 3.00 (1H, dd, J=7, 14 Hz), 3.35 (1H, dd, J=9, 14 Hz), 3.78 (1H, dd, J=7, 9 Hz), 5.95 (2H, t, J=1 Hz), 6.73 (2H, s), 6.86 (1H, s), 7.07–7.13 (2H, m), 7.17–7.28 (3H, m)

FAB MS: 270.2 [M]$^+$

Preparation 12-1)

To a solution of 1,4-benzodioxane-6-acetic acid (5.0 g) and potassium carbonate (2.13 g) in dimethylformamide (20 ml) was added benzyl bromide (4.84 g) at room temperature. After being stirred at the same temperature for 3 hours, the mixture was poured into water (200 ml) and extracted with diethyl ether (150 ml). The organic layer was washed with 5% hydrochloric acid solution, 1M aqueous sodium bicarbonate solution and brine, dried over magnesium sulfate, and concentrated in vacuo to afford benzyl 1,4-benzodioxane-6-acetate (7.08 g) as an oil.

NMR (CDCl$_3$, δ): 3.54 (2H, s), 4.22 (4H, s), 5.10 (2H, s), 6.70–6.82 (3H, m), 7.28–7.40 (5H, m)

The following compounds were obtained in substantially the same manner as that of Preparation 12-1).

Preparation 12-2)

Benzyl 2-naphthylacetate (5.38 g)

This product was immediately used for the next step.

Preparation 12-3)

Benzyl 3,4-dimethoxyphenylacetate (6.80 g)

This product was immediately used for the next step.

The following compounds were obtained in substantially the same manner as that of Preparation 8-2).

Preparation 13-1)

Benzyl (2RS,3RS)-2-(1,4-benzodioxan-6-yl)-3-hydroxyheptanoate (742 mg)

NMR (CDCl$_3$, δ): 0.78–0.90 (3H, m), 1.20–1.52 (6H, m), 3.46–3.52 (1H, m), 4.06–4.20 (1H, m), 4.24 (4H, s), 5.02–5.23 (2H, m), 6.70–6.92 (3H, m), 7.20–7.40 (5H, m)

FAB MS m/z: 371 [M+H]$^+$

Preparation 13-2)

Benzyl (2RS,3RS)-2-(2-naphthyl)-3-hydroxyheptanoate (742 mg)

NMR (CDCl$_3$, δ): 0.78 (3H, t, J=7 Hz), 1.10–1.52 (6H, m), 2.74 (1H, d, J=7 Hz), 3.30 (1H, d, J=8 Hz), 4.22–4.35 (1H, m), 5.08 (1H, d, J=11 Hz), 5.20 (1H, d, J=11 Hz), 7.15–7.28 (5H, m), 7.35–7.51 (3H, m), 7.70–7.88 (4H, m)

FAB MS m/z: 363 [M+H]$^+$

Preparation 13-3)

Benzyl (2RS,3RS)-2-(3,4-dimethoxyphenyl)-3-hydroxyheptanoate (682 mg)

mp: 64–65° C.

NMR (CDCl$_3$, δ): 0.88 (3H, t, J=8 Hz), 1.20–1.52 (6H, m), 3.55 (1H, d, J=7 Hz), 3.82 (3H, s), 3.88 (3H, s), 4.10–4.21 (1H, m), 5.08 (1H, d, J=11 Hz), 5.18 (1H, d, J=11 Hz), 6.80–6.92 (3H, m), 7.20–7.35 (5H, m)

FAB MS m/z: 373 [M+H]$^+$

Preparation 14-1)

To a solution of benzyl (2RS,3RS)-2-(1,4-benzodioxan-6-yl)-3-hydroxyheptanoate (720 mg) in methanol (10 ml)

was catalytically reduced with 10% palladium on carbon (100 mg) under 3 atmospheric pressure of hydrogen for 1 hour. The catalyst was removed by filtration and the filtrate was evaporated to afford (2RS,3RS)-2-(1,4-benzodioxan-6-yl)-3-hydroxyheptanoic acid (521 mg).

NMR (CDCl$_3$, δ): 0.80–0.92 (3H, m), 1.08–1.55 (6H, m), 3.45–3.50 (1H, m), 4.03–4.20 (1H, m), 4.24 (4H, s), 6.70–6.92 (3H, s)

FAB MS m/z: 281 [M+H]$^+$

The following compounds were obtained in substantially the same manner as that of Preparation 14-1).

Preparation 14-2)

(2RS,3RS)-2-(2-Naphthyl)-3-hydroxyheptanoic acid (474 mg)

mp: 127–128° C.

NMR (CDCl$_3$, δ): 0.77 (3H, t, J=7 Hz), 1.10–1.52 (6H, m), 3.76 (1H, d, J=8 Hz), 4.24–4.53 (1H, m), 7.38–7.52 (3H, m), 7.75–7.85 (4H, m)

FAB MS m/z: 273 [M+H]$^+$

Preparation 14-3)

(2RS,3RS)-2-(3,4-Dimethoxyphenyl)-3-hydroxyheptanoate (521 mg)

mp: 125–126° C.

NMR (CDCl$_3$, δ): 0.89 (3H, t, J=8 Hz), 1.25–1.57 (6H, m), 3.53 (1H, d, J=8 Hz), 3.87 (6H, s), 4.12–4.22 (1H, m), 6.80–6.96 (3H, m)

FAB MS m/z: 282 [M+H]$^+$

The following compounds were obtained in substantially the same manner as that of Preparation 8-2).

Preparation 15-1)

Benzyl 3-hydroxy-2-(3,4-methylenedioxyphenyl)-4-phenylbutyrate (1.77 g)

NMR (CDCl$_3$, δ) 2.30–2.79 (4H, m), 3.55–3.62 (1H, m), 5.04–5.21 (2H, m), 5.96, 5.97 (total 2H, s), 6.79 (2H, s), 6.88, 6.93 (total 1H, s), 7.13–7.33 (10H, m)

Preparation 15-2)

Benzyl 3-hydroxy-2,3-bis(3,4-methylenedioxyphenyl)-propionate (1.87 g)

NMR (CDCl$_3$, δ): 3.77–3.82 (1H, m), 5.02–5.27 (3H, m), 5.88–5.99 (5H, m), 6.50–7.08 (6H, m), 7.22–7.34 (5H, m)

Preparation 15-3)

Benzyl 3-hydroxy-2-(3,4-methylenedioxyphenyl)-3-(3,4,5-trimethoxyphenyl)propionate (2.10 g)

NMR (CDCl$_3$, δ): 2.45 (0.3H, d, J=1 Hz), 3.02 (0.7H, d, J=3 Hz), 3.72, 3.78 (total 9H, s), 4.90 (0.3H, d, J=14 Hz), 5.03–5.12 (1H, m), 5.08 (0.3H, d, J=14 Hz), 5.13 (0.7H, d, J=14 Hz), 5.25 (0.7H, d, J=14 Hz), 5.90 (1.4H, s), 5.98 (0.6H, s), 6.33 (1.4H, s), 6.52–6.66 (2H, m), 6.63 (0.6H, s), 6.76–7.07 (1H, m), 7.24–7.35 (5H, m)

Preparation 15-4)

Benzyl 3-hydroxy-2-(3,4-methylenedioxyphenyl)-3-(4-methoxycarbonylphenyl)propionate (2.02 g)

NMR (CDCl$_3$, δ): 3.76–3.94 (4H, m), 4.85–5.18 (3H, m), 5.89–6.00 (3H, m), 6.57–7.04 (3H, m), 7.18–7.49 (7H, m), 7.72–7.93 (2H, m)

Preparation 15-5)

Benzyl 3-hydroxy-2-(3,4-methylenedioxyphenyl)-3-(4-biphenylyl)propionate (670 mg)

NMR (CDCl$_3$, δ): 3.06 (0.7H, d, J=4 Hz), 3.86–3.92 (1H, 10 m), 4.70 (0.3H, d, J=6 Hz), 4.87 (0.3H, d, J=12 Hz), 5.04 (0.3H, d, J=12 Hz), 5.12 (0.7H, d, J=12 Hz), 5.15–5.25 (1H, m), 5.24 (0.7H, d, J=12 Hz), 5.88–5.99 (2H, m), 6.53–7.02 (3H, m), 7.18–7.60 (14H, m)

Preparation 15-6)

Benzyl 3-hydroxy-2-(3,4-methylenedioxyphenyl)-3-(2-n-butyl-1-tert-butoxycarbonyl-1H-imidazol-4-yl)propionate (2.39 g)

NMR (CDCl$_3$, δ): 0.90–0.97 (3H, m), 1.31–1.42 (2H, m), 1.56, 1.57 (total 9H, s), 1.58–1.71 (2H, m), 2.75 (0.5H, d, J=5 Hz), 2.89–2.98 (2H, m), 3.38 (0.5H, d, J=7 Hz), 4.17 (0.5H, d, J=7 Hz), 4.23 (0.5H, d, J=9 Hz), 4.96–5.05 (3H, m), 5.92, 5.95 (total 2H, s), 6.66–6.94 (3H, m), 7.09–7.30 (6H, m)

Preparation 16-1)

(2RS,3RS)- and (2RS,3SR)-3-Hydroxy-2-(3,4-methylenedioxyphenyl)-4-phenylbutyric acid was obtained in substantially the same manner as that of Preparation 14-1).

The stereoisomers were separated by silica gel column chromatography (eluent; n-hexane:ethyl acetate=3:2) to give more polar isomer (136 mg) and less polar isomer (400 mg). The stereostructures of the more polar and the less polar isomers were assigned as (2RS,3RS)- and (2RS,3SR)-configurations respectively.

More polar isomer:

mp : 70–75° C.

NMR (DMSO-d$_6$, δ): 2.50–2.60 (2H, m), 3.12 (1H, d, J=7 Hz), 3.79–3.88 (1H, m), 5.92 (2H, s), 6.69 (1H, d, J=8 Hz), 6.76 (1H, d, J=8 Hz), 6.88 (1H, s), 7.10–7.18 (3H, m), 7.20–7.27 (2H, m)

Less polar isomer:

mp: 134–137° C.

NMR (DMSO-d$_6$, δ): 2.54 (1H, dd, J=9, 15 Hz), 2.70 (1H, dd, J=4, 15 Hz), 3.40 (1H, d, J=8 Hz), 4.19 (1H, ddd, J=4, 8, 9 Hz), 5.98 (2H, s), 6.76 (1H, d, J=8 Hz), 6.83 (1H, d, J=8 Hz), 6.92 (1H, s), 7.16–7.21 (3H, m), 7.24–7.30 (2H, m)

Preparation 16-2)

(2RS,3SR)- and (2RS,3RS)-3-Hydroxy-2,3-bis(3,4-methylenedioxyphenyl)propionic acid was obtained in substantially the same manner as that of Preparation 14-1).

The stereoisomers were separated by silica gel column chromatography (eluent; n-hexane:ethyl acetate=1:1) to give more polar isomer (309 mg) and less polar isomer (310 mg). The stereostructures of the more polar and the less polar isomers were assigned as (2RS,3SR)- and (2RS,3RS)-configurations respectively.

More polar isomer:

NMR (DMSO-d$_6$, δ): 3.62 (1H, d, J=10 Hz), 4.90 (1H, d, J=10 Hz), 5.89–5.92 (4H, m), 6.57 (2H, dt, J=1, 6 Hz), 6.67 (2H, t, J=6 Hz), 6.80 (2H, d, J=1 Hz)

FAB MS: 330 [M]$^+$

Less polar isomer:

mp: 167–170° C.

NMR (DMSO-d$_6$, δ): 3.67 (1 H, d, J=9 Hz), 4.89 (1 H, d, J=9 Hz), 5.98 (4H, s), 6.77–6.86 (4H, m), 6.90 (1H, s), 6.99 (1H, s)

Preparation 16-3)

(2RS,3SR)- and (2RS,3RS)-3-Hydroxy-2-(3,4-methylenedioxyphenyl)-3-(3,4,5-trimethoxyphenyl)

propionic acid was obtained in substantially the same manner as that of Preparation 14-1).

The stereoisomers were separated by silica gel column chromatography (eluent; n-hexane:ethyl acetate=2:3) to give more polar isomer (227 mg) and less polar isomer (190 mg). The stereostructures of the more polar and the less polar isomers were assigned as (2RS,3SR)- and (2RS,3RS)-configurations respectively.

More polar isomer:

mp: 139–142° C. NMR (DMSO-$d_6$, δ): 3.56 (3H, s), 3.62 (1H, d, J=10 Hz), 3.64 (6H, s), 4.92 (1H, d, J=10 Hz), 5.92 (2H, s), 6.42 (2H, s), 6.59 (1H, dd, J=1, 8 Hz), 6.69 (1H, d, J=8 Hz), 6.79 (1H, d, J=1 Hz)

FAB MS: 376 [M]$^+$

Less polar isomer:

mp: 188–192° C.

NMR (DMSO-$d_6$, δ): 3.62 (3H, s), 3.70 (1H, d, J=9 Hz), 3.73 (6H, s), 4.96 (1H, d, J=9 Hz), 5.98 (2H, s), 6.63 (2H, s), 6.75–6.84 (2H, m), 6.99 (1H, s)

Preparation 16-4)

(2RS,3SR)- and (2RS,3RS)-3-Hydroxy-2-(3,4-methylenedioxyphenyl)-3-(4-methoxycarbonylphenyl) propionic acid was obtained in substantially the same manner as that of Preparation 14-1).

The stereoisomers were separated by silica gel column chromatography (eluent; n-hexane:ethyl acetate=1:1) to give more polar isomer (260 mg) and less polar isomer (180 mg). The stereostructures of the more polar and the less polar isomers were assigned as (2RS,3SR)- and (2RS,3RS)-configurations respectively.

More polar isomer:

NMR (DMSO-$d_6$, δ): 3.60 (1H, d, J=9 Hz), 3.82 (3H, s), 5.03 (1H, d, J=9 Hz), 5.90, 5.91 (total 2H, 5), 6.55 (1H, d, J=9 Hz), 6.66 (1H, d, J=9 Hz), 6.80 (1H, s), 7.29 (2H, d, J=8 Hz), 7.75 (2H, d, J=8 Hz)

FAB MS: 327.1 [M–OH]$^+$

Less polar isomer:

mp: 180–188° C.

NMR (DMSO-$d_6$, δ): 3.76 (1 H, d, J=8 Hz), 3.83 (3H, s), 5.10 (1 H, d, J=8 Hz), 5.98 (2H, s), 6.75 (1 H, d, J=8 Hz), 6.79 (1H, d, J=8 Hz), 6.98 (1H, s), 7.48 (2H, d, J=9 Hz), 7.88 (2H, d, J=9 Hz)

Preparation 16-5)

(2RS,3SR)- and (2RS,3RS)-3-Hydroxy-2-(3,4-methylenedioxyphenyl)-3- (4-biphenylyl)propionic acid was obtained in substantially the same manner as that of Preparation 14-1).

The stereoisomers were separated by silica gel column chromatography (eluent; n-hexane:ethyl acetate=2:1-ethyl acetate-methanol) to give more polar isomer (290 mg) and less polar isomer (155 mg). The stereostructures of the more polar and the less polar isomers were assigned as (2RS, 3SR)- and (2RS,3RS)-configurations respectively.

More polar isomer:

NMR (DMSO-$d_6$, δ): 3.42 (1H, d, J=7 Hz), 4.78 (1H, d, J=7 Hz), 5.91, 5.93 (total 2H, s), 6.69 (2H, s), 6.94 (1H, s), 7.29–7.36 (3H, m), 7.39–7.48 (2H, m), 7.50 (2H, d, J=9 Hz), 7.61 (2H, d, J=9 Hz)

Less polar isomer:

NMR (DMSO-$d_6$, δ): 3.77 (1H, d, J=8 Hz), 5.03 (1H, d, J=8 Hz), 5.99 (2H, s), 6.84 (2H, s), 7.02 (1H, s), 7.32–7.37 (1H, m), 7.42–7.49 (4H, m), 7.60 (2H, d, J=9 Hz), 7.67 (2H, d, J=9 Hz)

Preparation 16-6)

(2RS,3SR) and (2RS,3RS)-3-Hydroxy-2-(3,4-methylenedioxyphenyl)-3-(2-n-butyl-1-tert-butoxycarbonyl-1H-imidazol-4-yl)propionic acid was obtained in substantially the same manner as that of Preparation 14-1).

The stereoisomers were separated by silica gel column chromatography (eluent; n-hexane:ethyl acetate=2:1) to give more polar isomer (824 mg) and less polar isomer (510 mg). The stereostructures of the more polar and the less polar isomers were assigned as (2RS,3SR)- and (2RS,3RS)-configurations respectively.

More polar isomer:

NMR (DMSO-$d_6$, δ): 0.89 (3H, t, J=8 Hz), 1.24–1.36 (2H, m), 1.50–1.63 (2H, m), 1.56 (9H, s), 2.77–2.88 (2H, m), 3.60–3.64 (1H, br), 4.54–4.59 (1H, br), 5.91 (2H, s), 6.64–7.10 (4H, m)

Less polar isomer:

NMR (DMSO-$d_6$, δ): 0.90 (3H, t, J=7 Hz), 1.23–1.39 (2H, m), 1.54–1.65 (2H, m), 1.56 (9H, s), 2.88 (2H, t, J=8 Hz), 3.89 (1H, d, J=9 Hz), 4.90 (1H, d, J=9 Hz), 5.98 (2H, s), 6.69–7.03 (4H, m)

Preparation 17

Benzyl (2RS,3SR)- and (2RS,3RS)-3-hydroxy-2-(3,4-methylenedioxyphenyl)-3-(2-pyridyl)propionate was obtained in substantially the same manner as that of Preparation 8-2).

The stereoisomers were separated by silica gel column chromatography (eluent; n-hexane:ethyl acetate=4:1~2:1) to give more polar isomer (360 mg) and less polar isomer (742 mg). The stereostructures of the more polar and the less polar isomers were assigned as (2RS,3SR)- and (2RS,3RS)-configurations respectively.

More polar isomer:

NMR (CDCl$_3$, δ): 3.92 (1H, d, J=8 Hz), 4.41 (1H, d, J=8 Hz), 5.10–5.19 (1H, m), 5.12 (1H, d, J=14 Hz), 5.25 (1H, d, J=14 Hz), 5.91 (2H, t, J=1 Hz), 6.56–6.87 (4H, m), 7.12–7.22 (2H, m), 7.25–7.36 (4H, m), 7.44 (1H, dt, J=1, 8 Hz), 8.52 (1H, d, J=6 Hz)

Less polar isomer:

NMR (CDCl$_3$, δ): 3.85 (1H, d, J=7 Hz), 4.04 (1H, d, J=8 Hz), 5.00 (1H, d, J=13 Hz), 5.13 (1H, d, J=13 Hz), 5.36 (1H, dd, J=7, 8 Hz), 5.93 (2H, s), 6.67 (2H, d, J=1 Hz), 6.86 (1H, s), 7.11–7.20 (4H, m), 7.26–7.32 (3H, m), 7.54 (1H, dt, J=1, 8 Hz), 8.50 (1H, dd, J=1, 6 Hz)

Preparation 18

(2RS,3SR)-3-Hydroxy-2-(3,4-methylenedioxyphenyl)-3-(2-pyridyl)propionic acid was obtained in substantially the same manner as that of Preparation 14-1).

NMR (DMSO-$d_6$, δ): 3.90 (1H, d, J=10 Hz), 5.03 (1H, d, J=10 Hz), 5.90 (2H, d, J=1 Hz), 6.57 (1H, d, J=8 Hz), 6.65 (1H, d, J=8 Hz), 6.77 (1H, s), 7.14 (1H, dd, J=6, 8 Hz), 7.30 (1H, d, J=8 Hz), 7.63 (1H, dt, J=1, 8 Hz), 8.37 (1H, d, J=6 Hz)

FAB MS: 288.1 [M+H]$^+$

Preparation 19

(2RS,3RS)-3-Hydroxy-2-(3,4-methylenedioxyphenyl)-3-(2-pyridyl)propionic acid was obtained in substantially the same manner as that of Preparation 14-1).

NMR (DMSO-$d_6$, δ): 4.03 (1H, d, J=8 Hz), 5.14 (1H, d, J=8 Hz), 5.95 (2H, t, J=1 Hz), 6.62 (1 H, d, J=9 Hz), 6.72

(1H, d, J=9 Hz), 6.88 (1H, s), 7.18–7.23 (1H, m), 7.27–7.31 (1H, m), 7.68 (1H, dt, J=1, 8 Hz), 8.48 (1H, d, J=6 Hz)

FAB MS: 288.1 [M+H]$^+$

Preparation 20

A solution of (2RS,3SR)-3-hydroxy-2-(3,4-methylenedioxy-phenyl)-3-(4-methoxycarbonylphenyl)propionic acid (80 mg) in 1N aqueous sodium hydroxide solution (1.2 ml) and methanol (5 ml) was stirred at ambient temperature for 18 hours. The reaction was quenched with iN-hydrochloric acid and then the resulting mixture was diluted with ethyl acetate. The layers were separated and the organic layer was washed with brine. The organic layer was dried and evaporated to afford (2RS,3SR)-3-hydroxy-2-(3,4-methylenedioxyphenyl)-3-(4-carboxyphenyl)propionic acid (60 mg).

mp: >250° C.

NMR (DMSO-d$_6$, δ): 3.66 (1H, d, J=1 Hz), 5.07 (1H, d, J=11 Hz), 5.90, 5.92 (total 2H, s), 6.55 (1H, d, J=10 Hz), 6.65 (1H, d, J=10 Hz), 6.78 (1H, s), 7.26 (2H, d, J=9 Hz), 7.72 (2H, d, J=9 Hz)

Preparation 21

To a solution of 2-n-butyl-1H-imidazole-4-carbaldehyde (800 mg) and N,N-dimethylaminopyridine (65 mg) in acetonitrile (15 ml) was added di-tert-butyl dicarbonate (1.20 g) and the solution was stirred at ambient temperature for 20 minutes. The mixture was evaporated in vacuo and then the residue was diluted with ethyl acetate. The organic solution was washed successively with saturated aqueous ammonium chloride solution, saturated aqueous sodium bicarbonate. The organic layer was dried and evaporated to afford 2-n-butyl-1-tert-butoxycarbonyl-1H-imidazole-4-carbaldehyde.

NMR (CDCl$_3$, δ): 0.97 (3H, t, J=8 Hz), 1.38–1.51 (2H, m), 1.65 (9H, s), 1.70–1.82 (2H, m), 3.04 (2H, t, J=8 Hz), 7.99 (1H, s), 9.89 (1H, s)

Preparation 22

A solution of (2RS,3SR)-3-hydroxy-2-(3,4-methylenedioxyphenyl)-3-(2-n-butyl-1-tert-butoxycarbonyl-1H-imidazol-4-yl)propionic acid (250 mg) in 4N hydrogen chloride-ethyl acetate solution (3 ml) was stirred at ambient temperature for 18 hours. The solution was evaporated in vacuo and then the residue was solidified with ether. Resulting powder was collected by filtration and dried to afford (2RS,3SR)-3-hydroxy-2-(3,4-methylenedioxyphenyl)-3-(2-n-butyl-1H-imidazol-4-yl)propionic acid hydrochloride (65 mg).

NMR (DMSO-d$_6$, δ): 0.80–0.90 (3H, m), 1.03–1.12 (2H, m), 1.53–1.66 (2H, m), 2.73–2.85 (2H, m),3.90 (1H, d, J=10 Hz), 5.12 (1H, d, J=10 Hz), 5.92, 5.95 (total 2H, s), 6.62–6.84 (3H, m), 7.12 (1H, s)

FAB MS: 333.1 [M+H]$^+$

Preparation 23-1)

Benzyloxycarbonyl-L-Trp(CH$_2$CO$_2$$^t$Bu)-OH was obtained according to a similar manner to that of Preparation 29-1).

NMR (CDCl$_3$, δ): 1.39 (9H, s), 3.30–3.38 (2H, m), 4.62 (2H, s), 4.68–4.77 (1H, m), 5.02–5.15 (2H, m), 5.31 (1H, d, J=7 Hz), 6.89 (1H, s), 7.03–7.09 (1H, m), 7.15–7.19 (2H, m), 7.27–7.36 (4H, m), 7.55 (1H, d, J=7 Hz), 7.98 (1H, s)

ESI-MS (m/z): 453 [M+H]

Preparation 23-2)

Benzyloxycarbonyl-L-Trp(CH$_2$CO$_2$$^t$Bu)-OMe was obtained according to a similar manner to that of Example 30-2).

NMR (CDCl$_3$, δ): 1.40 (9H, s), 3.25–3.30 (2H, m), 3.67 (3H, s), 4.62–4.73 (3H, m), 5.00–5.15 (2H, m), 5.25–5.32 (1H, m), 6.80–6.87 (1H, m), 7.05–7.11 (1H, m), 7.15–7.38 (7H, m), 7.50 (1H, d, J=7 Hz)

ESI-MS (m/z): 467 [M+H]

Preparation 23-3)

A solution of benzyloxycarbonyl-L-Trp(CH$_2$CO$_2$$^t$Bu)-OMe (1.00 g) in trifluoroacetic acid (200 ml) was stirred at ambient temperature for 30 minutes. The solution was concentrated in vacuo and to the residue was added 0.5N hydrochloric acid (30 ml) and ethyl acetate (30 ml). The organic layer was washed with 0.5N hydrochloric acid (30 ml) and brine (30 ml) successively and the organic layer was dried over magnesium sulfate. The solution was concentrated in vacuo to give benzyloxycarbonyl-L-Trp(CH$_2$CO$_2$H)-OMe (1.57 g) as an oil.

Rf: 0.61 (silica gel, chloroform:methanol:acetic acid= 16:1:1)

Preparation 23-4)

To a solution of benzyloxycarbonyl-L-Trp(CH$_2$CO$_2$H)-OMe (700 mg), dimethylamine monohydrochloride (167 mg) and 1-hydroxybenzotriazole (277 mg) in N,N-dimethylformamide (5 ml) was added 1-ethyl-3-(3-dimethylaminopropyl)carbodiimide (318 mg) under ice-bath cooling. After being stirred at ambient temperature overnight, the mixture was poured into water (20 ml) and extracted with ethyl acetate (20 ml). The organic layer was washed with 0.5N hydrochloric acid (20 ml×2), saturated aqueous sodium bicarbonate solution (20 ml×2) and brine (20 ml) successively and dried over magnesium sulfate. The solution was concentrated in vacuo and the residue was purified by preparative thin layer silica gel chromatography (hexane:ethyl acetate, 1:3) to give benzyloxycarbonyl-L-Trp(CH$_2$CONMe$_2$)-OMe (323 mg) as an oil.

NMR (CDCl$_3$, δ): 2.93 (6H, s), 3.20–3.32 (2H, m), 3.68 (3H, s), 4.65–4.74 (1H, m), 4.82 (2H, s), 4.97–5.16 (2H, m), 5.28–5.37 (1H, m), 6.87 (1H, s), 7.02–7.10 (1H, m), 7.15–7.38 (7H, m), 7.50 (1H, d, J=7 Hz)

ESI-MS (m/z): 438 [M+H]

Preparation 23-5)

A mixture of benzyloxycarbonyl-L-Trp(CH$_2$CONMe$_2$)-OMe (305 mg) and 10% palladium on activated carbon (300 mg) in methanol (20 ml), water (2 ml) and hydrogen chloride (0.25 ml, 4N ethyl acetate solution) was shaken under hydrogen atmosphere (3 atmospheric pressure) at ambient temperature for 1 hour. The mixture was filtered through a bed of celite and the filtrate was concentrated in vacuo. The residue was triturated with ethyl acetate to give HCl-H-L-Trp(CH$_2$CONMe$_2$)-OMe (211 mg) as an amorphous powder.

NMR (DMSO-d$_6$, δ): 2.84 (3H, s), 3.09 (3H, s), 3.18–3.35 (2H, m), 3.63 (3H, s), 4.12–4.23 (1H, s), 5.08 (2H, s), 6.98–7.17 (3H, s), 7.34 (1H, d, J=7 Hz), 7.53 (1H, d, J=7 Hz), 8.64 (2H, s)

ESI-MS (m/z): 304 [M+H]

Preparation 24-1)

tert-Butoxycarbonyl-L-Trp(CH$_2$CH$_2$CO$_2$Et)-OMe was obtained as a slightly brown oil according to a similar manner to that of Example 30-2).

NMR (CDCl$_3$, δ): 1.21 (3H, t, J=7 Hz), 1.45 (9H, s), 2.78 (2H, t, J=8 Hz), 3.23–3.27 (2H, m), 3.70 (3H, s), 4.12 (2H, q, J=7 Hz), 4.40 (2H, t, J=8 Hz), 4.57– 4.66 (1H, m), 5.00–5.07 (1H, m), 6.93 (1H, s), 7.10 (1H, t, J=8 Hz), 7.21 (1H, t, J=8 Hz), 7.28–7.37 (1H, m), 7.53 (1H, d, J=8 Hz)

Preparation 24-2)

HCl.H-L-Trp(CH$_2$CH$_2$CO$_2$Et)-OMe was obtained as a slightly yellow solid according to a similar manner to that of Preparation 25-2).

NMR (DMSO-d$_6$, δ): 1.14 (3H, t, J=8 Hz), 2.80 (2H, t, J=7 Hz), 3.27 (2H, t, J=7 Hz), 3.67 (3H, s), 4.03 (2H, q, J=8 Hz), 4.21 (1H, t, J=7 Hz), 4.38 (2H, t, J=7 Hz), 7.06 (1H, t, J=8 Hz), 7.17 (1H, t, J=8 Hz), 7.23 (1H, s), 7.49 (1H, d, J=8 Hz), 7.52 (1H, d, J=8 Hz), 8.50–8.56 (2H, br s)

Preparation 25-1)

To a solution of Boc-L-Trp(CHO)-OH (1.00 g) and triethylamine (396 mg) in THF (tetrahydrofuran) (10 ml) was added pivaloyl chloride (399 mg) at −78° C. under nitrogen atmosphere. The mixture was stirred in ice bath for 30 minutes. To the solution was added a mixture which was methanesulfone amide (430 mg) in DMSO (dimethyl sulfoxide) (10 ml) and 1.0 M lithium bis(trimethylsilyl) amide in THF (9.1 ml) at room temperature. After being stirred for 5 hours at the same temperature, the reaction mixture was quenched by 1.0 M hydrochloric acid. The mixture was extracted with ethyl acetate (50 ml), and the solution was washed with brine, dried over magnesium sulfate and concentrated in vacuo. The residue was crystallized from diethyl ether and n-hexane to give Boc-L-Trp (CHO)-NHSO$_2$CH$_3$ (568 mg).

NMR (CDCl$_3$, δ): 1.30 (9H, s), 2.88–3.14 (3H, m), 3.22 (3H, s), 4.30–4.42 (1H, m), 7.16–7.42 (3H, m), 7.56–7.74 (1H, m), 7.82–7.92 (1H, m), 8.18–8.30 (1H, m)

ESI-MS: 410 [M+H]

Preparation 25-2)

The solution of Boc-L-Trp(CHO)-NHSO$_2$CH$_3$ (568 mg) in 4N hydrogenchloride-ethyl acetate solution (20 ml) was stirred at room temperature for 30 minutes. After being evaporated in vacuo, the residue was solidified with diethyl ether to give HCl.H-L-Trp(CHO)-NHSO$_2$CH$_3$ (420 mg).

Preparation 26-1)

Benzyl 3-hydroxy-3,3-di(2-pyridyl)-2-(3,4-methylenedioxyphenyl)propionate was obtained as a slightly yellow amorphous powder according to a similar manner to that of Preparation 15-6).

NMR (CDCl$_3$, δ): 4.86 (1H, d, J=13 Hz), 5.09 (1H, d, J=13 Hz), 5.38 (1H, s), 5.86 (2H, t, J=1 Hz), 6.24 (1H, s), 6.52 (1H, d, J=8 Hz), 6.60 (1H, d, J=8 Hz), 6.87 (1H, s), 7.01 (1H, dd, J=5, 7 Hz), 7.07–7.16 (3H, m), 7.23–7.28 (3H, m), 7.48–7.60 (2H, m), 7.68 (1H, d, J=8 Hz), 7.76 (1H, d, J=8 Hz), 8.42 (2H, dd, J=1, 8 Hz)

ESI-MS: 454.9 [M+H]

Preparation 26-2)

3-Hydroxy-3,3-di(2-pyridyl)-2-(3,4-methylenedioxyphenyl)propionic acid was obtained as a slightly amorphous powder according to a similar manner to that of Preparation 16-6).

NMR (CDCl$_3$, δ): 5.23 (1H, s), 5.89 (2H, s), 6.57 (1H, d, J=8 Hz), 6.62 (1H, d, J=8 Hz), 6.80 (1H, s), 7.09 (1H, dd, J=4, 7 Hz), 7.24 (1H, dd, J=4, 7 Hz), 7.53–7.64 (3H, m), 7.73 (1H, t, J=8 Hz), 8.38 (1H, d, J=4 Hz), 8.52 (1H, d, J=4 Hz)

ESI-MS: 365 [M+H]

Preparation 27-1)

Ethyl 2-(3,4-methylenedioxyphenyl)-3-cyclopropyl-3-hydroxypropionate was obtained according to a similar manner to that of Preparation 8-2).

NMR (CDCl$_3$, δ): −0.10–0.03 (1H, m), 0.20–0.58 (3H, m), 0.72–0.92 (1H, m), 1.18–1.29 (3H, m), 2.33–2.62 (1H, m), 3.36–3.57 (1H, m), 3.64 (1H, t, J=6 Hz), 4.07–4.23 (2H, m), 5.95 (2H, s), 6.73–6.96 (3H, m)

ESI-MS (m/z): 479 [M+H]

Preparation 27-2)

(2RS,3SR)-2-(3,4-Methylenedioxyphenyl)-3-cyclopropyl-3-hydroxypropionic acid was obtained according to a similar manner to that of Preparation 8-3).

NMR (DMSO-d$_6$, δ): −0.05–0.03 (1H, m), 0.10–0.30 (3H, m), 0.68–0.92 (1H, m), 2.50 (1H, s), 3.13 (1H, t, J=6 Hz), 3.22 (1H, d, J=6 Hz), 5.93 (2H, s), 6.74 (2H, s), 6.91 (1H, s)

ESI-MS (m/z): 249 [M+H]

Preparation 28-1)

Benzyl (2RS,3SR)-3-hydroxy-3-(2-biphenylyl)-2-(3,4-methylenedioxyphenyl)propionate was obtained as a colorless oil according to a similar manner to that of Preparation 15-6).

NMR (CDCl$_3$, δ): 3.18 (1H, d, J=5 Hz), 3.87 (1H, d, J=9 Hz), 5.02 (1H, d, J=14 Hz), 5.13 (1H, d, J=14 Hz), 5.32 (1H, dd, J=5, 9 Hz), 5.96–5.99 (2H, m), 6.16 (1H, d, J=8 Hz), 6.20 (1H, d, J=2 Hz), 6.48 (1H, d, J=8 Hz), 6.93–6.98 (2H, br s), 7.08 (1H, d, J=9 Hz), 7.12–7.17 (2H, m), 7.22–7.40 (12H, m), 7.65 (1H, d, J=9 Hz)

Preparation 28-2)

(2RS,3SR)-3-Hydroxy-3-(2-biphenylyl)-2-(3,4-methylenedioxyphenyl)propionic acid was obtained as a white amorphous powder according to a similar manner to that of Preparation 16-6).

NMR (CDCl$_3$, δ): 3.69 (1H, d, J=11 Hz), 5.17 (1H, d, J=11 Hz), 5.90 (2H, d, J=5 Hz), 6.17 (1H, d, J=8 Hz), 6.18 (1H, s), 6.53 (1H, d, J=8 Hz), 6.92 (1H, d, J=7 Hz), 6.98–7.05 (2H, br s), 7.18 (1H, t, J=7 Hz), 7.29–7.46 (4H, m), 7.66 (1H, d, J=7 Hz)

ESI-MS: 363 [M+H]

Preparation 29-1)

To a solution of Boc-L-Trp-OBzl (5.00 g), tetra-n-butylammonium sulfate (43 mg) and NaOH (sodium hydroxide) (1.27 g) in methylene chloride (100 ml) was added a solution of ethyl bromoacetate (5.29 g) in methylene chloride (50 ml) in an ice-bath cooling. After being stirred at room temperature for 2 days, the mixture was washed with 5% aqueous potassium hydrogen sulfate solution, 1M aqueous sodium bicarbonate solution and brine, dried over magnesium sulfate, and concentrated in vacuo to afford Boc-L-Trp(CH$_2$COOEt)-OBzl (6.10 g) as an oil.

NMR (CDCl$_3$, δ): 1.30 (3H, t, J=7 Hz), 1.42 (9H, s), 3.29 (2H, d, J=6 Hz), 4.23 (2H, q, J=7 Hz), 4.09–4.26 (3H, m), 5.01–5.22 (2H, m), 7.08–7.40 (9H, m), 7.54 (1H, d, J=9 Hz)

ESI-MS : 481 [M+H]

Preparation 29-2)

HCl.H-L-Trp(CH$_2$COOEt)-OBzl (4.50 g) was obtained according to a similar manner to that of Preparation 25-2) as an amorphous powder.

NMR (DMSO-d$_6$, δ): 1.22 (3H, t, J=7 Hz), 3.19–3.30 (2H, m), 4.14 (2H, q, J=7 Hz), 4.23–4.31 (1H, m), 5.05 (2H, s), 5.10 (2H, dd, J=9, 18 Hz), 7.08 (1H, t, J=8 Hz), 7.12–7.22 (4H, m), 7.29–7.36 (3H, m), 7.48 (1H, d, J=9 Hz), 7.58 (1H, d, J=9 Hz)

ESI-MS: 381 [M+H]

Preparation 30-1)

Boc-L-Trp(CH$_2$COOEt)-NHSO$_2$CH$_3$ (2.08 g) was obtained according to a similar manner to that of Preparation 25-1) as an amorphous powder.

NMR (CDCl$_3$, δ): 1.25 (9H, s), 1.27 (3H, t, J=7 Hz), 3.10 (2H, s), 3.30 (3H, s), 4.22 (2H, q, J=7 Hz), 4.40–4.52 (1H, m), 4.82 (2H, s), 5.05–5.18 (1H, m), 6.95–7.04 (1H, m), 7.12–7.28 (3H, m), 7.60 (1H, d, J=7 Hz), 8.06–8.16 (1H, m)

ESI-MS: 468 [M+H]

Preparation 30-2)

HCl.H-L-Trp(CH$_2$COOEt)-NHSO$_2$CH$_3$ (1.00 g) was obtained according to a similar manner to that of Preparation 25-2) as an amorphous powder.

ESI-MS: 368 [M+H]

Preparation 31-1)

To a solution of benzyl (2RS,3SR)-3-(1-tert-butoxycarbonyl-2-n-butylimidazol-4-yl)-3-hydroxy-2-(3,4-methylenedioxyphenyl)propionate (4.27 g) and triethylamine (909 mg) in dichloromethane (50 ml) was added dropwise methanesulfonyl chloride (1.03 g) at ambient temperature and the mixture was stirred for 2 hours. As the reaction was not completed, methanesulfonyl chloride (500 mg) and triethylamine (450 mg) were added to the mixture and stirred at ambient temperature for additional 2 hours. The solution was washed successively with saturated ammonium chloride aqueous solution, saturated sodium bicarbonate aqueous solution and brine. Drying, filtering and removal of the solvents afforded a crude intermediate methanesulfonate compound. A mixture of the above methanesulfonate compound and 1,8-diazabicyclo[5.4.0]undec-7-ene (3.47 g) in tetrahydrofuran (60 ml) was stirred at ambient temperature for 30 minutes. The resulting mixture was diluted with ethyl acetate followed by washing successively with saturated sodium bicarbonate aqueous solution and brine. Drying, filtering and removal of the solvents afforded a crude product. The crude product was chromatographed on silica gel (eluent; n-hexane:ethyl acetate=8:1-4:1) to give benzyl (E and Z)-3-(1-tert-butoxycarbonyl-2-n-butylimidazol-4-yl)-2-(3,4-methylenedioxyphenyl) propenoate (3.21 g) as a yellow oil.

NMR (CDCl$_3$, δ): 0.87–0.96 (3H, m), 1.26–1.44 (2H, m), 1.52, 1.59 (total 9H, s), 1.56–1.75 (2H, m), 2.89–2.98 (2H, m), 5.23 (1H, s), 5.37 (1H, s), 5.96 (1H, s), 5.98 (1H, s), 6.39 (0.5H, s), 6.69 (0.5H, s), 6.70–6.95 (3H, m), 7.29–7.38 (5H, m), 7.41 (0.5H, s), 7.79 (0.5H, s)

ESI-MS: 505 [M+H]

Preparation 31-2)

3-(1-tert-Butoxycarbonyl-2-n-butylimidazol-4-yl)-2-(3,4-methylenedioxyphenyl)propionic acid was obtained as a white amorphous powder according to a similar manner to that of Preparation 16-6).

NMR (CDCl$_3$, δ): 0.92 (3H, t, J=7 Hz), 1.32–1.41 (2H, m), 1.59 (9H, s), 1.60–1.71 (2H, m), 2.88–2.97 (3H, m), 3.17–3.27 (1H, m), 3.95–4.01 (1H, br), 5.92 (2H, s), 6.72 (2H, s), 6.81 (1H, s), 6.98 (1H, s)

ESI-MS: 417 [M+H]

Preparation 32

1-tert-Butoxycarbonyl-2-n-propyl-4-(hydroxymethyl)-imidazole was obtained as a slightly yellow oil according to a similar manner to that of Preparation 33-1).

NMR (CDCl$_3$, δ): 1.00 (3H, t, J=8 Hz), 1.59 (9H, s), 1.69–1.81 (2H, m), 2.68 (1H, t, J=6 Hz), 2.95 (2H, dd, J=8, 9 Hz), 4.55 (2H, d, J=6 Hz), 7.24 (1H, s)

ESI-MS: 241 [M+H]

Preparation 33-1)

To a solution of 2-n-butyl-4-(hydroxymethyl)imidazole (2.95 g) and N,N-dimethylaminopyridine (234 mg) in acetonitrile (30 ml) was added di-tert-butyl dicarbonate (4.18 g) at 0° C. The solution was stirred at ambient temperature for 40 minutes, and then the solvent was removed in vacuo. The residue was diluted with ethyl acetate and the organic solution was washed successively with saturated ammonium chloride aqueous solution, saturated sodium bicarbonate aqueous solution and brine. Drying, filtering and removal of the solvents afforded a crude product. The crude product was chromatographed on silica gel (50 g, eluent; 10% methanol in chloroform) to give 1-tert-butoxycarbonyl-2-n-butyl-4-(hydroxymethyl)imidazole (4.48 g) as a colorless oil.

NMR (CDCl$_3$, δ): 0.95 (3H, t, J=8 Hz), 1.36–1.46 (2H, m), 1.62 (9H, s), 1.66–1.75 (2H, m), 2.59 (1H, dd, J=4, 7 Hz), 2.98 (2H, dd, J=7, 9 Hz), 4.54 (2H, d, J=7 Hz), 7.23 (1H, s)

ESI-MS: 255 [M+H]

Preparation 33-2)

To a solution of 1-tert-butoxycarbonyl-2-n-butyl-4-(hydroxymethyl)imidazole (4.43 g) in dichloromethane (80 ml) was added triphenylphosphine (5.48 g) followed by carbon tetrabromide (6.93 g) at ambient temperature and the mixture was stirred for 30 minutes. The solvent was removed in vacuo and the residue was purified by silica gel column chromatography (eluent; n-hexane:ethyl acetate= 4:1) to give 1-tert-butoxycarbonyl-2-n-butyl-4-(bromomethyl)imidazole (5.09 g) as a colorless oil.

NMR (CDCl$_3$, δ): 0.96 (3H, t, J=7 Hz), 1.37–1.48 (2H, m), 1.60 (9H, s), 1.67–1.76 (2H, m), 2.98 (2H, dd, J=7, 10 Hz), 4.40 (2H, s), 7.32 (1H, s).

ESI-MS: 317 [M+H]

Preparation 34-1)

To a solution of 3,4-methylenedioxyphenylacetic acid (20.0 g) and N,N-dimethylformamide (0.5 ml) in dichloromethane (250 ml) was added dropwise oxalyl chloride (11.6 ml) at 0° C. and the reaction mixture was stirred at ambient temperature for 20 minutes. Removal of the solvent afforded a crude intermediate acid chloride compound. To a solution of (4S)-4-isopropyloxazolidin-2-one (13.7 g) in tetrahydrofuran (200 ml) was added dropwise n-butyl lithium (66.3 ml, 1.6M n-hexane solution) at −65∼−50° C. over 15 minutes and the solution was stirred at −65° C. for 20 minutes. The mixture was added to a solution of the above acid chloride in dichloromethane (50 ml) at −65° C. and the mixture was stirred for 1 hour. The temperature was raised to ambient temperature and the reaction was quenched with saturated ammonium chloride aqueous solution. The resulting solution was diluted with ethyl acetate and the organic layer was washed successively with saturated sodium bicarbonate aqueous solution and brine. Drying, filtering and removal of the solvents afforded a crude product (35 g). The crude product was chromatographed on silica gel (350 g, eluent; n-hexane-ethyl acetate=4:1) to give (4S)-3-(3,4-methylenedioxyphenyl)acetyl-4-isopropyloxazolidin-2-one (23.36 g) as a white solid.

NMR (CDCl$_3$, δ): 0.80 (3H, d, J=7 Hz), 0.88 (3H, d, J=7 Hz), 2.30–2.40 (1H, m), 4.09–4.29 (4H, m), 4.40–4.46 (1H, m), 5.94 (2H, s), 5.76 (1H, s), 5.78 (2H, d, J=14 Hz)

Preparation 34-2)

To a solution of (4S)-3-(3,4-methylenedioxyphenyl)-acetyl-4-isopropyloxazolidin-2-one (4.24 g) in tetrahydrofuran (80 ml) was added dropwise lithium bis(trimethylsilyl) amide (26.2 ml, 1.0M tetrahydrofuran solution) at −60° C. and the solution was stirred at 0° C. for 1 hour. A solution of 1-tert-butoxycarbonyl-2-n-butyl-4-(bromomethyl) imidazole (5.08 g) in tetrahydrofuran (50 ml) was added to the above mixture at −50~−40° C., and then the resulting mixture was stirred at −25~−20° C. for 4.5 hours. The reaction was quenched with saturated ammonium chloride aqueous solution and the solution was extracted with ethyl acetate. The organic layer was washed successively with saturated sodium bicarbonate aqueous solution and brine. Drying, filtering and removal of the solvents afforded a crude product. The crude product was purified by column chromatogaphy (eluent; n-hexane:ethyl acetate=4:1) to give (4S)-3-[3-(1-tert-butoxycarbonyl-2-n-butylimidazol-4-yl)-2-(3,4-methylenedioxyphenyl)propionyl]-4-isopropyloxazolidin-2-one (4.88 g) as a yellow oil.

NMR (CDCl$_3$, δ): 0.72–0.90 (6H, m), 0.95 (3H, t, J=8 Hz), 1.35–1.43 (2H, m), 1.59, 1.61 (total 9H, s), 1.60–1.70 (2H, m), 2.27–2.37 (1H, m), 2.80–2.95 (3H, m), 3.31–3.40 (1H, m), 4.10–4.40 (3H, m), 5.46 (1H, dd, J=6, 10 Hz), 5.92, 5.94 (total 2H, s), 6.71–6.96 (4H, m)

ESI-MS: 528 [M+H]

Preparation 34-3)

To a solution of benzyl alcohol (1.29 g) in tetrahydrofuran (60 ml) was added dropwise n-butyl lithium (6.6 ml, 1.6M n-hexane solution) at 2–8° C. and the mixture was stirred for 20 minutes. A solution of (4S)-3-[3-(1-tert-butoxycarbonyl-2-n-butylimidazol-4-yl)-2-(3,4-methylenedioxyphenyl) propionyl]-4-isopropyloxazolidin-2-one (4.86 g) was added dropwise to the mixture and the resulting solution was stirred at 2° C. for 2 hours. The reaction was quenched with saturated ammonium chloride aqueous solution, and then the solution was extracted with ethyl acetate. The organic layer was washed successively with saturated sodium bicarbonate aqueous solution and brine. Drying, filtering and removal of the solvents afforded a crude product. The crude product was purified by a silica gel column chromatography (eluent; n-hexane:ethyl acetate=4:1) to give benzyl 3-(1-tert-butoxycarbonyl-2-n-butylimidazol-4-yl)-2-(3,4-methylenedioxyphenyl)propionate (2R:2S=1:4) (3.67 g) as a slightly yellow oil.

NMR (CDCl$_3$, δ): 0.94 (3H, t, J=8 Hz), 1.35–1.43 (2H, m), 1.58 (9H, s), 1.62–1.71 (2H, m), 2.83–2.97 (3H, m), 3.20–3.30 (1H, m), 4.03–4.10 (1H, m), 5.00 (1H, d, J=14 Hz), 5.13 (1H, d, J=14 Hz), 5.94 (2H, s), 6.70–6.91 (4H, m), 7.17–7.38 (5H, m)

ESI-MS: 507 [M+H]

Preparation 34-4)

The mixture of benzyl (2RS)-3-(1-tert-butoxycarbonyl-2-n-butylimidazol-4-yl)-2-(3,4-methylenedioxyphenyl) propionate (2R:2S=1:4, 3.65 g) and 10% palladium on activated carbon (1.0 g) in methanol (50 ml) and water (5 ml) was shaken under hydrogen atmosphere (3 atmospheric pressure) at ambient temperature for 1 hour. The catalyst was filtered through a bed of celite and the filtrate was evaporated in vacuo. The residue was diluted with AcOEt (ethyl acetate) and the organic layer was washed with brine. Drying, filtering and removal of the solvents afforded (2RS)-3-(1-tert-butoxycarbonyl)-2-n-butylimidazol-4-yl)-2-(3,4-methylenedioxyphenyl)propionic acid (2R:2S=1:4) (2.63 g) as a white solid.

NMR (CDCl$_3$, δ): 0.90 (3H, t, J=8 Hz), 1.25–1.38 (2H, m), 1.56–1.68 (2H, m), 1.59 (9H, s), 2.86–2.95 (3H, s), 3.19–3.28 (1H, m), 3.93–3.99 (1H, m), 5.92 (2H, s), 6.70 (2H, s), 6.79 (1H, s), 6.96 (1H, s)

ESI-MS: 417 [M+H]

Preparation 35-1)

tert-Butoxycarbonyl-L-Trp(CH$_2$CH$_2$CO$_2$Et)-OH was obtained as a slightly yellow oil according to a similar manner to that of Preparation 29-1).

NMR (CDCl$_3$, δ): 1.20 (3H, t, J=7 Hz), 1.43 (9H, s), 2.88 (2H, t, J=7 Hz), 3.25–3.35 (2H, m), 4.10 (2H, q, J=7 Hz), 4.39 (2H, t, J=7 Hz), 4.58–4.66 (1H, br), 5.00–5.06 (1H, br), 7.00 (1H, s), 7.11 (1H, t, J=8 Hz), 7.22 (1H, t, J=8 Hz), 7.31 (1H, d, J=8 Hz), 7.58 (1H, d, J=8 Hz)

Preparation 35-2)

tert-Butoxycarbonyl-L-Trp(CH$_2$CH$_2$CO$_2$Et)-OBzl was obtained as a colorless oil according to a similar manner to that of Preparation 36-1).

NMR (CDCl$_3$, δ): 1.20 (3H, t, J=7 Hz), 1.44 (9H, s), 2.70 (2H, t, J=7 Hz), 3.23–3.28 (2H, m), 4.07–4.15 (2H, m), 4.32 (2H, t, J=7 Hz), 4.63–4.70 (1H, m), 5.02–5.13 (1H, m), 5.07 (1H, d, J=13 Hz), 5.13 (1H, d, J=13 Hz), 6.69 (1H, s), 7.09 (1H, t, J=8 Hz), 7.18–7.40 (7H, m), 7.52 (1H, d, J=8 Hz)

Preparation 35-3)

HCl.H-L-Trp (CH$_2$CH$_2$CO$_2$Et) -OBzl hydrochloride was obtained as a slightly yellow solid according to a similar manner to that of Preparation 25-2).

NMR (DMSO-d$_6$, δ): 1.12 (3H, t, J=8 Hz), 2.76 (2H, t, J=8 Hz), 3.20–3.34 (2H, m), 4.02 (2H, q, J=8 Hz), 4.28 (1H, t, J=8 Hz), 4.34 (2H, t, J=8 Hz), 5.05 (1H, d, J=13 Hz), 5.12 (1H, d, J=13 Hz), 7.05 (1H, t, J=8 Hz), 7.13–7.20 (4H, m), 7.30–7.36 (3H, m), 7.49 (1H, d, J=8 Hz), 7.53 (1H, d, J=8 Hz), 8.56–8.62 (2H, br s)

Preparation 36-1)

To a suspension of tert-butoxycarbonyl-L-Trp (CH$_2$CO$_2$Et)-OH (900 mg) and potassium carbonate (478 mg) in N,N-dimethylformamide (15 ml) was added benzyl bromide (395 mg) at ambient temperature and the mixture was stirred for 2 hours, then the resulting mixture was filtered. The filtrate was diluted with ethyl acetate followed by washing successively with 0.5N hydrochloric acid, saturated sodium bicarbonate aqueous solution and brine. Drying, filtering and removal of the solvents afforded tert-butoxycarbonyl-L-Trp(CH$_2$CO$_2$Et)-OBzl (1.15 g) as a brown oil.

NMR (CDCl$_3$, δ): 1.24 (3H, t, J=8 Hz), 1.42 (9H, s), 3.27–3.30 (2H, m), 4.28 (2H, q, J=8 Hz), 4.65–4.73 (3H, m), 5.02–5.17 (3H, m), 7.08–7.13 (1H, m), 7.18–7.35 (8H, m), 7.53 (1H, d, J=8 Hz)

Preparation 36-2)

To a solution of tert-butoxycarbonyl-L-Trp(CH$_2$CO$_2$Et)-OBzl (1.10 g) in ethyl acetate (4 ml) was added 4N hydrogen chloride in ethyl acetate (2.3 ml) and the solution was stirred at ambient temperature for 3 hours. The resulting suspension was diluted with n-hexane followed by filtration to give HCl.H-L-Trp(CH$_2$CO$_2$Et)-OBzl (696 mg) as a slightly brown solid.

NMR (DMSO-d$_6$, δ): 1.21 (3H, t, J=8 Hz), 3.20–3.40 (2H, m), 4.13 (2H, q, J=8 Hz), 4.23–4.32 (1H, br s), 5.03 (2H, s), 5.04 (1H, d, J=14 Hz), 5.13 (1H, d, J=14 Hz), 7.07 (1H, t, J=8 Hz), 7.12–7.20 (4H, m), 7.29–7.36 (3H, m), 7.39 (1H, d, J=8 Hz), 7.56 (1H, d, J=8 Hz), 8.56–8.64 (2H, br s)

Preparation 37-1)

tert-Butoxycarbonyl-L-Trp(Me)-OBzl was obtained as a colorless oil according to a similar manner to that of Preparation 36-1).

NMR (CDCl$_3$, δ): 1.42 (9H, s), 3.28 (2H, d, J=4 Hz), 3.65 (3H, s), 4.65–4.72 (1H, m), 5.05 (1H, d, J=14 Hz), 5.14 (1H, d, J=14 Hz), 6.58 (1H, s), 7.09 (1H, t, J=8 Hz), 7.18–7.35 (6H, m), 7.52 (1H, d, J=8 Hz), 8.01 (1H, s)

Preparation 37-2)

HCl.H-L-Trp(Me)-OBzl was obtained as a white solid according to a similar manner to that of Preparation 25-2).

NMR (DMSO-d$_6$, δ): 3.20–3.38 (2H, m), 3.69 (3H, s), 4.22–4.29 (1H, br), 5.06 (1H, d, J=12 Hz), 5.10 (1H, d, J=12 Hz), 7.00–7.21 (5H, m), 7.29–7.36 (3H, m), 7.40 (1H, d, J=8 Hz), 7.54 (1H, d, J=8 Hz), 8.57–8.64 (2H, br s)

Preparation 38-1)

tert-Butoxycarbonyl-L-Trp(CH$_2$CO$_2$Bzl)-OBzl was obtained as a slightly yellow oil according to a similar manner to that of Preparation 36-1).

NMR (CDCl$_3$, δ): 1.43 (9H, s), 3.26–3.29 (2H, br), 4.65–4.72 (3H, br s), 4.99–5.16 (4H, m), 6.55 (1H, s), 7.08–7.38 (14H, m), 7.53 (1H, d, J=8 Hz)

Preparation 38-2)

HCl.H-L-Trp(CH$_2$CO$_2$Bzl)-OBzl was obtained as a slightly yellow solid according to a similar manner to that of Preparation 25-2).

NMR (DMSO-d$_6$, δ) 3.20–3.32 (2H, m), 4.26–4.33 (1H, m), 5.02 (1H, d, J=13 Hz), 5.09–5.18 (5H, m), 7.07 (1H, t, J=8 Hz), 7.13–7.20 (4H, m), 7.29–7.34 (9H, m), 7.56 (1H, d, J=8 Hz), 8.52–8.60 (2H, br s)

ESI-MS: 443 [M+H]

Preparation 39-1)

tert-Butoxycarbonyl-L-Trp(Et)-OBzl was obtained as a slightly yellow oil according to a similar manner to that of Preparation 35-1) by using ethyl iodide and to that of Preparation 36-1).

NMR (CDCl$_3$, δ): 1.37 (3H, t, J=8 Hz), 1.40 (9H, s), 3.28 (2H, d, J=6 Hz), 4.02 (2H, q, J=8 Hz), 4.65–4.72 (1H, m), 5.06 (1H, d, J=11 Hz), 5.14 (1H, d, J=11 Hz), 7.08 (1H, t, J=8 Hz), 7.16–7.36 (9H, m), 7.53 (1H, d, J=8 Hz)

Preparation 39-2)

HCl.H-L-Trp(Et)-OBzl was obtained as a white solid according to a similar manner to that of Preparation 25-2).

NMR (DMSO-d$_6$, δ): 1.30 (3H, t, J=8 Hz), 3.20–3.36 (2H, m), 4.10 (2H, q, J=8 Hz), 4.28 (1H, t, J=7 Hz), 5.07 (1H, d, J=11 Hz), 5.13 (1H, d, J=11 Hz), 7.04 (1H, t, J=8 Hz), 7.12–7.20 (4H, m), 7.30–7.35 (3H, m), 7.47 (1H, d, J=9 Hz), 7.54 (1H, d, J=9 Hz), 8.52–8.58 (2H, br s)

Preparation 40-1)

Ethyl 3-(1-tert-butoxycarbonylimidazol-4-yl)-3-hydroxy-2-(3,4-methylenedioxyphenyl)propionate was obtained as a yellow amorphous powder according to a similar manner to that of Preparation 8-2).

NMR (CDCl$_3$, δ): 1.14–1.28 (3H, m), 1.59, 1.60 (total 9H, s), 2.94 (0.5H, d, J=4 Hz), 3.55 (0.5H, d, J=8 Hz), 4.04–4.21 (3H, m), 5.06 (0.5H, t, J=8 Hz), 5.26 (0.5H, dd, J=4, 8 Hz), 5.92 (0.5H, s), 5.95 (0.5H, s), 6.68–6.78 (2H, m), 6.84 (0.5H, d, J=2 Hz), 6.88 (0.5H, s), 7.07 (0.5H, s), 7.21 (0.5H, s), 7.97 (0.5H, s), 8.03 (0.5H, s)

ESI-MS 405 [M+H]

Preparation 40-2)

Ethyl (E and Z)-3-(1-tert-butoxycarbonylimidazol-4-yl)-2-(3,4-methylenedioxyphenyl)-2-propenoate was obtained as a white solid according to a similar manner to that of Preparation 31-1).

Less Polar Diastereomer

NMR (CDCl$_3$, δ): 1.36 (3H, t, J=7 Hz), 1.62 (9H, s), 4.40 (2H, q, J=7 Hz), 5.98 (2H, s), 6.72 (1H, s), 6.80 (1H, d, J=8 Hz), 6.94 (1H, d, J=8 Hz), 6.98 (1H, s), 7.48 (1H, s), 8.03 (1H, s)

ESI-MS: 387 [M+H]

More Polar Diastereomer

NMR (CDCl$_3$, δ): 1.30 (3H, t, J=8 Hz), 1.56 (9H, s), 4.24 (2H, q, J=8 Hz), 6.00 (2H, s), 6.52 (1H, s), 6.69–6.73 (2H, m), 6.89 (1H, d, J=8 Hz), 7.79 (1H, s), 7.98 (1H, s)

ESI-MS: 387 [M+H]

Preparation 40-3)

Ethyl 3-(1-tert-butoxycarbonylimidazol-4-yl)-2-(3,4-methylenedioxyphenyl)propionate was obtained as a yellow oil according to a similar manner to that of Preparation 16-6).

NMR (CDCl$_3$, δ): 1.18 (3H, t, J=8 Hz), 1.59 (9H, s), 2.90 (1H, dd, J=7, 15 Hz), 3.28 (1H, dd, J=9, 15 Hz), 3.88 (1H, dd, J=7, 9 Hz), 4.02–4.17 (2H, m), 5.94 (2H, s), 6.73 (1H, d, J=8 Hz), 6.78 (1H, d, J=8 Hz), 6.86 (1H, s), 7.01 (1H, s), 7.97 (1H, s)

ESI-MS: 389 [M+H]

Preparation 40-4)

A solution of ethyl 3-(1-tert-butoxycarbonylimidazol-4-yl)-2-(3,4-methylenedioxyphenyl)propionate (633 mg) in trifluoroacetic acid (5 ml) was stirred at ambient temperature for 10 minutes. Trifluoroacetic acid was removed by evaporation and the residue was diluted with ethyl acetate followed by washing successively with saturated sodium bicarbonate aqueous solution and brine. Drying, filtering and removal of the solvents afforded a crude intermediate compound. To a solution of the above compound and triethylamine (214 mg) in dichloromethane (10 ml) was added portionwise triphenylmethyl chloride (545 mg) and the mixture was stirred at ambient temperature for 20 minutes. The resulting solution was washed successively with saturated ammonium chloride aqueous solution and saturated sodium bicarbonate aqueous solution. Drying, filtering and removal of the solvents afforded ethyl 3-[1-(triphenylmethyl)imidazol-4-yl]-2-(3,4-methylenedioxyphenyl)propionate (740 mg) as a slightly yellow oil.

NMR (CDCl$_3$, δ): 1.15 (3H, t, J=8 Hz), 2.90 (1H, dd, J=8, 14 Hz), 3.25 (1H, dd, J=7, 14 Hz), 3.92 (1H, dd, J=7, 8 Hz), 3.99–4.14 (2H, m), 5.92 (2H, s), 6.33 (1H, s), 6.70 (2H, s), 6.81 (1H, s), 7.00–7.05 (6H, m), 7.25–7.32 (10H, m)

Preparation 40-5)

The mixture of ethyl 3-[1-(triphenylmethyl)imidazol-4-yl]-2-(3,4-methylenedioxyphenyl)propionate (730 mg) in 1N sodium hydroxide aqueous solution (4.1 ml) and ethanol (10 ml) was stirred at ambient temperature for 3 hours. The resulting solution was neutralized with 1N hydrochloric acid (4 ml) followed by dilution with ethyl acetate, and then the organic layer was washed with brine. Drying, filtering and removal of the solvents afforded 3-[1-(triphenylmethyl)-imidazol-4-yl]-2-(3,4-methylenedioxyphenyl)propionic acid (650 mg) as a white solid.

Rf: 0.19 (10% methanol in chloroform)

Preparation 41-1)

Methyl 3-[1-(triphenylmethyl)imidazol-4-yl]-2-(3,4-methylenedioxyphenyl)propionate was obtained as a white powder according to a similar manner to that of Example 30-2).

NMR (CDCl$_3$, δ): 2.93 (1H, dd, J=7, 15 Hz), 3.25 (1H, dd, J=8, 15 Hz), 3.59 (3H, s), 3.96 (1H, dd, J=7, 8 Hz), 5.93 (2H, s), 6.34 (1H, s), 6.70 (2H, s), 6.80 (1H, s), 7.00–7.06 (5H, m), 7.26–7.36 (11H, m)

ESI-MS: 517 [M+H]

Preparation 41-2)

To a solution of methyl 3-[1-(triphenylmethyl)imidazol-4-yl]-2-(3,4-methylenedioxyphenyl)propionate (430 mg) in acetonitrile (30 ml) was added methyl iodide (708 mg) and the mixture was stirred at ambient temperature for 60 hours. Removal of the solvents gave an iodonium salt. A mixture of the above iodonium salt in 80% acetic acid-water (10 ml) was stirred at 60° C. for 1.5 hours. The resulting mixture was cooled to ambient temperature and the solution was diluted with water. Carbinol was removed by filtration and the filtrate was neutralized with saturated sodium bicarbonate aqueous solution. The aqueous layer was extracted with ethyl acetate and the organic layer was washed with saturated sodium bicarbonate aqueous solution. Drying, filtering and removal of the solvents afforded a crude product. The crude product was chromatographed on silica gel (eluent; 3% methanol in chloroform) to give methyl 3-(1-methylimidazol-5-yl)-2-(3,4-methylenedioxyphenyl) propionate (176 mg) as a colorless oil.

NMR (CDCl$_3$, δ): 2.90 (1H, dd, J=7, 15 Hz), 3.29 (1H, dd, J=9, 15 Hz), 3.48 (3H, s), 3.65 (1H, s), 3.79 (1H, dd, J=7, 9 Hz), 5.96 (2H, s), 6.73–6.77 (3H, m), 6.82 (1H, s), 7.33 (1H, s)

ESI-MS: 289 [M+H]

Preparation 41-3)

3-(1-Methylimidazol-5-yl)-2-(3,4-methylenedioxyphenyl)propionic acid was obtained as a slightly yellow powder according to a similar manner to that of Preparation 40-5).

NMR (DMSO-d$_6$, δ): 2.75 (1H, dd, J=7, 15 Hz), 3.13 (1H, dd, J=8, 15 Hz), 3.48 (3H, s), 3.64 (1H, dd, J=7, 8 Hz), 5.96 (2H, s), 6.52 (1H, s), 6.76 (1H, d, J=8 Hz), 6.79 (1H, d, J=8 Hz), 6.92 (1H, s), 7.39 (1H, s)

ESI-MS: 275 [M+H]

Preparation 42-1)

1-t-Butoxycarbonyl-2-ethyl-4-(hydroxymethyl)imidazole was obtained according to a similar manner to that of Preparation 33-1).

NMR (CDCl$_3$, δ): 1.30 (3H, t, J=7 Hz), 1.10 (9H, s), 3.00 (2H, q, J=8 Hz), 3.08–3.22 (1H, m), 4.54 (2H, s), 7.24 (1H, s)

ESI-MS (m/z): 227 [M+H]

Preparation 42-2)

1-t-Butoxycarbonyl-2-ethyl-4-(bromomethyl)imidazole was obtained according to a similar manner to that of Preparation 33-2).

NMR (CDCl$_3$, δ) 1.31 (3H, t, J=7 Hz), 1.60 (9H, s), 3.00 (2H, q, J=6 Hz), 4.39 (2H, s), 7.33 (1H, s)

Preparation 42-3)

(4S)-3-[3-(1-t-Butoxycarbonyl-2-ethylimidazol-4-yl)-2-(3,4-methylenedioxyphenyl)propionyl]-4-isopropyloxazolidinone was obtained according to a similar manner to that of Preparation 34-2).

NMR (CDCl$_3$, δ): 0.72 (3H, d, J=7 Hz), 0.85 (3H, d, J=7 Hz), 1.24–1.29 (3H, m), 1.58 (4.5H, s), 1.65 (4.5H, s), 2.25–2.37 (1H, m), 2.81–2.98 (3H, m), 3.33–3.41 (1H, m), 4.08–4.15 (2H, m), 4.33–4.38 (1H, m), 5.43–5.50 (1H, m), 5.91 (2H, s), 6.73 (1H, d, J=7 Hz), 6.88–6.97 (3H, m)

ESI-MS (m/z): 500 [M+H]

Preparation 42-4)

Benzyl 3-(1-t-butoxycarbonyl-2-ethylimidazol-4-yl)-2-(3,4-methylenedioxyphenyl)propionate was obtained according to a similar manner to that of Preparation 34-3).

NMR (CDCl$_3$, δ): 1.27 (3H, t, J=7 Hz), 1.57 (4.5H, s), 1.63 (4.5H, s), 2.82–2.98 (3H, m), 3.21–3.30 (1H, m), 4.02–4.15 (1H, m), 4.98–5.16 (2H, m), 5.92 (2H, s), 6.70–6.90 (4H, m), 7.15–7.27 (4H, m), 7.37 (1H, d, J=6 Hz)

ESI-MS (m/z): 479 [M+H]

Preparation 42-5)

3-(1-t-Butoxycarbonyl-2-ethylimidazol-4-yl)-2-(3,4-methylenedioxyphenyl)propionic acid was obtained according to a similar manner to that of Preparation 16-6).

NMR (CDCl$_3$, δ): 1.21 (3H, t, J=7 Hz), 1.68 (9H, s), 2.82–2.97 (3H, m), 3.18–3.28 (1H, m), 3.90–3.98 (1H, m), 5.90 (2H, s), 6.69 (2H, s), 6.79 (1H, s), 6.96 (1H, s)

ESI-MS (m/z): 389 [M+H]

Preparation 43-1)

1-tert-Butoxycarbonyl-2-n-propyl-4-bromomethylimidazole was obtained as a slightly yellow oil according to a similar manner to that of Preparation 33-2).

NMR (CDCl$_3$, δ): 1.00 (3H, t, J=8 Hz), 1.60, 1.63 (total 9H, s), 1.67–1.81 (2H, m), 2.96 (2H, dd, J=8, 9 Hz), 4.39 (2H, s), 7.33 (1H, s)

Preparation 43-2)

(4S)-3-[3-(1-tert-Butoxycarbonyl-2-n-propylimidazol-4-yl)-2-(3,4-methylenedioxyphenyl)propionyl]-4- isopropyloxazolidin-2-one was obtained as a yellow oil according to a similar manner to that of Preparation 34-2).

NMR (CDCl$_3$, δ): 0.70–1.00 (6H, m), 0.98 (3H, t, J=8 Hz), 1.58, 1.61 (total 9H, s), 1.66–1.77 (2H, m), 2.26–2.36 (1H, m), 2.82–2.93 (3H, m), 3.32–3.40 (1H, m), 4.08–4.40 (4H, m), 5.47 (1H, dd, J=4, 9 Hz), 5.92, 5.95 (total 2H, s), 6.74 (1H, t, J=8 Hz), 6.87–6.96 (2H, m)

ESI-MS: 514 [M+H]

Preparation 43-3)

Benzyl (2RS)-3-(1-tert-butoxycarbonyl-2-n-propylimidazol-4-yl)-2-(3,4-methylenedioxyphenyl) propionate (2R:2S=1:4) was obtained as a slightly yellow oil according to a similar manner to that of Preparation 34-3).

NMR (CDCl$_3$, δ): 0.98 (3H, t, J=8 Hz), 1.58, 1.62 (total 9H, s), 1.66–1.74 (2H, m), 2.85–2.94 (2H, m), 3.20–3.29 (1H, m), 4.04–4.10 (1H, m), 5.01 (1H, d, J=12 Hz), 5.14 (1H, d, J=12 Hz), 5.94 (2H, s), 6.70–6.81 (2H, m), 6.84–6.91 (1H, m), 7.16–7.20 (1H, m), 7.25–7.39 (6H, m)

ESI-MS: 493 [M+H]

Preparation 43-4)

(2RS)-3-(1-tert-Butoxycarbonyl-2-n-propylimidazol-4-yl)-2-(3,4-methylenedioxyphenyl)propionic acid (2R:2S= 1:4) was obtained as a white solid according to a similar manner to that of Preparation 16-6).

mp: 129–132° C.

NMR (CDCl$_3$, δ): 0.94 (3H, t, J=9 Hz), 1.57 (9H, s), 1.62–1.73 (2H, m), 2.85–2.95 (3H, br), 3.18–3.29 (1H, m), 3.89–3.97 (1H, br), 5.88–5.92 (2H, br s), 6.68–6.73 (2H, br s), 6.80 (1H, s), 6.94–6.98 (1H, br s)

ESI-MS: 403 [M+H]

Preparation 44-1)

1-t-Butoxycarbonyl-2-pentyl-4-(hydroxymethyl) imidazole was obtained according to a similar manner to that of Preparation 33-1).

NMR (CDCl$_{3, δ}$): 0.89 (3H, t, J=7 Hz), 1.27–1.42 (4H, m), 1.60 (9H, s), 1.65–1.78 (2H, m), 2.42 (1H, t, J=6 Hz), 2.98 (2H, t, J=7 Hz), 4.53 (2H, d, J=6 Hz), 7.24 (1H, d, J=6 Hz)

ESI-MS (m/z): 269 [M+H]

Preparation 44-2)

1-t-Butoxycarbonyl-2-pentyl-4-(bromomethyl)imidazole was obtained according to a similar manner to that of Preparation 33-2).

Rf: 0.53 (hexane:ethyl acetate=4:1)

Preparation 44-3)

(4S)-3-[3-(1-t-Butoxycarbonyl-2-pentylimidazol-4-yl)-2-(3,4-methylenedioxyphenyl)propionyl]-4-isopropyloxazolidin-2-one was obtained according to a similar manner to that of Preparation 34-2).

NMR (CDCl$_3$, δ): 0.72–0.93 (9H, m), 1.30–1.40 (4H, m), 1.55–1.61 (9H, m), 1.62–1.80 (2H, m), 2.25–2.38 (1H, m), 2.81–2.95 (3H, m), 3.32–3.40 (1H, m), 4.08–4.38 (3H, m), 5.42–5.48 (1H, m), 5.91–5.93 (2H, m), 6.70–6.97 (4H, m)

ESI-MS (m/z): 542 [M+H]

Preparation 44-4)

Benzyl 3-(1-t-butoxycarbonyl-2-pentylimidazol-4-yl)-2-(3,4-methylenedioxyphenyl)propionate was obtained according to a similar manner to that of Preparation 34-3).

NMR (CDCl$_3$, δ): 0.86–0.91 (3H, m), 1.27–1.36 (4H, m), 1.57 (9H, s), 1.57–1.75 (2H, m), 2.82–2.92 (3H, m), 3.19–3.28 (1H, m), 4.02–4.12 (1H, m), 4.97–5.15 (2H, m), 5.93 (2H, s), 6.70–6.90 (4H, m), 7.15–7.35 (5H, m)

ESI-MS (m/z): 521 [M+H]

Preparation 44-5)

3-(1-t-Butoxycarbonyl-2-pentylimidazol-4-yl)-2-(3,4-methylenedioxyphenyl)propionic acid was obtained according to a similar manner to that of Preparation 16-6).

NMR (CDCl$_3$, δ): 0.87–0.92 (3H, m), 1.28–1.35 (4H, m), 1.57 (9H, s), 1.60–1.73 (2H, m), 2.89–2.95 (3H, m), 3.18–3.27 (1H, m), 3.95–4.00 (1H, m), 5.91 (2H, s), 6.70 (2H, s), 6.78 (1H, s), 6.95 (1H, s)

ESI-MS (m/z): 431 [M+H]

Example 1-1)

To a solution of (2RS,3RS)-2-(2-benzyloxyphenylmethyl)-3-cyclohexyl-3-hydroxypropionic acid (111 mg) in dimethylformamide (3 ml) were added L-tryptophan benzyl ester hydrochloride (198 mg), 1-hydroxybenzotriazole hydrate (60.8 mg), 1,3-dicyclohexylcarbodiimide (80.5 mg) and 4-methylmorpholine (91 mg) successively. After being stirred for 16 hours at ambient temperature, the mixture was poured into a mixture of diethyl ether and aqueous 1N hydrochloric acid solution. The organic layer was separated and the aqueous layer was extracted with diethyl ether. The combined organic layer was washed with aqueous bicarbonate solution and brine, dried and evaporated under reduced pressure. The residue was purified by chromatography to afford N-[(2RS,3RS)-2-(2-benzyloxyphenylmethyl)-3-cyclohexyl-3 hydroxypropionyl]-L-tryptophan benzyl ester (171 mg).

NMR (CDCl$_3$, δ): 0.60–2.00 (12H, m), 2.68–3.47 (6H, m), 4.81–5.06 (5H, m), 6.12–7.83 (21H, m)

The following compounds were obtained in substantially the same manner as that of Example 1-1).

Example 1-2)

N-[(2RS,3SR)-2-(2-Benzyloxyphenylmethyl)-3-cyclohexyl-3-hydroxypropionyl]-L-tryptophan Benzyl Ester NMR (CDCl$_3$, δ): 0.57–2.03 (12H, m), 2.63–3.46 (6H, m), 4.61–5.06 (5H, m), 5.82–7.91 (21H, m)

Example 2-1)

N-[(2RS,3SR)-2-(2-Benzyloxyphenyl)-3-cyclohexyl-3-hydroxypropionyl]-L-tryptophan Benzyl Ester NMR (CDCl$_3$, δ): 0.85–1.80 (10H, m), 1.95–2.10 (1H, m), 3.12–3.20 (2H, m), 3.96–4.25 (3H, m), 4.69–5.04 (5H, m), 6.02 (0.5H, d, J=2.4 Hz), 6.43 (1H, d, J=7.4 Hz), 6.52 (0.5H, d, J=2.4 Hz), 6.80–7.41 (18H, m), 7.56 (0.5H, s), 7.67 (0.5H, s), 7.83–7.94 (1H, m)

Example 2-2)

N-[(2RS,3RS)-2-(2-Benzyloxyphenyl)-3-cyclohexyl-3-hydroxypropionyl]-L-tryptophan Benzyl Ester NMR (CDCl$_3$, δ): 0.80–1.75 (11H, m), 3.13–3.22 (2H, m), 3.96–4.11 (3H, m), 4.78–5.04 (5H, m), 6.16 (0.5H, d, J=2.4 Hz), 6.30 (0.5H, d, J=6.1 Hz), 6.33 (0.5H, d, J=7.3 Hz), 6.63 (0.5H, d, J=2.4 Hz), 6.79–7.48 (18H, m), 7.65 (0.5H, s), 7.75 (0.5H, s)

Example 3-1)

N-[(2RS,3SR)-4-(2-Benzyloxyphenyl)-2-{1-cyclohexyl-1-(hydroxy)methyl}butyryl]-L-tryptophan Benzyl Ester NMR (CDCl₃, δ): 0.80–1.80 (11H, m), 1.80–2.10 (2H, m), 2.10–2.25 (1H, m), 2.51–2.63 (2H, m), 3.23–3.55 (4H, m), 4.93–5.18 (5H, m), 6.32 (0.5H, d, J=8.2 Hz), 6.40 (0.5H, d, J=8.0 Hz), 6.73–7.54 (18H, m), 7.81 (0.5H, s), 7.93 (0.5H, s)

Example 3-2)

N-[(2RS,3RS)-4-(2-Benzyloxyphenyl)-2-{1-cyclohexyl-1-(hydroxy)methyl}butyryl]-L-tryptophan Benzyl Ester NMR (CDCl₃, δ): 0.80–2.10 (13H, m), 2.20–2.35 (1H, m), 2.54–2.80 (2H, m), 3.01–3.08 (1H, m), 3.21–3.31 (3H, m), 4.93–5.10 (5H, m), 6.26 (0.5H, d, J=8.0 Hz), 6.40 (0.5H, d, J=8.2 Hz), 6.80–7.54 (18H, m), 7.83 (0.5H, s), 7.92 (0.5H, s)

Example 4

N-[(2RS,3SR)-3-Cyclohexyl-3-hydroxy-2-(2-methoxyphenylmethyl)propionyl]-L-tryptophan Benzyl Ester NMR (CDCl₃, δ): 0.70–1.80 (10H, m), 2.05–2.11 (1H, m), 2.67–3.26 (4H, m), 3.52–3.60 (1H, m), 3.61 (1.5H, s), 3.76 (1.5H, s), 3.98 (0.5H, d, J=1.7 Hz), 4.14 (0.5H, d, J=2 Hz), 4.62–4.90 (1H, m), 4.97–5.01 (3H, m), 5.97 (0.5H, d, J=8.0 Hz), 6.09 (0.5H, d, J=8.0 Hz), 6.26–7.57 (14H, m), 7.90 (0.5H, s), 7.99 (0.5H, s)

Example 5

N-[2-(2-Benzyloxycarbonylphenylmethyl)-3-cyclohexyl-3-hydroxypropionyl]-L-tryptophan Benzyl Ester NMR (CDCl₃, δ): 0.80–1.80 (11H, m), 1.85–2.05 (1H, m), 2.71–2.81 (1H, m), 2.96–3.52 (5H, m), 3.80 (0.5H, d, J=3.1 Hz), 4.00 (0.5H, d, J=3.0 Hz), 4.68–4.74 (1H, m), 4.98 (2H, s), 5.19 (1H, s), 5.31 (1H, dd, J=12.3 and 18.6 Hz), 6.02 (0.5H, d, J=7.9 Hz), 6.32 (0.5H, d, J=2.4 Hz), 6.49 (0.5H, d, J=7.6 Hz), 6.66 (0.5H, d, J=2.3 Hz), 7.02–7.46 (16H, m), 7.70 (0.5H, s), 7.75 (0.5H, d, J=7.5 Hz), 7.84 (0.5H, d, J=7.5 Hz), 7.89 (0.5H, s)

Example 6-1)

N-[(2S,3S)-2-(2-Benzyloxyphenyl)-3-cyclohexyl-3-hydroxypropionyl]-L-tryptophan Benzyl Ester NMR (CDCl₃, δ): 0.80–1.75 (11H, m), 3.12–3.16 (2H, m), 3.95–4.15 (3H, m), 4.79 (2H, s), 4.85–4.98 (1H, m), 5.04 (2H, s), 6.18 (1H, d, J=2.4 Hz), 6.29 (1H, d, J=7.6 Hz), 6.81–7.37 (20H, m), 7.65 (1H, s)

[a]$_D^{24}$: −35.4° (C=0.56, CH₂Cl₂)

Example 6-2)

N-[(2R,3R)-2-(2-Benzyloxyphenyl)-3-cyclohexyl-3-hydroxypropionyl]-L-tryptophan Benzyl Ester NMR (CDCl₃, δ): 0.80–1.40 (5H, m), 1.40–1.75 (6H, m), 3.20 (2H, d, J=5.7 Hz), 4.08–4.14 (3H, m), 4.79–5.04 (5H, m), 6.32 (1H, d, J=7.9 Hz), 6.63 (1H, d, J=2.4 Hz), 6.79–7.48 (20H, m), 7.74 (1H, s)

[a]$_D^{24}$ 27.8° (C=0.56, CH₂Cl₂)

Example 6-3)

N-[(2R,3R)-2-(2-Benzyloxyphenyl)-3-cyclohexyl-3-hydroxypropionyl]-1-methyl-L-tryptophan Benzyl Ester NMR (CDCl₃, δ): 0.9–1.80 (11H, m), 3.19 (2H, d, J=5.6 Hz), 3.55 (1H, s), 4.05 (2H, s), 4.20 (1H, s), 4.71–5.02 (6H, m), 6.30 (1H, d, J=8.0 Hz), 6.44 (1H, s), 6.78–7.46 (17H, m)

[α]$_D^{30}$: 17.4° (C=0.88, CH₂Cl₂)

Example 7-1)

To a solution of N-[(2RS,3RS)-2-(2-benzyloxyphenylmethyl)-3-cyclohexyl-3-hydroxypropionyl]-L-tryptophan benzyl ester (150 mg) in methanol (3 ml) was added 10% palladium on carbon (45 mg) and the mixture was stirred under hydrogen atmosphere for 3 hours. The mixture was filtered and the filtrate was evaporated under reduced pressure to give N-[(2RS,3RS)-3-cyclohexyl-3-hydroxy-2-(2-hydroxyphenylmethyl)propionyl]-L-tryptophan (128 mg).

NMR (CD₃OD, δ): 0.77–1.80 (11H, m), 2.65–3.51 (6H, m), 4.56–4.64 (1H, m), 6.54–7.56 (10H, m)

The following compounds were obtained in substantially the same manner as that of Example 7-1).

Example 7-2)

N-[(2RS,3SR)-3-Cyclohexyl-3-hydroxy-2-(2-hydroxyphenylmethyl)propionyl]-L-tryptophan NMR (CD₃OD, δ): 0.75–2.00 (12H, m), 2.60–3.76 (6H, m), 4.64–4.77 (1H, m), 6.53–7.62 (10H, m)

Example 8-1)

N-[(2RS,3SR)-3-Cyclohexyl-3-hydroxy-2-(2-hydroxyphenyl)propionyl]-L-tryptophan

NMR (CD₃OD, δ): 0.85–1.95 (11H, m), 3.18–3.25 (2H, m), 3.93–4.30 (3H, m), 4.50–4.71 (1H, m), 6.69–7.59 (10H, m)

Example 8-2)

N-[(2RS,3RS)-3-Cyclohexyl-3-hydroxy-2-(2-hydroxyphenyl)propionyl]-L-tryptophan

NMR (CD₃OD, δ): 0.80–1.90 (11H, m), 3.17–3.23 (2H, m), 3.83–4.15 (3H, m), 4.69–4.81 (1H, m), 6.62–7.61 (10H, m)

Example 9-1)

N-[(2RS,3SR)-4-(2-Hydroxyphenyl)-2-{1-cyclohexyl-1-(hydroxy)methyl}butyryl]-L-tryptophan NMR (CD₃OD, δ): 0.80–2.20 (11H, m), 2.20–2.70 (3H, m), 3.18–3.39 (5H, m), 5.00–5.04 (1H, m), 6.65–7.61 (10H, m)

Example 9-2)

N-[(2RS,3RS)-4-(2-Benzyloxyphenyl)-2-{1-cyclohexyl-1-(hydroxy)methyl}butyryl]-L-tryptophan NMR (CDCl₃, δ): 0.80–2.00 (11H, m), 2.20–2.66 (3H, m), 4.75–4.85 (1H, m), 6.61–7.84 (10H, m)

Example 10

N-[(2RS,3SR)-3-Cyclohexyl-3-hydroxy-2-(2-methoxyphenylmethyl)propionyl]-L-tryptophan NMR (CD₃OD, δ): 0.80–1.90 (11H, m), 2.54–3.54 (6H, m), 3.70 (1.5H, s), 3.72 (1.5H, s), 4.48–4.61 (1H, m), 6.52–7.55 (10H, m)

Example 11

N-[2-(2-Carboxyphenylmethyl)-3-cyclohexyl-3-hydroxypropionyl]-L-tryptophan

NMR (CD₃OD, δ): 0.80–2.00 (11H, m), 2.84–3.09 (3H, m), 3.22–3.68 (3H, m), 4.49–4.62 (1H, m), 6.65–7.85 (10H, m)

Example 12-1)

N-[(2S,3S)-3-Cyclohexyl-2-(2-hydroxyphenyl)-3-hydroxypropionyl]-L-tryptophan

NMR (CD₃OD, δ): 0.80–1.80 (11H, m), 3.10–3.22 (2H, m), 4.01–4.11 (2H, m), 4.77 (1H, t, J=6.3 Hz), 6.62 (1H, s), 6.76–7.27 (8H, m), 7.40 (1H, d, J=7.8 Hz)

[α]$_D^{24}$: 6.0° (C=0.25, CH₃OH)

Example 12-2)

N-[(2R,3R)-3-Cyclohexyl-2-(2-hydroxyphenyl)-3-hydroxypropionyl]-L-tryptophan

NMR (CD₃OD, δ): 0.80–1.80 (11H, m), 3.17–3.50 (2H, m), 3.97–4.11 (2H, m), 4.72 (1H, t, J=6.9 Hz), 6.64–6.78 (2H, m), 6.94–7.11 (6H, m), 7.31 (1H, d, J=7.6 Hz), 7.58 (1H, d, J=7.9 Hz)

[α]$_D^{25}$: 28.5° (C=0.2, CH₃OH)

Example 12-3)

N-[(2R,3R)-3-Cyclohexyl-2-(2-hydroxyphenyl)-3-hydroxypropionyl]-1-methyl-L-tryptophan NMR (CD₃OD, δ): 0.80–1.80 (11H, m), 3.15–3.37 (2H, m), 3.67 (3H, s), 3.98 (1H, d, J=8.4 Hz), 4.12 (1H, d, J=6.6 Hz), 4.67 (1H, t, J=6.6 Hz), 6.65–7.17 (6H, m), 7.22 (1H, d, J=8.0 Hz), 7.59 (1H, d, J=7.7 Hz)

[α]$_D^{29}$: 27.5° (C=0.20, CH₃OH)

Example 13-1)

To a solution of (2RS,3RS)-2-(3,4-methylenedioxyphenyl)-3-cyclohexyl-3-hydroxypropionic acid (100 mg), HCl.H-L-Trp-OMe (136 mg) and HOBT (55 mg) in dimethylformamide (6 ml) was added WSCD (64 mg) under ice-bath cooling. After being stirred overnight at room temperature, the mixture was poured into water (20 ml) and extracted with ethyl acetate (20 ml). The organic layer was washed with 5% hydrochloric acid solution, 1M aqueous sodium bicarbonate solution and brine, dried over magnesium sulfate, and concentrated in vacuo to afford N-[(2RS,3RS)-2-(3,4-methylenedioxyphenyl)-3-cyclohexyl-3-hydroxypropionyl]-L-tryptophane methyl ester (165 mg).

NMR (CDCl₃, δ) 0.95–1.76 (11H, m), 3.20 (1H, t, J=4 Hz), 3.28 (1H, t, J=4 Hz), 3.42 (1H, d, J=8 Hz), 3.62, 3.69 (1H, s), 3.75–3.92 (1H, m), 4.80–4.98 (1H, m), 5.92 (1H, s), 5.97 (1H, s), 6.07–6.18 (1H, m), 6.52–6.91 (4H, m), 7.00–7.22 (2H, m), 7.30–7.50 (2H, m), 7.95–8.10 (1H, m)

FAB MS m/z: 493 [M+H]⁺

The following compounds were obtained in substantially the same manner as that of Example 13-1).

Example 13-2)

N-[(2RS,3RS)-2-(3,4-Methylenedioxyphenyl)-3-cyclohexyl-3-hydroxypropionyl]-L-1-naphthylalanine Benzyl Ester (170 mg)

NMR (CDCl₃, δ): 0.87–1.72 (11H, m), 3.33–3.60 (3H, m), 3.65–3.75 (1H, m), 3.75–3.85 (1H, m), 4.90–5.09 (3H, m), 5.90–6.00 (2H, m), 6.08 (1H, d, J=8 Hz), 6.45–6.70 (3H, m), 6.85–7.35 (7H, m), 7.40–7.55 (2H, m), 7.70 (1H, t, J=8 Hz), 7.80–7.90 (1H, m), 7.95–8.05 (1H, m)

FAB MS m/z: 580 [M+H]⁺

Example 13-3)

N-[(2R,3R)-2-(3,4-Methylenedioxyphenyl)-3-cyclohexyl-3-hydroxypropionyl]-L-2-naphthylalanine ethyl ester (129 mg)

NMR (CDCl₃, δ): 0.98–1.70 (14H, m), 3.21, 3.29 (1H, dd, J=8, 8 Hz), 3.45 (1H, d, J=8 Hz), 3.78 (1H, d, J=6 Hz), 3.85 (1H, m), 4.12 (2H, m), 4.85 (1H, q, J=8 Hz), 5.87, 5.90 (2H, s), 6.12 (1H, d, J=8 Hz), 6.55–6.61 (2H, m), 6.68 (1H, s), 7.17 (1H, d, J=8 Hz), 7.46 (3H, m), 7.69–7.80 (3H, m)

FAB MS m/z 518 [M+H]⁺

Example 13-4)

N-[(2RS,3RS)-2-(3,4-Methylenedioxyphenyl)-3-cyclohexyl-3-hydroxypropionyl]-L-phenylalanine Benzyl Ester (143 mg)

NMR (CDCl₃, δ): 0.95–1.73 (11H, m), 2.92–3.13 (2H, m), 3.40–3.50 (1H, m), 3.68–3.75 (1H, m), 3.80–3.90 (1H, m), 4.79–4.93 (1H, m), 5.04–5.20 (2H, m), 5.95 (3H, m), 6.57–6.77 (4H, m), 6.93 (1H, m), 7.03–7.37 (8H, m)

FAB MS m/z 530 [M+H]⁺

Example 13-5)

N-[(2RS,3RS)-2-(3,4-Methylenedioxyphenyl)-3-cyclohexyl-3-hydroxypropionyl]-L-leucine Benzyl Ester (155 mg)

NMR (CDCl₃, δ): 0.80–0.90 (6H, m), 0.98–1.73 (14H, m), 3.45–3.55 (1H, m), 3.75–3.88 (2H, m), 4.60–4.70 (1H, m), 5.03–5.18 (2H, m), 5.95 (3H, m), 6.65–6.77 (3H, m), 7.23–7.35 (5H, m)

FAB MS m/z: 496 [M+H]⁺

Example 13-6)

N-[(2RS,3RS)-2-(3,4-Methylenedioxyphenyl)-3-cyclohexyl-3-hydroxypropionyl]-L-phenylglycine Methyl Ester (156 mg)

NMR (CDCl₃, δ): 0.95–1.77 (11H, m), 3.55 (2H, m), 3.68, 3.72 (3H, s), 3.85 (1H, m), 5.49 (1H, d, J=8 Hz), 5.97 (2H, m), 6.57–6.80 (4H, m), 7.17 (1H, m), 7.30 (4H, m)

FAB MS m/z: 440 [M+H]⁺

Example 13-7)

N-[(2RS,3RS)-2-(3,4-Methylenedioxyphenyl)-3-cyclohexyl- 3-hydroxypropionyl]-L-Trp(Me)-OMe (185 mg)

NMR (CDCl₃, δ): 0.95–1.75 (11H, m), 3.10–3.29 (2H, m), 3.40–3.45 (1H, m), 3.63–3.72 (6H, m), 3.85–3.95 (2H, m), 4.78–4.92 (1H, m), 5.92, 5.98 (2H, s), 6.09, 6.12 (1H, d, J=8 Hz), 6.28–6.75 (4H, m), 7.00–7.50 (4H, m)

FAB Ms m/z: 507 [M+H]⁺

Example 13-8)

N-[(2RS,3RS)-2-(2-Methoxyphenyl)-3-cyclohexyl-3-hydroxypropionyl]-L-tryptophan Methyl Ester (144 mg)

NMR (CDCl₃, δ): 0.90–1.32 (5H, m), 1.48–1.80 (6H, m), 3.10–3.30 (1H, m), 3.58–3.60 (3H, s), 3.63, 3.70 (3H, s), 4.00–4.12 (3H, m), 4.82–4.92 (1H, m), 6.38, 6.42 (1H, d, J=7 Hz), 6.20–7.52 (9H, m), 7.77, 8.05 (1H, s)

FAB MS m/z: 555 [M+H]⁺

Example 13-9)

N-[(2RS,3RS)-2-(3,4-Methylenedioxyphenyl)-3-hydroxyheptanoyl]-L-tryptophan Methyl Ester (260 mg)

NMR (CDCl₃, δ): 0.76–0.86 (3H, m), 1.10–1.50 (6H, m), 3.12–3.30 (3H, m), 3.62, 3.68 (3H, s), 4.00–4.12 (1H, m), 4.82–4.96 (1H, m), 5.92, 5.98 (2H, s), 6.02–6.13 (1H, m), 6.53–6.92 (4H, m), 7.02–7.50 (4H, m), 8.00, 8.08 (1H, s)

FAB MS m/z: 467 [M+H]⁺

Example 13-10)

N-[(2RS,3RS)-2-(3,4-Methylenedioxyphenyl)-3-hydroxyhexanoyl]-L-tryptophan Methyl Ester (172 mg)

NMR (CDCl₃, δ): 0.76–0.86 (3H, m), 1.12–1.40 (3H, m), 1.40–1.58 (1H, m), 3.18–3.24 (2H, m), 3.28 (1H, t, J=7 Hz), 3.65, 3.70 (3H, s), 3.85–4.12 (2H, m), 4.72–4.98 (1H, m), 5.92, 5.98 (2H, s), 6.02–6.15 (1H, m), 6.52–6.90 (4H, m), 7.02–7.22 (2H, m), 7.30–7.48 (2H, m), 8.00, 8.08 (1H, s)

FAB MS m/z 453 [M+H]⁺

Example 13-11)

N-[(2RS,3RS)-2-(3,4-Methylenedioxyphenyl)-3-hydroxyoctanoyl]-L-tryptophan Methyl Ester (170 mg)

NMR (CDCl₃, δ): 0.80–0.88 (3H, m), 1.10–1.56 (8H, m), 3.18–3.24 (2H, m), 3.28 (1H, t, J=7 Hz), 3.72, 3.78 (3H, s), 3.98–4.10 (1H, m), 4.80–4.96 (1H, m), 5.92, 5.98 (2H, s), 6.02–6.12 (1H, m), 6.52–6.92 (4H, m), 7.02–7.50 (4H, m), 7.96, 8.10 (1H, s)

FAB MS m/z: 481 [M+H]⁺

Example 13-12)

N-[(2RS,3RS)-2-(3,4-Methylenedioxyphenyl)-3-hydroxy-4-ethylhexanoyl]-L-tryptophan Methyl Ester (168 mg)

NMR (CDCl₃, δ): 0.70–0.92 (7H, m), 1.15–1.54 (4H, m), 3.18–3.25 (1H, m), 3.26–3.30 (1H, m), 3.42–3.48 (1H, dd, J=3, 8 Hz), 3.64, 3.68 (3H, s), 3.80–4.25 (2H, m), 4.82–5.00 (1H, m), 5.92, 5.98 (2H, s), 6.03–6.18 (1H, m), 6.50–6.90 (4H, m), 7.02–7.55 (4H, m), 7.96, 8.08 (1H, s)

FAB MS m/z: 481 [M+H]⁺

Example 13-13)

N-[(2RS,3RS)-2-(3,4-Methylenedioxyphenyl)-3-hydroxy-5-methylhexanoyl]-L-tryptophan Methyl Ester (196 mg)

NMR (CDCl₃, δ): 0.73–0.93 (6H, m), 1.20–1.30 (2H, m), 1.75–1.90 (1H, m), 3.15 (1H, d, J=7 Hz), 3.14, 3.18 (3H, s), 3.75–3.95 (1H, m), 4.05–4.15 (1H, m), 4.80–4.95 (1H, m), 5.92–5.98 (2H, s), 6.00–6.10 (1H, m), 6.50–6.90 (4H, m), 7.00–7.50 (4H, m), 7.98, 8.06 (1H, s)

FAB MS m/z: 467 [M+H]⁺

Example 13-14)

N-[(2RS,3RS)-2-(3,4-Methylenedioxyphenyl)-3-hydroxy-4-cyclohexylbutyryl]-L-tryptophan Methyl Ester (175 mg)

NMR (CDCl₃, δ): 0.55–1.30 (13H, m), 3.03 (1H, d, J=8 Hz), 3.21, 3.28 (2H, t, J=7 Hz), 3.64, 3.6 (3H, s), 3.80–3.95 (1H, m), 4.05–4.20 (1H, m), 4.80–4.95 (1H, m), 5.92, 5.97 (2H, s), 6.02, 6.08 (1H, d, J=8 Hz), 6.50–6.90 (4H, m), 7.00–7.40 (4H, m), 7.97, 8.04 (1H, s)

FAB MS m/z: 507 [M+H]⁺

Example 13-15)

N-[(2RS,3RS)-2-(3,4-Methylenedioxyphenyl)-3-hydroxyvaleryl]-L-tryptophan Methyl Ester (201 mg)

NMR (CDCl₃, δ): 0.88, 0.90 (3H, t, J=7 Hz), 1.15–1.40 (2H, m), 3.15–3.30 (3H, m), 3.65, 3.68 (3H, s), 3.85–4.10 (2H, m), 4.80–4.95 (1H, m), 5.91, 5.97 (2H, s), 6.02, 6.08 (1H, d, J=8 Hz), 6.50–6.93 (4H, m), 7.00–7.50 (4H, m), 7.97, 8.06 (1H, s)

FAB MS m/z: 439 [M+H]⁺

Example 13-16)

N-[(2RS,3RS)-2-(3,4-Methylenedioxyphenyl)-3-hydroxy-5,5-dimethylhexanoyl]-L-tryptophan Methyl Ester (193 mg)

NMR (CDCl₃, δ): 0.83, 0.86 (9H, s), 0.98–1.35 (2H, m), 3.10–3.35 (3H, m), 3.63, 3.68 (3H, s), 4.10–4.25 (2H, m), 4.80–4.95 (1H, m), 5.92, 5.98 (2H, s), 6.08, 6.12 (1H, d, J=8 Hz), 6.55–6.95 (4H, m), 7.00–7.50 (4H, m), 7.98, 8.08 (1H, s)

FAB MS m/z: 481 [M+H]⁺

Example 13-17)

N-[(2RS,3RS)-3-Hydroxy-4-methyl-2-(3,4-methylenedioxyphenyl)valeryl]-L-tryptophan Methyl Ester (1.08 g)

NMR (CDCl₃, δ): 0.78–0.86 (3H, m), 0.90–0.96 (3H, m), 1.34–1.48 (1H, m), 3.19–3.39 (3H, m), 3.66, 3.69 (total 3H, s), 3.72–3.76 (0.5H, m), 3.87–3.98 (1.5H, m), 4.82–4.95 (1H, m), 5.92, 5.97 (total 2H, s), 6.08 (0.5H, d, J=8 Hz), 6.12 (0.5H, d, J=8 Hz), 6.54–6.74 (3H, m), 6.92–7.22 (3H, m), 7.29–7.38 (1.5H, m), 7.49 (0.5H, d, J=8 Hz), 7.99–8.04 (1H, br s)

Example 13-18)

N-[(2RS,3RS)-2-(1,4-Benzodioxan-6-yl)-3-hydroxyheptanoyl]-L-tryptophan Methyl Ester (241 mg)

NMR (CDCl₃, δ): 0.78–0.90 (3H, m), 1.10–1.48 (6H, m), 3.12–3.30 (3H, m), 3.14, 3.16 (3H, s), 4.03–4.18 (1H, m), 4.20, 4.28 (4H, s), 4.82–4.99 (1H, m), 6.08–6.25 (1H, m), 6.55–6.92 (3H, m), 7.00–7.50 (3H, m), 7.98, 8.08 (1H, s)

FAB MS m/z: 481 [M+H]⁺

Example 13-19)

N-[(2RS,3RS)-2-(2-Naphthyl)-3-hydroxyheptanoyl]-L-tryptophan Methyl Ester (256 mg)

NMR (CDCl₃, δ): 0.75–0.82 (3H, m), 1.05–1.50 (6H, m), 3.05–3.30 (2H, m), 3.48 (1H, d, J=8 Hz), 3.60–3.68 (1H, s), 4.04–4.18 (1H, m), 4.22–4.32 (1H, m), 4.78–4.95 (1H, m), 5.99, 6.08 (1H, d, J=7 Hz), 6.12, 6.70 (1H, d, J=3 Hz), 6.80–7.30 (4H, m), 7.38–7.92 (8H, m)

FAB MS m/z: 473 [M+H]⁺

Example 13-20)

N-[(2RS,3RS)-2-(3,4-Dimethoxyphenyl)-3-hydroxyheptanoyl]-L-tryptophan Methyl Ester (244 mg)

NMR (CDCl₃, δ): 0.84 (3H, t, J=7 Hz), 1.18–1.45 (6H, m), 3.08, 3.15 (1H, d, J=4 Hz), 3.18–3.22 (1H, m), 3.25–3.32 (2H, m), 3.68, 3.70 (3H, s), 3.71, 3.76 (3H, s), 3.86, 3.89 (3H, s), 4.18–4.30 (1H, m), 4.80–4.94 (1H, m), 6.10, 6.18 (1H, d, J=8 Hz), 6.45–6.87 (3H, m), 6.96–7.46 (5H, m), 7.92, 8.05 (1H, s)

FAB MS m/z: 483 [M+H]⁺

Example 13-21)

N-[(2RS)-2-(3,4-Methylenedioxyphenyl)-3-phenylpropionyl]-L-tryptophan Methyl Ester (630 mg)

NMR (CDCl₃, δ): 2.86–2.97 (1H, m), 3.08–3.28 (2H, m), 3.39–3.53 (2H, m), 3.59, 3.63 (total 3H, s), 4.80–4.93 (1H, m), 5.88–5.98 (3H, m), 6.36–6.82 (4H, m), 6.98–7.07 (2H, m), 7.10–7.33 (7H, m), 7.90–8.00 (1H, m)

Example 13-22)

N-[(2RS,3RS)-3-Hydroxy-2-(3,4-methylenedioxyphenyl)-3-phenylbutyryl]-L-tryptophan Methyl Ester (150 mg)

NMR (CDCl₃, δ): 2.50–2.70 (2H, m), 3.19–3.30 (3H, m), 3.66, 3.69 (total 3H, s), 3.75–3.85 (1H, m), 4.24–4.36 (1H, m), 4.85–4.97 (1H, m), 5.94, 5.98 (total 2H, s), 6.07–6.22 (1H, m), 6.57–6.76 (3H, m),7.02–7.26 (7H, m), 7.30–7.50 (2H, m), 7.98–8.08 (1H, m)

Example 13-23)

N-[(2RS,3SR)-3-Hydroxy-2-(3,4-methylenedioxyphenyl)-3-(2-pyridyl)propionyl]-L-tryptophan Methyl Ester (50 mg)

NMR (CDCl$_3$, δ): 3.22–3.26 (2H, m), 3.66, 3.67 (total 3H, s), 3.86–3.89 (1H, m), 4.57–4.68 (1H, m), 4.85–4.98 (1H, m), 5.38–5.47 (1H, m), 5.85, 5.90 (total 2H, s), 6.38–6.70 (4H, m), 6.97–7.58 (7H, m), 7.96–8.10 (1H, m), 8.39–8.46 (1H, m)

Example 13-24)

N-[(2RS,3SR)-3-Hydroxy-2,3-bis(3,4-methylenedioxyphenyl)propionyl]-L-tryptophan Methyl Ester (438 mg)

NMR (CDCl$_3$, δ): 3.20–3.30 (2H, m), 3.40–3.48 (1H, m), 3.67, 3.70 (total 3H, s), 4.37 (0.5H, d, J=3 Hz), 4.66 (0.5H, d, J=3 Hz), 4.87–5.03 (2H, m), 5.85–5.94 (4H, m), 6.06 (0.5H, d, J=8 Hz), 6.11 (0.5H, d, J=8 Hz), 6.34–6.50 (1H, m), 6.52–6.87 (5H, m), 6.99–7.22 (2H, m), 7.29–7.49 (2H, m), 7.96–8.08 (2H, m)

Example 13-25)

N-[(2RS,3SR)-3-Hydroxy-2-(3,4-methylenedioxyphenyl)-3-(3,4,5-trimethoxyphenyl)propionyl]-L-tryptophan Methyl Ester (270 mg)

NMR (CDCl$_3$, δ): 3.22–3.29 (2H, m), 3.42–3.47 (1H, m), 3.66–3.79 (12H, m), 4.85–5.03 (2H, m), 5.89 (1H, s), 5.93 (1H, s), 6.06 (0.5H, d, J=8 Hz), 6.12 (0.5H, d, J=8 Hz), 6.28 (1H, s), 6.37 (1H, s), 6.38 (0.5H, dd, J=1, 8 Hz), 6.47 (0.5H, dd, J=1, 8 Hz), 6.53–6.73 (3H, m), 6.98–7.21 (3H, m), 7.29–7.48 (2H, m), 7.98–8.02 (0.5H, br), 8.08–8.12 (0.5H, br)

Example 13-26)

N-[(2RS,3SR)-3-Hydroxy-2-(3,4-methylenedioxyphenyl)-3-(4-methoxycarbonylphenyl)propionyl]-L-tryptophan Methyl Ester (195 mg)

NMR (CDCl$_3$, δ): 3.22–3.29 (2H, m), 3.44–3.49 (1H, m), 3.68, 3.70 (total 3H, s), 3.87, 3.89 (total 3H, s), 4.68 (0.5H, d, J=3 Hz), 4.85–4.98 (1H, m), 4.94 (0.5H, d, J=3 Hz), 5.87–5.95 (2H, m), 6.02–6.10 (2H, m), 6.30 (0.5H, dd, J=2, 9 Hz), 6.37 (0.5H, dd, J=2, 9 Hz), 6.50–6.74 (3H, m), 6.98–7.48 (6H, m), 7.83 (1H, d, J=8 Hz), 7.88 (1H, d, J=8 Hz), 7.97–8.09 (1H, m)

Example 13-27)

N-[(2RS,3SR)-3-Hydroxy-2-(3,4-methylenedioxyphenyl)-3-(4-biphenylyl)propionyl]-L-tryptophan Methyl Ester (293 mg)

NMR (CDCl$_3$, δ): 3.22–3.31 (2H, m), 3.52–3.58 (1H, m), 3.66, 3.70 (total 3H, s), 4.38–4.43 (0.5H, br s), 4.80–5.18 (2.5H, m), 5.88–5.97 (2H, m), 6.08–6.17 (1H, m), 6.38–6.50 (1H, m), 6.55–6.62 (2H, m), 6.67, 6.74 (total 1H, s), 7.03–7.59 (13H, m), 7.95–8.03 (1H, m)

Example 13-28)

N-[(2RS,3SR)-3-Hydroxy-2-(3,4-methylenedioxyphenyl)-3-(2-n-butyl-1-tert-butoxycarbonyl-1H-imidazol-4-yl)propionyl]-L-tryptophan Methyl Ester (130 mg)

NMR (CDCl$_3$, δ): 0.86–0.96 (3H, m), 1.27–1.40 (2H, m), 1.54, 1.59 (total 9H, s), 1.56–1.68 (2H, m), 2.84–2.96 (2H, m), 3.20–3.29 (2H, m), 3.60 (3H, s), 3.86–4.03 (1.5H, m), 4.50 (0.5H, d, J=7 Hz), 4.84–5.03 (1H, m), 5.90, 5.95 (total 2H, s), 6.24–6.36 (1H, m), 6.58–6.69 (2H, m), 6.79 (1H, s), 6.93–7.20 (3H, m), 7.27–7.50 (3H, m), 8.06–8.16 (1H, m)

Example 14-1)

To a solution of N-[(2RS,3RS)-2-(3,4-methylenedioxyphenyl)-3-cyclohexyl-3-hydroxypropionyl]-L-tryptophan methyl ester (160 mg) in MeOH (2 ml) was added 1M aqueous sodium hydroxide solution (1 ml) at room temperature. After being stirred for 1 hours at the same temperature, the mixture was concentrated in vacuo. The residue was dissolved in 1N hydrochloric acid (5 ml) and ethyl acetate (10 ml) and the organic layer was washed with brine, dried over magnesium sulfate, and concentrated in vacuo to give N-[(2RS,3RS)-2-(3,4-methylenedioxyphenyl)-3-cyclohexyl-3-hydroxypropionyl]-L-tryptophan (150 mg).

NMR (CDCl$_3$, δ): 0.88–1.75 (11H, m), 3.18–3.25 (1H, m), 3.30 (1H, t, J=7 Hz), 3.40–3.48 (1H, m), 3.85–3.96 (1H, m), 4.78–4.92 (1H, m), 5.90 (1H, m), 5.98 (1H, m), 6.37 (1H, t, J=8 Hz), 6.46–6.92 (4H, m), 7.00– 7.55 (4H, m), 8.14, 8.22 (1H, s)

FAB MS m/z: 479 [M+H]$^+$

The following compounds were obtained in substantially the same manner as that of Example 14-1).

Example 14-2)

N-[(2RS,3RS)-2-(3,4-Methylenedioxyphenyl)-3-cyclohexyl-3-hydroxypropionyl]-L-1-naphthylalanine (117 mg)

NMR (DMSO-d$_6$, δ): 0.90–1.65 (11H, m), 3.20–3.50 (2H, m),3.55–3.65 (1H, m), 3.70–3.80 (1H, m), 4.45–4.60 (1H, m), 5.94 (2H, s), 6.60–6.90 (3H, m), 7.05–7.15 (1H, m), 7.30–7.40 (1H, m), 7.40–7.60 (2H, m), 7.60–7.95 (2H, m), 8.00–8.20 (1H, m), 8.30–8.40 (1H, d, J=8 Hz)

FAB MS m/z: 490 [M+H]$^+$

Example 14-3)

N-[(2R,3R)-2-(3,4-Methylenedioxyphenyl)-3-cyclohexyl-3-hydroxypropionyl]-L-2-naphthylalanine (112 mg)

NMR (DMSO-d$_6$, δ): 0.75–1.65 (11H, m), 3.05–3.25 (2H, m), 3.16 (1H, d, J=8 Hz), 3.70–3.80 (1H, m), 4.53 (1H, q, J=7 Hz), 5.97 (2H, s), 6.74 (2H, s), 6.89 (1H, s), 7.35–7.50 (3H, m), 7.75–7.90 (3H, m), 8.21 (1H, d, J=8 Hz), 7.71 (1H, s)

FAB MS m/z: 490 [M+H]$^+$

Example 14-4)

N-[(2RS,3RS)-2-(3,4-Methylenedioxyphenyl)-3-cyclohexyl-3-hydroxypropionyl]-L-phenylalanine (103 mg)

NMR (CDCl$_3$, δ): 0.95–1.71 (11H, m), 2.88–3.21 (2H, m), 3.47–3.57 (2H, m), 3.60–4.10 (1H, m), 4.60–4.80 (1H, m), 5.93, 5.98 (2H, s), 6.32–6.47 (1H, m), 6.55–6.73 (3H, m), 6.82–6.85 (1H, m), 7.01–7.13 (2H, m), 7.20–7.25 (1H, m)

FAB MS m/z: 440 [M+H]$^+$

Example 14-5)

N-[(2RS,3RS)-2-(3,4-Methylenedioxyphenyl)-3-cyclohexyl-3-hydroxypropionyl]-L-leucine (105 mg)

NMR (CDCl₃, δ): 0.85–0.94 (6H, m), 0.98–1.80 (14H, m), 3.47–3.68 (1H, m), 3.87–4.03 (1H, m), 4.35–4.57 (1H, m), 5.93 (2H, s), 6.30 (1H, m), 6.63–6.93 (3H, m)

FAB MS m/z: 406 [M+H]⁺

Example 14-6)

N-[(2R,3R)-2-(3,4-Methylenedioxyphenyl)-3-cyclohexyl-3-hydroxypropionyl]-L-phenylglycine (111 mg)

NMR (DMSO-d₆, δ): 0.80–1.70 (11H, m), 3.77, 3.80 (3H, s), 5.23–5.30 (1H, m), 5.90–6.00 (2H, m), 6.70–6.95 (3H, m), 7.20–7.40 (5H, m), 8.50–8.65 (1H, m)

FAB MS m/z: 426 [M+H]⁺

Example 14-7)

N-[(2RS,3RS)-2-(3,4-Methylenedioxyphenyl)-3-cyclohexyl-3-hydroxypropionyl]-L-Trp(Me)-OH (165 mg)

NMR (CDCl₃, δ): 0.85–1.78 (11H, m), 3.10–3.30 (3H, m), 4.70–4.80 (1H, m), 3.60, 3.68 (3H, s), 3.83–3.98 (1H, m), 5.88, 5.92 (1H, s), 6.30–6.80 (5H, m), 6.95–7.50 (4H, m)

FAB MS m/z: 493 [M+H]⁺

Example 14-8)

N-[(2RS,3RS)-2-(2-Methoxyphenyl)-3-cyclohexyl-3-hydroxypropionyl]-L-tryptophan (98 mg)

NMR (CDCl₃, δ): 0.85–1.20 (5H, m), 1.22–1.73 (6H, m), 3.22 (1H, d, J=7 Hz), 3.28 (1H, t, J=7 Hz), 3.50, 3.53 (3H, s), 3.95–4.10 (1H, m), 4.76–4.88 (1H, m), 6.40, 6.53 (1H, d, J=8 Hz), 6.46–7.56 (9H, m), 7.94, 8.18 (1H, s)

FAB MS m/z: 465 [M+H]⁺

Example 14-9)

N-[(2RS,3RS)-2-(3,4-Methylenedioxyphenyl)-3-hydroxyheptanoyl]-L-tryptophan (220 mg)

NMR (CDCl₃, δ): 0.75–0.85 (3H, m), 1.06–1.50 (6H, m), 3.14–3.38 (3H, m), 3.98–4.12 (1H, m), 4.78–4.92 (1H, m), 5.86–5.92 (1H, m), 5.94–5.98 (1H, m), 6.32, 6.40 (1H, d, J=7 Hz), 6.44–6.90 (4H, m), 6.98–7.52 (4H, m), 8.20, 8.28 (1H, s)

FAB MS m/z: 453 [M+H]⁺

Example 14-10)

N-[(2RS,3RS)-2-(3,4-Methylenedioxyphenyl)-3-hydroxyhexanoyl]-L-tryptophan (130 mg)

NMR (CDCl₃, δ): 0.75–0.86 (3H, m), 1.10–1.30 (3H, m), 1.35–1.55 (1H, m), 3.15–3.38 (3H, m), 4.00–4.18 (2H, m), 4.76–4.95 (1H, m), 5.88, 5.96 (1H, s), 6.32, 6.40 (1H, d, J=7 Hz), 6.45–6.60 (2H, m), 6.68–6.90 (2H, m), 7.00–7.20 (2H, m), 7.30–7.52 (2H, m), 8.20, 8.28 (1H, s)

FAB MS m/z: 439 [M+H]⁺

Example 14-11)

N-[(2R3S,3RS)-2-(3,4-Methylenedioxyphenyl)-3-hydroxyoctanoyl]-L-tryptophan (140 mg)

NMR (CDCl₃, δ): 0.78–0.86 (3H, m), 1.02–1.50 (8H, m), 3.10–3.30 (3H, m), 4.00–4.12 (1H, m), 4.75–4.92 (1H, m), 5.85–5.96 (2H, m), 6.30–6.90 (4H, m), 6.96–7.52 (4H, m), 8.18, 8.28 (1H, s)

FAB MS m/z: 467 [M+H]⁺

Example 14-12)

N-[(2RS,3RS)-2-(3,4-Methylenedioxyphenyl)-3-hydroxy-4-ethylhexanoyl]-L-tryptophan (143 mg)

NMR (CDCl₃, δ): 0.68–0.92 (7H, m), 1.05–1.50 (4H, m), 3.16–3.38 (2H, m), 3.40–3.50 (1H, m), 4.15–4.30 (1H, m), 4.76–4.92 (1H, m), 5.87–5.97 (2H, m), 6.30, 6.39 (1H, d, J=8 Hz), 6.45–6.90 (4H, m), 7.00–7.54 (4H, m), 8.12, 8.24 (1H, s)

FAB MS m/s 467 [M+H]⁺

Example 14-13)

N-[(2RS,3RS)-2-(3,4-Methylenedioxyphenyl)-3-hydroxy-5-methylhexanoyl]-L-tryptophan (161 mg)

NMR (CDCl₃, δ): 0.65–0.95 (6H, m), 1.10–1.35 (2H, m), 1.65–1.85 (1H, m), 3.00–3.35 (3H, m), 4.05–4.20 (1H, m), 4.70–4.90 (1H, m), 5.82, 5.83 (1H, s), 5.93, 5.94 (1H, s), 6.35–6.90 (5H, m), 6.95–7.55 (4H, m), 8.26, 8.35 (1H, m)

FAB MS m/z: 453 [M+H]⁺

Example 14-14)

N-[(2RS,3RS)-2-(3,4-Methylenedioxyphenyl)-3-hydroxy-4-cyclohexylbutyryl]-L-tryptophan (144 mg)

NMR (CDCl₃, δ): 0.50–1.75 (13H, m), 3.05–3.35 (3H, m), 4.10–4.25 (1H, m), 4.75–4.90 (1H, m), 5.82, 5.83 (1H, s), 5.92, 5.93 (1H, s), 6.35–6.90 (5H, m), 6.95–7.53 (4H, m), 8.20, 8.30 (1H, s3)

FAB MS m/z: 493 [M+H]⁺

Example 14-15)

N-[(2RS,3RS)-2-(3,4-Methylenedioxyphenyl)-3-hydroxyvaleryl]-L-tryptophan (188 mg)

NMR (CDCl₃, δ): 0.75–0.90 (3H, m), 1.00–1.30 (2H, m), 3.10–3.30 (3H, m), 3.90–4.05 (1H, m), 4.70–4.90 (1H, m), 5.80, 5.92 (2H, m), 6.35–6.90 (5H, m), 6.90–7.50 (4H, m), 8.29, 8.38 (1H, s)

FAB MS m/z 425 [M+H]⁺

Example 14-16)

N-[(2RS,3RS)-2-(3,4-Methylenedioxyphenyl)-3-hydroxy- 5,5-dimethylhexanoyl]-L-tryptophan (125 mg)

NMR (CDCl₃, δ): 0.79, 0.82 (9H, s), 1.00–1.35 (2H, m), 3.10–3.40 (3H, m), 4.10–4.25 (1H, m), 4.75–4.90 (1H, m), 5.88, 5.95 (2H, s), 6.27, 6.32 (1H, d, J=7 Hz), 6.45–6.90 (4H, m), 7.00–7.55 (4H, m), 8.12, 8.19 (1H, s)

FAB MS m/z: 467 [M+H]⁺

Example 14-17)

N-[(2RS,3RS)-3-Hydroxy-4-methyl-2-(3,4-methylenedioxyphenyl)valeryl]-L-tryptophan (1.00 g)

NMR (CDCl₃, δ): 0.73 (1.5H, d, J=8 Hz), 0.80 (1.5H, d, J=8 Hz), 0.87 (1.5H, d, J=7 Hz), 0.91 (1.5H, d, J=7 Hz), 1.29–1.45 (1H, m), 3.19–3.38 (3H, m), 3.92 (0.5H, dd, J=4, 10 Hz), 3.99 (0.5H, dd, J=4, 10 Hz), 4.78–4.88 (1H, m), 5.88 (1H, d, J=2 Hz), 5.96 (1H, s), 6.29 (0.5H, d, J=8 Hz), 6.35 (0.5H, d, J=8 Hz), 6.49 (0.5H, d, J=9 Hz), 6.58 (1.5H, d, J=8 Hz), 6.70 (1.5H, d, J=9 Hz), 6.90 (0.5H, d, J=1 Hz), 6.98–7.22 (2H, m), 7.27–7.35 (1.5H, m), 7.51 (0.5H, d, J=8 Hz), 8.10–8.14 (0.5H, br s), 8.20–8.23 (0.5H, br s)

FAB MS: 439.0 [M+H]⁺

Example 14-18)

N-[(2RS,3RS)-2-(1,4-Benzodioxan-6-yl)-3-hydroxyheptanoyl]-L-tryptophan (148 mg)

NMR (CDCl₃, δ): 0.75–0.88 (3H, m), 1.10–1.42 (6H, m), 3.15–3.38 (3H, m), 4.00–4.12 (1H, m), 4.15, 4.22 (4H, s), 4.38–4.96 (1H, m), 6.30–6.46 (1H, m), 6.50–6.90 (3H, m), 6.96–7.52 (3H, m), 8.15, 8.22 (1H, s)

FAB MS m/z: 467 [M+H]⁺

Example 14-19)

N-[(2RS,3RS)-2-(2-Naphthyl)-3-hydroxyheptanoyl]-L-tryptophan (218 mg)

NMR (CDCl₃, δ): 0.70–0.80 (3H, m), 1.03–1.48 (6H, m), 3.09–3.35 (2H, m), 3.42, 3.48 (1H, d, J=8 Hz), 4.20–4.35 (1H, m), 4.72–4.92 (1H, m), 6.28, 6.34 (1H, d, J=8 Hz), 6.40, 6.68 (1H, d, J=3 Hz), 6.75–7.30 (4H, m), 7.44–7.60 (4H, m), 7.63–7.92 (4H, m)

FAB MS m/z: 459 [M+H]⁺

Example 14-20)

N-[(2RS,3RS)-2-(3,4-Dimethoxyphenyl)-3-hydroxyheptanoyl]-L-tryptophan (205 mg)

NMR (CDCl₃-CD₃OD, δ): 0.83 (3H, m), 1.15–1.42 (6H, m), 3.22 (1H, d, J=7 Hz), 3.30 (2H, t, J=6 Hz), 3.68, 3.74 (3H, s), 3.85, 3.90 (3H, s), 4.16–4.28 (1H, m), 4.72–4.88 (1H, m), 6.55–6.85 (3H, m), 6.93–7.50 (5H, m)

FAB MS m/z: 469 [M+H]⁺

Example 14-21)

N-[(2RS)-2-(3,4-Methylenedioxyphenyl)-3-phenylpropionyl]-L-tryptophan (522 mg)

NMR (CDCl₃, δ): 2.84–2.95 (1H, m), 3.10–3.28 (2H, m), 3.36–3.50 (2H, m), 4.77–4.85 (1H, m), 5.86–5.98 (2H, m), 6.47–6.75 (4H, m), 6.95–7.07 (2H, m), 7.10–7.34 (7H, m), 7.99–8.05 (1H, br)

FAB MS: 457.3 [M+H]⁺

Example 14-22)

N-[(2RS,3RS)-3-Hydroxy-2-(3,4-methylenedioxyphenyl)-4-phenylbutyryl]-L-tryptophan (110 mg)

NMR (CDCl₃, δ): 2.42–2.68 (2H, m), 3.17–3.31 (3H, m), 4.22–4.35 (1H, m), 4.78–4.90 (1H, m), 5.87–5.90 (1H, m), 5.95–5.99 (1H, m), 6.33–6.42 (1H, m), 6.50–6.76 (3H, m), 6.98–7.52 (9H, m), 8.06–8.09 0.5H, br s), 8.12–8.16 (0.5H, br s)

FAB MS: 487.5 [M+H]⁺

Example 14-23)

N-[(2RS,3SR)-3-Hydroxy-2-(3,4-methylenedioxyphenyl)-3-(2-pyridyl)propionyl]-L-tryptophan (30 mg)

NMR (DMSO-d₆, δ): 2.82–3.08 (2H, m), 4.08 (1H, t, J=8 Hz), 4.28–4.36 (1H, m), 5.06–5.19 (1H, m), 5.96, 5.97 (2H, s), 6.58–6.78 (2H, m), 6.85–7.42 (9H, m), 8.16–8.20 (1H, m), 8.44–8.54 (1H, m)

FAB MS: 474.2 [M+H]⁺

Example 14-24)

N-[(2RS,3SR)-3-Hydroxy-2,3-bis(3,4-methylenedioxyphenyl)propionyl]-L-tryptophan (333 mg)

NMR (CDCl₃, δ): 3.15–3.44 (3H, m), 4.80–5.00 (2H, m), 5.78–5.93 (4H, m), 6.30–6.42 (2H, m), 6.44–6.58 (4H, m), 6.68–6.88 (1H, m), 6.94–7.19 (2H, m), 7.24–7.50 (3H, m), 8.14–8.24 (1H, m)

FAB MS: 517 [M]⁺, 539.3 [M+Na]⁺

Example 14-25)

N-[(2RS,3SR)-3-Hydroxy-2-(3,4-methylenedioxyphenyl)-3-(3,4,5-trimethoxyphenyl)propionyl]-L-tryptophan (212 mg)

NMR (CDCl₃, δ): 3.22–3.43 (2H, m), 3.64 (3H, s), 3.71 (3H, s), 3.76, 3.78 (total 3H, s), 4.83–5.03 (2H, m), 5.83 (1H, d, J=3 Hz), 5.91 (1H, d, J=3 Hz), 6.23–6.40 (4H, m), 6.50–6.58 (2H, m), 6.72 (0.5H, d, J=1 Hz), 6.78 (0.5H, d, J=1 Hz), 6.96–7.18 (3H, m), 7.27–7.50 (2H, m), 8.15–8.18 (0.5H, br s), 8.22–8.25 (0.5H, br s)

FAB MS: 545.4 [M-OH]⁺

Example 14-26)

N-[(2RS,3SR)-3-Hydroxy-2-(3,4-methylenedioxyphenyl)-3-(4-carboxyphenyl)propionyl]-L-tryptophan (150 mg)

NMR (DMSO-d₆, δ): 2.95–3.16 (3H, m), 3.87 (1H, dd, J=2, 10 Hz), 4.48–4.58 (1H, m), 5.08 (1H, d, J=10 Hz), 5.87–5.93 (2H, m), 6.50–6.66 (2H, m), 6.77–6.90 (2H, m), 6.96–7.10 (2H, m), 7.20–7.58 (4H, m), 7.69–7.75 (2H, m), 8.22–8.30 (1H, m)

FAB MS: 517.2 [M+H]⁺

Example 14-27)

N-[(2RS,3SR)-3-Hydroxy-2-(3,4-methylenedioxyphenyl)-3-(4-biphenylyl)propionyl]-L-tryptophan (240 mg)

NMR (CDCl₃, δ): 3.22–3.32 (2H, m), 3.46–3.55 (1H, m), 4.85–5.00 (1H, m), 5.09–5.17 (1H, m), 5.82, 5.84 (total 1H, s), 5.89, 5.91 (total 1H, s), 6.29–6.62 (4H, m), 6.73, 6.80 (total 1H, s), 6.99–7.54 (13H, m), 8.07–8.11 (1H, brs)

FAB MS: 571.4 [M+Na]⁺

Example 15

Crude mixture of N-[(2R,3R)-, (2S,3S)-, (2R,3S)- and (2S,3R)-2-(3,4-methylenedioxyphenyl)-3-cyclohexyl-3-hydroxypropionyl]-L-tryptophan (429 mg) was purified by HPLC [Column: YMC ODS-AM, 250×20 mmI.D., 40–80% acetonitrile in 0.1% trifluoroacetic acid/water (120 minutes gradient), GILSON HPLC SYSTEM] to afford four fractions 109 mg (Isomer A), 96 mg (Isomer B), 94 mg (Isomer C) and 99 mg (Isomer D).

(Isomer A and B; retention time: 12.5 and 14.0 minutes, respectively):

N-[(2SR,3RS)-2-(3,4-Methylenedioxyphenyl)-3-cyclohexyl-3-hydroxypropionyl]-L-tryptophan Isomer A NMR (CDCl₃-CD₃OD, δ) 0.80–1.20 (6H, m), 1.50–1.88 (5H, m), 3.28 (2H, d, J=8 Hz), 3.52 (1H, d, J=7 Hz), 3.80–3.90 (1H, m), 4.88–4.97 (1H, m), 5.97 (2H, s), 6.54 (1H, d, J=9 Hz), 6.65–6.88 (4H, m), 7.02–7.10 (1H, m), 7.17–7.22 (1H, m), 7.30–7.42 (2H, m), 8.14 (1H, s)

Isomer B

NMR (CDCl₃-CD₃OD, δ): 0.86–1.20 (6H, m), 1.48–1.78 (4H, m), 1.92–2.00 (1H, m), 3.30 (1H, d, J=7 Hz), 3.40–3.48 (1H, m), 3.85–3.94 (1H, m), 4.75–4.81 (1H, m), 5.93 (2H, s), 6.52 (1H, d, J=9 Hz), 6.60–6.72 (2H, m), 6.90 (2H, s), 7.04–7.56 (4H, m), 8.78 (1H, s)

(Isomer C; retention time: 15.0 minutes):

N-[(2R,3R)-2-(3,4-Methylenedioxyphenyl)-3-cyclohexyl-3-hydroxypropionyl]-L-tryptophan Isomer C NMR (CDCl₃-CD₃OD, δ): 0.88–1.15 (5H, m), 1.24–1.70 (6H, m), 3.22 (2H, d, J=7 Hz), 3.50 (1H, d, J=8 Hz), 3.96 (1H, dd, J=7 Hz), 4.85 (1H, m), 5.98 (2H, s), 6.52–6.78 (5H, m), 7.04 (1H, t, J=8 Hz), 7.18 (1H, t, J=8 Hz), 7.32 (1H, d, J=8 Hz), 7.38 (1H, d, J=8 Hz), 8.10 (1H, s)

FAB MS m/z: 479 [M+H]+

(Isomer D; retention time: 15.7 minutes)

N-[(2S,3S)-2-(3,4-Methylenedioxyphenyl)-3-cyclohexyl-3-hydroxypropionyl]-L-tryptophan Isomer D NMR (CDCl$_3$-CD$_3$OD, δ) 0.92–1.74 (11H, m), 3.20–3.45 (2H, m), 3.85 (1H, d, J=8 Hz), 4.72–4.80 (1H, m), 5.93 (2H, s), 6.50–6.92 (5H, m), 7.02–7.40 (4H, m), 8.10 (1H, s)

Example 16

N-[(2RS,3RS)-2-(3,4-Methylenedioxyphenyl)-3-hydroxyheptanoyl]-L-Trp(Me)-OMe (1.33 g) was purified by silica gel column chromatography (eluent; hexane:ethyl acetate=3:1) to afford N-[(2R,3R)-2-(3,4-methylenedioxyphenyl)-3-hydroxyheptanoyl]-L-Trp(Me)-OMe (1.39 g) and N-[(2S,3S)-2-(3,4-methylenedioxyphenyl)-3-hydroxyheptanoyl]-L-Trp(Me)-OMe (1.35 g).

N-[(2R,3R)-2-(3,4-Methylenedioxyphenyl)-3-hydroxyheptanoyl]-L-Trp(Me)-OMe

Rf: 0.56 (eluent; hexane:ethyl acetate=1:1)

NMR (CDCl$_3$, δ): 0.81 (3H, t, J=7 Hz), 1.10–1.50 (6H, m), 3.20 (1H, d, J=8.5 Hz), 3.28 (2H, t, J=7.5 Hz), 3.62 (3H, s), 4.05 (2H, m), 4.82 (1H, m), 5.90 (2H, s), 6.18 (1H, d, J=7.5 Hz), 6.52 (1H, d, J=8 Hz), 6.64 (2H, m), 6.88 (1H, d, J=3 Hz), 7.10 (1H, t, J=8 Hz), 7.18 (1H, t, J=8 Hz), 7.32 (1H, d, J=8 Hz), 7.48 (1H, d, J=8 Hz), 8.28 (1H, s)

FAB MS m/z: 467 [M+H]+

N-[(2S,3S)-2-(3,4-Methylenedioxyphenyl)-3-hydroxyheptanoyl]-L-Trp(Me)-OMe

Rf: 0.42 (eluent; hexane:ethyl acetate=1:1)

NMR (CDCl$_3$, δ): 0.80 (3H, t, J=7 Hz), 1.10–1.50 (6H, m), 3.12–3.30 (3H, m), 3.68 (3H, s), 3.75–4.10 (2H, m), 4.92 (1H, m), 5.98 (2H, s), 6.05 (1H, d, J=8 Hz), 6.59 (2H, d, J=7 Hz), 6.68–6.75 (2H, m), 7.04 (1H, t, J=8 Hz), 7.18 (1H, t, J=8 Hz), 7.32 (2H, d, J=8 Hz), 7.99 (1H, s)

FAB MS m/z: 467 [M+H]+

The following compounds were obtained in substantially the same manner as that of Example 14-1).

Example 17

N-[(2R,3R)-2-(3,4-Methylenedioxyphenyl)-3-hydroxyheptanoyl]-L-Trp(Me)-OH (1.22 g)

NMR (CDCl$_3$, δ): 0.78 (3H, t, J=7 Hz), 1.04–1.47 (6H, m), 3.08–3.32 (3H, m), 4.00–4.10 (1H, m), 4.75–4.85 (1H, m), 5.80, 5.82 (2H, s), 6.43 (2H, d, J=8 Hz), 6.50–6.60 (2H, m), 6.80 (1H, s), 7.03 (1H, t, J=7 Hz), 7.13 (1H, t, J=8 Hz), 7.23 (1H, d, J=7 Hz), 7.47 (1H, d, J=8 Hz), 8.32 (1H, s)

FAB MS m/z: 453 [M+H]+

Example 18

N-[(2S,3S)-2-(3,4-Methylenedioxyphenyl)-3-hydroxyheptanoyl]-L-Trp(Me)-OH (1.17 g)

NMR (CDCl$_3$, δ): 0.78 (3H, t, J=7 Hz), 1.05–1.46 (6H, m), 3.10–3.23 (3H, m), 4.00–4.10 (1H, m), 4.80–4.90 (1H, m), 5.91 (2H, s), 6.50 (1H, d, J=8 Hz), 6.58 (1H, d, J=8 Hz), 6.61–6.68 (3H, m), 6.98 (1H, t, J=8 Hz), 7.11 (1H, t, J=8 Hz), 7.25 (1H, d, J=7 Hz), 7.30 (1H, d, J=8 Hz), 8.37 (1H, s)

FAB MS m/z: 453 [M+H]+

Example 19-1)

N-[(2R,3S)- and (2S,3R)-3-Hydroxy-2-(3,4-methylenedioxyphenyl)-3-phenylpropionyl]-L-tryptophan methyl ester was obtained in substantially the same manner as that of Example 13-1).

The stereoisomers were separated by silica gel column chromatography (eluent; n-hexane:ethyl acetate=2:1–3:2) to give more polar isomer (158 mg) and less polar isomer (168 mg). The stereostructures of the more polar and the less polar isomers were assigned as (2S,3R)- and (2R,3S)-configurations respectively.

More Polar Isomer

NMR (CDCl$_3$, δ): 3.20–3.26 (2H, m), 3.49–3.54 (1H, m), 3.70 (3H, s), 4.37 (1H, d, J=4 Hz), 4.94–5.00 (1H, m), 5.08 (1H, dd, J=4, 10 Hz), 5.90–5.94 (2H, m), 6.08 (1H, d, J=8 Hz), 6.35 (1H, dd, J=1, 8 Hz), 6.54–6.58 (3H, m), 6.99–7.34 (9H, m), 7.94–7.98 (1H, br)

Less Polar Isomer

NMR (CDCl$_3$, δ): 3.27 (2H, d, J=5 Hz), 3.48–3.51 (1H, m), 3.65 (3H, s), 4.73 (1H, d, J=3 Hz), 4.86–4.93 (1H, m), 5.10 (1H, dd, J=3, 7 Hz), 5.86–5.89 (2H, m), 6.12 (1H, d, J=8 Hz), 6.41 (1H, dd, J=1, 8 Hz), 6.55 (1H, d, J=8 Hz), 6.60 (1H, d, J=1 Hz), 6.76 (1H, d, J=1 Hz), 7.18–7.24 (7H, m), 7.34 (1H, d, J=8 Hz), 7.44 (1H, d, J=8 Hz), 7.99–8.03 (1H, br)

Example 19-2)

N-[(2R,3S)- and (2S,3R)-3-Hydroxy-2-(3,4-methylenedioxybenzyl)-3-phenylpropionyl]-L-tryptophan methyl ester was obtained in substantially the same manner as that of Example 13-1).

The stereoisomers were separated by silica gel column chromatography (eluent; n-hexane:ethyl acetate=3:1) to give more polar isomer (90 mg) and less polar isomer (205 mg). The stereostructures of the more polar and the less polar isomers were assigned as (2S,3R)- and (2R,3S)-configurations respectively.

More Polar Isomer

NMR (CDCl$_3$, δ): 2.50–2.61 (2H, m), 2.88–3.07 (2H, m), 3.13–3.22 (1H, m), 3.57 (3H, s), 3.82 (1H, d, J=5 Hz), 4.76–4.86 (2H, m), 5.83–5.92 (3H, m), 6.52–6.58 (2H, m), 6.61 (1H, s), 6.67 (1H, d, J=8 Hz), 7.08 (1H, t, J=8 Hz), 7.17 (1H, t, J=8 Hz), 7.24–7.35 (7H, m), 7.98–8.03 (1H, br)

Less Polar Isomer

NMR (CDCl$_3$, δ): 2.50–2.58 (1H, m), 2.87–3.00 (3H, m), 3.14–3.21 (1H, m), 3.55 (3H, s), 3.59 (1H, d, J=5 Hz), 4.72–4.85 (2H, m), 5.78–5.85 (1H, m), 5.88 (2H, s), 6.23 (1H, d, J=2 Hz), 6.57–6.68 (3H, m), 7.03 (1H, d, J=8 Hz), 7.14 (1H, t, J=8 Hz), 7.23–7.38 (7H, m), 7.83–7.88 (1H, br)

The following compounds were obtained in substantially the same manner as that of Example 14-1)

Example 20-1)

N-[(2R,3S)-3-Hydroxy-2-(3,4-methylenedioxyphenyl)-3-phenylpropionyl]-L-tryptophan (124 mg)

NMR (CDCl$_3$, δ): 3.29 (2H, d, J=5 Hz), 4.88 (1H, dd, J=5, 14 Hz), 5.06 (1H, d, J=9 Hz), 5.83 (2H, d, J=7 Hz), 6.23 (1H, d, J=8 Hz), 6.33 (1H, dd, J=1, 8 Hz), 6.47 (1H, d, J=8 Hz), 6.53 (1H, d, J=1 Hz), 6.81 (1H, d, J=1 Hz), 7.06–7.23 (7H, m), 7.30 (1H, d, J=8 Hz), 7.47 (1H, d, J=8 Hz), 8.08–8.12 (1H, br)

FAB MS: 473.0 [M+H]+

Example 20-2)

N-[(2R,3S)-3-Hydroxy-2-(3,4-methylenedioxybenzyl)-3-phenylpropionyl]-L-tryptophan (165 mg)

NMR (CDCl₃, δ): 2.49–2.58 (1H, m), 2.69–2.80 (1H, m), 2.86–3.06 (2H, m), 3.15–3.24 (1H, m), 4.74–4.80 (2H, m), 5.80 (2H, s), 5.88–5.96 (1H, m), 6.43–6.60 (4H, m), 7.05 (1H, t, J=8 Hz), 7.18 (1H, t, J=8 Hz), 7.26–7.38 (8H, m), 7.95–7.98 (1H, br s)

FAB MS 487 [M+H]⁺

Example 21-1)

N-[(2S,3R)-3-Hydroxy-2-(3,4-methylenedioxyphenyl)-3-phenylpropionyl]-L-tryptophan (119 mg)

NMR (CDCl₃, δ): 3.20 (1H, dd, J=6, 14 Hz), 3.27 (1H, dd, J=7, 14 Hz), 3.43–3.51 (1H, m), 4.90–4.98 (1H, m), 5.07 (1H, d, J=9 Hz), 5.86, 5.90 (total 2H, s), 6.28 (1H, dd, J=1, 8 Hz), 6.46–6.52 (2H, m), 6.56 (1H, d, J=1 Hz), 6.71 (1H, d, J=1 Hz), 6.93–7.00 (3H, m), 7.06–7.16 (4H, m), 7.24 (1H, d, J=9 Hz), 7.29 (1H, d, J=9 Hz), 8.08–8.12 (1H, br)

FAB MS: 473.0 [M+H]⁺

Example 21-2)

N-[(2S,3R)-3-Hydroxy-2-(3,4-methylenedioxybenzyl)-3-phenylpropionyl]-L-tryptophan (81 mg)

NMR (CDCl₃, δ): 2.25–2.32 (1H, m), 2.50–2.59 (1H, m), 2.72–2.82 (1H, m), 2.94–3.02 (1H, m), 3.10–3.20 (1H, m), 4.70 (1H, d, J=8 Hz), 4.88–4.96 (1H, m), 5.83, 5.86 (total 2H, s), 6.28 (1H, t, J=8 Hz), 6.46 (1H, dd, J=1, 9 Hz), 6.52 (1H, s), 6.59–6.67 (2H, m), 7.08 (1H, t, J=8 Hz), 7.14–7.31 (9H, m), 8.08–8.12 (1H, br s)

FAB MS: 487 [M+H]⁺

Example 22

N-[(2RS,3SR)-3-Hydroxy-2-(3,4-methylenedioxyphenyl)-3-(4-carboxyphenyl)propionyl]-L-tryptophan (150 mg) was obtained from (2RS,3SR)-3-hydroxy-2-(3,4-methylenedioxyphenyl)-3-(4-carboxyphenyl)propionic acid in substantially the same manner as those of Examples 13-1) and 14-1).

NMR (DMSO-d₆, δ): 2.95–3.16 (3H, m), 3.87 (1H, dd, J=2, 10 Hz), 4.48–4.58 (1H, m), 5.08 (1H, d, J=10 Hz), 5.87–5.93 (2H, m), 6.50–6.66 (2H, m), 6.77–6.90 (2H, m), 6.96–7.10 (2H, m), 7.20–7.58 (4H, m), 7.69–7.75 (2H, m), 8.22–8.30 (1H, m)

FAB MS 517.2 [M+H]⁺

Example 23

A solution of N-[(2RS,3SR)-3-hydroxy-2-(3,4-methylenedioxyphenyl)-3-(2-n-butyl-1-tert-butyloxycarbonyl-1H-imidazol-4-yl)propionyl]-L-tryptophan methyl ester (118 mg) in 1N aqueous sodium hydroxide solution (1.0 ml) and methanol (5.0 ml) was stirred at ambient temperature for 2 hours. The solution was acidified with 1N hydrochloric acid and the mixture was diluted with ethyl acetate followed by washing with brine. The organic layer was dried and evaporated to afford crude N-[(2RS, 3SR)-3-hydroxy-2-(3,4-methylenedioxyphenyl)-3-(2-n-butyl-1-tert-butoxycarbonyl-1H-imidazol-4-yl)propionyl]-L-tryptophan.

A solution of the above crude product in trifluoroacetic acid (10 ml) was stirred at ambient temperature for 2 hours. The solvent was removed and to the residue was added 4N hydrogen chloride-ethyl acetate. Ethyl acetate was evaporated in vacuo and then the residue was solidified with ether. Resulting powder was collected by filtration and dried to afford N-[(2RS,3SR)-3-hydroxy-2-(3,4-methylenedioxyphenyl)-3-(2-n-butyl-1-tert-butoxycarbonyl-1H-imidazol-4-yl)propionyl]-L-tryptophan (68 mg).

FAB MS: 519.2 [M+H]⁺

Example 24

N-[(2RS,3SR)-3-Hydroxy-2-(3,4-methylenedioxyphenyl)-3-(2-n-butyl-1-tert-butyloxycarbonyl-1H-imidazol-4-yl)propionyl]-L-tryptophan was obtained from (2RS,3SR)-3-hydroxy-2-(3,4-methylenedioxyphenyl)-3-(2-n-butyl-1H-imidazol-4-yl) propionic acid hydrochloride in substantially the same manner as those of Examples 13-1) and 14-1).

FAB MS: 519.2 [M+H]⁺

The following compounds were obtained in substantially the same manner as that of Example 13-1).

Example 25-1)

[(2RS,3SR)-2-(3,4-Methylenedioxyphenyl)-3-hydroxyheptanoyl]-L-1-Nal-OBzl (830 mg)

NMR (DMSO-d₆, δ): 0.82 (3H, t, J=7 Hz), 1.02–1.42 (6H, m), 3.15–3.55 (3H, m), 3.83–4.00 (1H, m), 4.51–4.78 (2H, m), 4.85–5.12 (2H, m), 5.99, 6.02 (2H, s), 6.60–6.92 (3H, m), 6.95–7.40 (6H, m), 7.48–8.16 (5H, m), 8.51–8.65 (1H, m)

ESI-MS: 554 [M+H]

Example 25-2)

Nᵅ-[(2RS,3RS)-2-(3,4-Methylenedioxyphenyl)-3-hydroxyheptanoyl]-3-(benzo[b]thiophen-3-yl)-L-alanine Methyl Ester NMR (CDCl₃, δ): 0.83 (1.5H, t, J=7 Hz), 0.87 (1.5H, t, J=7 Hz), 1.13–1.53 (6H, m), 3.18–3.32 (2H, m), 3.32–3.47 (1H, m), 3.63 (1.5H, s), 3.68 (1.5H, s), 3.82 (0.5H, d, J=6 Hz), 3.87 (0.5H, d, J=6 Hz), 4.01–4.13 (1H, m), 4.87–5.00 (1H, m), 5.90–6.00 (2H, m), 6.05 (0.5H, d, J=8 Hz), 6.12 (0.5H, d, J=8 Hz), 6.53–6.60 (1H, m), 6.62–7.08 (3H, m), 7.28–7.42 (2H, m), 7.56–7.72 (1H, m), 7.79–7.78 (1H, m)

ESI-MS (m/z): 484 [M+H]

Example 25-3)

[(2R,3R)-2-(3,4-Methylenedioxyphenyl)-3-hydroxyheptanoyl]-L-Trp(Me)-OMe

NMR (CDCl₃, δ): 0.82 (3H, t, J=7 Hz), 1.13–1.52 (6H, m), 3.1–3.28 (3H, m), 3.65 (3H, s), 3.71 (3H, s), 4.00–4.13 (2H, m), 4.78–4.87 (1H, m), 5.92 (2H, s), 6.07 (1H, d, J=8 Hz), 6.52–6.58 (1H, m), 6.62–6.68 (2H, m), 6.72 (1H, s), 7.08 (1H, t, J=7 Hz), 7.27 (1H, d, J=6 Hz), 7.43 (1H, d, J=8 Hz)

ESI-MS (m/z): 481 [M+H]

Example 25-4)

[(2RS,3RS)-2-(3,4-Methylenedioxyphenyl)-3-hydroxyheptanoyl]-L-Trp(Me)-OMe

NMR (CDCl₃, δ): 0.78–0.83 (3H, m), 1.10–1.48 (9H, m), 3.10–3.30 (3H, m), 3.63 (1.5H, s), 3.67 (1.5H, s), 3.83–4.17 (4H, m), 4.78–4.93 (1H, m), 5.93 (1H, s), 5.97 (1H, s), 6.02–6.08 (1H, m), 6.39–6.80 (4H, m), 6.98–7.46 (4H, m)

ESI-MS (m/z): 495 [M+H]

Example 25-5)

[(2R,3R)-2-(3,4-Methylenedioxyphenyl)-3-hydroxyheptanoyl]-L-Trp(ⁱPr)-OMe

NMR (CDCl₃, δ): 0.82 (3H, t, J=7 Hz), 1.11–1.45 (6H, m), 1.46 (3H, d, J=7 Hz), 1.48 (3H, d, J=7 Hz), 3.19 (1H, d,

J=7 Hz), 3.26 (1H, d, J=6 Hz), 3.63 (3H, s), 4.01–4.15 (2H, m), 4.59 (0.5H, q, J=7 Hz), 4.62 (0.5H, q, J=7 Hz), 4.79–4.86 (1H, m), 5.92 (2H, s), 6.03 (1H, d, J=7 Hz), 6.52 (1H, d, J=7 Hz), 6.62 (1H, s), 6.65 (1H, d, J=6 Hz), 6.91 (1H, s), 7.08 (1H, t, J=7 Hz), 7.45 (1H, d, J=7 Hz)

ESI-MS (m/z): 509 [M+H]

Example 25-6)

[(2RS,3RS)-2-(3,4-Methylenedioxyphenyl)-3-hydroxyheptanoyl]-DL-Trp(5-Me)-OMe

NMR (CDCl$_3$, δ): 0.78–0.84 (3H, m), 1.10–1.47 (6H, m), 2.42 (1.5H, s), 2.46 (1.5H, s), 3.17–3.32 (3H, m), 3.66 (1.5H, s), 3.69 (1.5H, s), 3.89–4.08 (2H, m), 4.80–4.89 (1H, m), 5.92 (1H, s), 5.95 (1H, s), 6.03 (0.5H, d, J=7 Hz), 6.07 (0.5H, d, J=7 Hz), 6.52–6.86 (4H, m), 6.98–7.02 (1H, m), 7.20–7.27 (2H, m), 7.88 (0.5H, s), 7.97 (0.5H, s)

ESI-MS (m/z): 481 [M+H]

Example 25-7)

[(2R,3R)-2-(3,4-Methylenedioxyphenyl)-3-hydroxyheptanoyl]-DL-Trp(4-Me)-OMe

NMR (CDCl$_3$, δ): 0.82 (3H, t, J=7 Hz), 1.10–1.47 (6H, m), 2.63 (3H, s), 3.18–3.29 (2H, m), 3.48 (0.5H, d, J=6 Hz), 3.53 (0.5H, d, J=6 Hz), 3.68 (3H, s), 3.92–4.06 (2H, m), 4.78–4.85 (1H, m), 5.93 (2H, s), 6.02 (1H, d, J=7 Hz), 6.55 (1H, d, J=7 Hz), 6.63–6.68 (2H, m), 6.82–6.84 (2H, m), 7.07 (1H, t, J=7 Hz), 7.17 (1H, d, J=7 Hz), 8.02 (1H, s)

ESI-MS [M+H]

Example 25-8)

[(2R,3R)-2-(3,4-methylenedioxyphenyl)-3-hydroxyheptanoyl]-DL-Trp(6-Me)-OMe

NMR (CDCl$_3$, δ): 0.80–0.88 (3H, m), 1.12–1.48 (6H, m), 2.45 (3H, s), 3.17–3.27 (3H, m), 3.64 (3H, s), 4.00–4.08 (2H, m), 4.80–4.86 (1H, m), 5.92 (2H, s), 6.08 (1H, d, J=8 Hz), 6.62–6.93 (4H, m), 7.12 (1H, s), 7.34 (1H, d, J=7 Hz), 7.91 (1H, s)

ESI-MS (m/z) 481 [M+H]

Example 25-9)

[(2R,3R)-2-(3,4-methylenedioxyphenyl)-3-hydroxyheptanoyl]-DL-Trp(7-Me)-OMe

NMR (CDCl$_3$, δ): 0.83 (3H, t, J=7 Hz), 1.16–1.47 (6H, m), 2.47 (3H, s), 3.19–3.30 (3H, m), 3.65 (3H, s), 4.00–4.08 (2H, m), 4.80–4.87 (1H, m), 5.92 (2H, s), 6.08 (1H, d, J=7 Hz), 6.53–6.66 (3H, m), 6.91–7.06 (3H, m), 7.31 (1H, d, J=6 Hz), 7.97 (1H, s)

ESI-MS (m/z) 481 [M+H]

Example 25-10)

N$^\alpha$-[(2RS,3RS)-2-(3,4-Methylenedioxyphenyl)-3-hydroxyheptanoyl]-DL-7-azatryptophan Methyl Ester NMR (CDCl$_3$, δ): 0.77–0.84 (3H, m), 1.12–1.50 (6H, m), 3.18–3.37 (3H, m), 3.67 (1.5H, s), 3.68 (1.5H, s), 3.95–4.18 (2H, m), 4.88–4.98 (1H, m), 5.90–5.98 (2H, m), 6.32–7.04 (6H, m), 7.63 (0.5H, d, J=7 Hz), 7.80 (0.5H, d, J=7 Hz), 8.21–8.26 (1H, m), 9.60 (1H, s)

ESI-MS (m/z): 468 [M+H]

Example 25-11)

[(2RS,3RS)-2-(3,4-Methylenedioxyphenyl)-3-hydroxyheptanol]-L-Trp(CHO)-OBzl (248 mg)

NMR (CDCl$_3$, δ): 0.81, 0.84 (3H, t, J=7 Hz), 1.10–1.48 (6H, m), 3.14–3.27 (3H, m), 3.66–3.95 (1H, m), 4.02–4.13 (1H, m), 4.88–5.20 (3H, m), 5.93–5.98 (2H, s), 6.12–6.18 (1H, d, J=8 Hz), 6.53–6.75 (3H, m), 7.18–7.42 (5H, m), 8.28–8.72 (1H, m)

ESI-MS: 571 [M+H]

Example 25-12)

[(2RS,3RS)-2-(3,4-Methylenedioxyphenyl)-3-hydroxyheptanoyl]-L-Trp(COOMe)-OBzl (268 mg)

NMR (CDCl$_3$, δ): 0.79, 0.82 (3H, t, J=7 Hz), 1.07–1.50 (6H, m), 3.09, 3.25 (3H, m), 4.00 (3H, s), 4.02–4.12 (1H, m), 4.88–5.03 (1H, m), 5.04, 5.09 (2H, s), 5.88–5.96 (2H, m), 6.03–6.15 (1H, m), 6.49–6.68 (3H, m), 7.01–7.46 (10H, m), 8.08–8.19 (1H, m)

ESI-MS: 601 [M+H]

Example 25-13)

[(2RS,3RS)-2-(3,4-Methylenedioxyphenyl)-3-hydroxyheptanoyl]-L-Trp(CH$_2$CO$_2$Et)-OBzl NMR (CDCl$_3$, δ): 0.78 (1.5H, t, J=7 Hz), 0.82 (1.5H, t, J=7 Hz), 1.09–1.46 (8H, m), 1.26 (3H, t, J=8 Hz), 3.12–3.32 (3H, m), 3.96–4.08 (1H, m), 4.19 (2H, q, J=8 Hz), 4.61 (1H, s), 4.68 (1H, s), 4.87–5.02 (1H, m), 5.03–5.12 (2H, m), 5.88–5.98 (2H, m), 6.13–6.74 (5H, m), 6.98–7.48 (8H, m)

ESI-MS (m/z): 629 [M+H]

Example 25-14)

[(2R,3R)-2-(3,4-Methylenedioxyphenyl)-3-hydroxyheptanoyl]-L-Trp(CH$_2$CONMe$_2$)-OMe NMR (CDCl$_3$, δ): 0.80 (3H, t, J=7 Hz), 1.12–1.47 (6H, m), 2.98 (3H, s), 3.06 (3H, s), 3.21–3.37 (3H, m), 3.67 (3H, s), 3.95–4.08 (2H, m), 4.82–4.90 (3H, m), 5.91 (2H, s), 6.48 (1H, d, J=7 Hz), 6.57–6.67 (2H, m), 6.72 (1H, s), 6.90 (1H, s), 7.07–7.13 (1H, m), 7.18–7.20 (2H, m), 7.48 (1H, d, J=7 Hz)

ESI-MS (m/z): 552 [M+H]

Example 25-15)

[(2R,3R)-3-Hydroxy-2-(3,4-methylenedioxyphenyl)-heptanoyl]-L-Trp(CH$_2$CH$_2$CO$_2$Et)-OMe NMR (CDCl$_3$, δ): 0.83 (3H, t, J=8 Hz), 1.17–1.31 (6H, m), 1.20 (3H, t, J=8 Hz), 2.77 (2H, t, J=8 Hz), 3.22–3.28 (3H, m), 3.67 (3H, s), 4.04–4.14 (4H, m), 4.38 (2H, t, J=8 Hz), 4.82 (1H, dd, J=6, 14 Hz), 5.94 (2H, s), 6.11 (1H, d, J=8 Hz), 6.54–6.58 (1H, m), 6.64–6.67 (2H, m), 6.87 (1H, s), 7.09 (1H, t, J=8 Hz), 7.21 (1H, dd, J=6, 7 Hz), 7.26–7.32 (1H, m), 7.44 (1H, d, J=8 Hz)

ESI-MS: 567 [M+H]

Example 25-16)

[3-(1-t-Butoxycarbonyl-2-pentylimidazol-4-yl)-2-(3,4-methylenedioxyphenyl)propionyl]-L-Trp(CH$_2$CO$_2$$^t$Bu)-OBzl was obtained according to a similar manner to that of Example 25-27).

NMR (CDCl$_3$, δ): 0.85–0.92 (3H, m), 1.24–1.38 (4H, m), 1.42 (9H, s), 1.50 (4.5H, s), 1.53 (4.5H, s), 1.55–1.72 (2H, m), 2.77–2.97 (3H, m), 3.08–3.32 (3H, m), 3.73–3.80 (1H, m), 4.49 (1H, s), 4.56 (1H, s), 4.86–4.93 (1H, m), 4.95 (1H, s), 5.00 (1H, s), 5.87–5.97 (2H, m), 6.13–7.43 (15H, m)

ESI-MS (m/z): 821 [M+H]

The following compounds were obtained in substantially the same manner as that of Example 13-1).

Example 25-17)

N$^\alpha$-[3-Hydroxy-3,3-di(2-pyridyl)-2-(3,4-methylenedioxyphenyl)propionyl]-L-tryptophan Methyl Ester NMR (CDCl$_3$, δ): 2.98–3.09 (1H, m), 3.13–3.18 (1H, m), 3.47, 3.57 (total 3H, s), 4.69–4.80 (1H, m), 5.22 (1H, d, J=8 Hz), 5.81–5.88 (2H, m), 6.39–6.68 (3H, m), 6.77–6.84 (2H, m), 6.92–7.76 (9H, m), 7.94–8.09 (2H, m), 8.36 (1H, t, J=6 Hz), 8.43–8.47 (1H, br s)

ESI-MS: 565 [M+H]

Example 25-18)

N$^\alpha$-[(2RS,3RS)-2-(3,4-Methylenedioxyphenyl)-3-cyclopropyl-3-hydroxypropionyl]-L-tryptophan Methyl Ester NMR (CDCl$_3$, δ): −0.10–0.02 (1H, m), 0.15–0.45 (3H, m), 0.62–0.82 (1H, m), 3.20–3.26 (1H, m), 3.30 (1H, t, J=6 Hz), 3.33–3.50 (2H, m), 3.67 (1.5H, s), 3.70 (1.5H, s), 3.80–3.92 (1H, m), 4.87–4.98 (1H, m), 5.92 (1H, s), 5.97 (1H, s), 6.18 (0.5H, d, J=7 Hz), 6.27 (0.5H, d, J=7 Hz), 6.60–7.50 (8H, m), 8.01 (0.5H, s), 8.09 (0.5H, s)

ESI-MS (m/z): 451 [M+H]

Example 25-19)

N$^\alpha$-[(2RS,3RS)-3-Hydroxy-3-(2-biphenylyl)-2-(3,4-methylenedioxyphenyl)propionyl]-L-tryptophan Methyl Ester NMR (CDCl$_3$, δ): 3.13–3.22 (3H, m), 3.42–3.56 (2H, m), 3.60 (1.5H, s), 3.67 (1.5H, s), 4.63 (0.5H, d, J=5 Hz), 4.78–4.87 (1H, m), 5.06 (0.5H, d, J=6 Hz), 5.26–5.33 (1H, m), 5.85 (1H, d, J=4 Hz), 5.88–5.95 (2H, m), 6.00 (1H, dd, J=2, 8 Hz), 6.11 (1H, s), 6.42 (1H, d, J=8 Hz), 6.47 (0.5H, d, J=2 Hz), 6.61 (0.5H, d, J=2 Hz), 6.92–7.40 (10H, m), 7.60 (0.5H, d, J=8 Hz), 7.69 (0.5H, d, J=8 Hz), 7.83–7.86 (0.5H, br s), 7.97–8.00 (0.5H, br s)

Example 25-20)

[(2R,3R)-2-(3,4-Methylenedioxyphenyl)-3-hydroxyoctanoyl]-L-Trp-OMe (248 mg) as a less polar isomer was obtained according to a similar manner to that of Example 13-1) by using silica gel column chromatography (hexane:AcOEt=1:1).

Rf: 0.51 (silica gel, hexane:AcOEt=1:1)

NMR (CDCl$_3$, δ): 0.82 (3H, t, J=7 Hz), 1.08–1.52 (8H, m), 3.20 (1H, d, J=8 Hz), 3.28 (2H, t, J=7 Hz), 3.65 (3H, s), 4.00–4.08 (1H, m), 4.81–4.89 (1H, m), 5.92 (2H, s), 6.09 (1H, d, J=9 Hz), 6.54 (1H, d, J=8 Hz), 6.65 (1H, s), 6.67 (1H, d, J=9 Hz), 6.91 (1H, d, J=3 Hz), 7.11 (1H, t, J=7 Hz), 7.20 (1H, t, J=7 Hz), 7.34 (1H, d, J=9 Hz), 7.48 (1H, d, J=9 Hz), 8.07 (1H, s)

ESI-MS: 481 [M+H]

The following compounds were obtained in substantially the same manner as that of Example 13-1).

Example 25-21)

[(2RS,3SR)-2-(3,4-Methylenedioxyphenyl)-3-hydroxyoctanoyl]-L-Trp(CH$_2$COOEt)-OBzl (448 mg)

NMR (CDCl$_3$, δ): 0.84, 0.87 (3H, t, J=7 Hz), 1.25 (1H, t, J=8 Hz), 1.05–1.48 (8H, m), 3.10–3.32 (3H, m), 3.78–4.08 (2H, m), 4.20 (1H, q, J=8 Hz), 4.62 (2H, dd, J=2, 15 Hz), 4.85–5.01 (1H, m), 5.02–5.13 (2H, m), 5.86–5.99 (2H, m), 6.15–6.55 (2H, m), 6.57–6.75 (3H, m), 6.98–7.48 (9H, m)

ESI-MS: 643 [M+H]

Example 25-22)

[(2RS,3SR)-2-(3,4-Methylenedioxyphenyl)-3-hydroxyoctanoyl]-L-1-Nal-OBzl(532 mg)

NMR (DMSO-d$_6$, δ): 0.82 (3H, t, J=7 Hz), 0.93–1.40 (8H, m), 3.20–3.53 (3H, m), 3.82–3.96 (1H, m), 4.55–4.76 (2H, m), 4.82–5.10 (2H, m), 5.97, 6.00 (2H, s), 6.63–6.88 (3H, m), 6.98–7.05 (1H, m), 7.12–7.38 (5H, m), 7.45–7.60 (2H, m), 7.68–8.13 (3H, m), 8.54–8.62 (1H, m)

ESI-MS: 568 [M+H]

Example 25-23)

[(2R,3R)-2-(3,4-Methylenedioxyphenyl)-3-hydroxyoctanoyl]-L-Trp(CH$_2$COOEt)-NHSO$_2$CH$_3$ (170 mg) as a less polar isomer was obtained according to a similar manner to that of Example 13-1) by using silica gel thin layer chromatography (10%-MeOH in CHCl$_3$).

Rf: 0.50 (10% MeOH in CHCl$_3$)

NMR (DMSO-d$_3$, δ): 0.80 (3H, t, J=7 Hz), 0.98–1.42 (8H, m), 1.20 (3H, t, J=7 Hz), 2.98–3.18 (2H, m), 3.01 (3H, s), 3.32–3.48 (1H, m), 3.87–4.00 (1H, m), 4.15 (2H, q, J=8 Hz), 4.53–4.66 (1H, m), 4.72–4.87 (1H, m), 5.02 (2H, m), 5.97 (2H, s), 6.72 (1H, d, J=7 Hz), 6.80 (1H, d, J=7 Hz), 6.86 (1H, s), 6.89–7.25 (3H, m), 7.32 (1H, d, J=7 Hz), 7.63 (1H, d, J=7 Hz), 8.28 (1H, d, J=7 Hz)

ESI-MS: 630 [M+H]

Example 25-24)

To a solution of 3-(1-tert-butoxycarbonyl-2-n-butylimidazol-4-yl)-2-(3,4-methylenedioxyphenyl) propionic acid (250 mg), L-tryptophan benzyl ester hydrochloride (209 mg) and triethylamine (128 mg) in N,N-dimethylformamide (5 ml) was added diphenylphosphoryl azide (198 mg) and the mixture was stirred at ambient temperature for 5.5 hours. The resulting mixture was diluted with ethyl acetate and the organic layer was washed successively with 0.5N hydrogen chloride aqueous solution, saturated sodium bicarbonate aqueous solution and brine. Drying, filtering and removal of the solvents afforded a crude product. The crude product was chromatographed on silica gel (eluent; n-hexane:ethyl acetate=1:2) to give [3-(1-tert-butoxycarbonyl-2-n-butylimidazol-4-yl)-2-(3,4-methylenedioxyphenyl)propionyl]-L-tryptophan benzyl ester (125 mg) as a yellow oil.

Rf: 0.47 (benzene:ethyl acetate:acetic acid=20:20:1)

ESI-MS: 693 [M+H]

The following compounds were obtained in substantially the same manner as that of Example 25-27).

Example 25-25)

N$^\alpha$-[3-(1-tert-Butoxycarbonyl-2-n-butylimidazol-4-yl)-2-(3,4-methylenedioxyphenyl)propionyl]-L-tryptophan Ethyl Ester NMR (CDCl$_3$, δ): 0.88–0.96 (3H, m), 1.04–1.18 (3H, m), 1.33–1.41 (2H, m), 1.52, 1.56 (total 9H, s), 1.58–1.68 (2H, m), 2.78–2.98 (3H, m), 3.15–3.30 (3H, m), 3.74–3.80 (1H, m), 3.95–4.16 (3H, m), 4.80–4.89 (1H, m), 5.90–5.97 (2H, m), 6.12–6.18 (1H, m), 6.65–6.70 (2H, m), 6.78–6.95 (2H, m), 6.99–7.19 (2H, m), 7.28–7.49 (2H, m), 7.94–8.03 (1H, m)

ESI-MS: 631 [M+H]

Example 25-26)

N-[(2RS)-3-(1-tert-Butoxycarbonyl-2-n-butylimidazol-4-yl)-2-(3,4-methylenedioxyphenyl)propionyl]-L-3-(1-naphthyl)alanine benzyl ester (2R:2S=1:4)

NMR (CDCl$_3$, δ): 0.95 (3H, t, J=8 Hz), 1.30–1.42 (2H, m), 1.48, 1.56 (total 9H, s), 1.60–1.70 (2H, m), 2.79–2.98 (3H, m), 3.20–3.32 (2H, m), 3.40–3.57 (2H, m), 3.80 (1H, t, J=8 Hz), 4.83 (1H, d, J=11 Hz), 4.91 (1H, d, J=11 Hz), 4.92–5.00 (1H, rn), 5.89–5.96 (2H, m), 6.29 (1H, d, J=8 Hz), 6.63–6.70 (2H, m), 6.82–7.07 (4H, m), 7.19–7.31 (4H, m), 7.42–7.53 (2H, m), 7.66–7.71 (1H, m), 7.79–7.85 (1H, m), 8.10 (1H, d, J=8 Hz)

ESI-MS: 704 [M+H]

Example 25-27)

To a solution of (2RS)-3-(1-tert-butoxycarbonyl-2-n-butylimidazol-4-yl)-2-(3,4-methylenedioxyphenyl) propionic acid (2R:2S=1:4, 250 mg) and HCl.H-L-Trp (CH$_2$CO$_2$Et)-OBzl (250 mg) in dichloromethane (8 ml) was added portionwise water soluble carbodiimide (WSCD) (112 mg) at 0° C. and the mixture was stirred at ambient temperature for 2 hours. The resulting solution was diluted with dichloromethane followed by washing successively with saturated ammonium chloride aqueous solution and saturated sodium bicarbonate aqueous solution. Drying, filtering and removal of the solvents afforded a crude product. The crude product was chromatographed on silica gel (eluent; n-hexane:ethyl acetate=1:1) to give [(2RS)-3-(1-tert-butoxycarbonyl-2-n-butylimidazol-4-yl)-2-(3,4-methylenedioxyphenyl)propionyl]-L-Trp(CH$_2$CO$_2$Et)-OBzl (2R:2S=1:4) (305 mg) as a white amorphous powder.

NMR (CDCl$_3$, δ): 0.93 (3H, t, J=8 Hz), 1.24 (3H, t, J=8 Hz), 1.32–1.42 (2H, m), 1.53, 1.58 (total 9H, s), 1.60–1.70 (2H, m), 2.80–2.97 (3H, m), 3.08–3.17 (1H, m), 3.20–3.31 (2H, m), 3.79 (1H, t, J=8 Hz), 4.18 (2H, q, J=8 Hz), 4.57, 4.66 (total 2H, s), 4.87–4.97 (1H, m), 4.96, 5.01 (total 2H, s), 5.88–5.97 (2H, m), 6.17–6.23 (1H, m), 6.48–6.93 (3H, m), 7.04–7.34 (10H, m), 7.42 (1H, d, J=8 Hz)

ESI-MS: 779 [M+H]

The following compounds were obtained in substantially the same manner as that of Example 25-27).

Example 25-28)

[(2RS)-3-(1-tert-Butoxycarbonyl-2-n-butylimidazol-4-yl)-2-(3,4-methylenedioxyphenyl)propionyl]-L-Trp (CH$_2$CH$_2$CO$_2$Et)-OBzl (2R:2S=1:4)

NMR (CDCl$_3$, δ): 0.89–0.95 (3H, m), 1.16–1.23 (3H, m), 1.30–1.42 (2H, m), 1.53, 1.56 (total 9H, s), 1.57–1.69 (2H, m), 2.60–2.69 (2H, m), 2.80–2.97 (3H, m), 3.06–3.32 (3H, m), 3.80 (1H, t, J=8 Hz), 4.06–4.17 (3H, m), 4.27 (1H, t, J=7 Hz), 4.85–4.97 (1H, m), 4.96, 5.02 (total 2H, s), 5.87–5.97 (2H, m), 6.18–6.25 (1H, m), 6.57–6.67 (2H, m), 6.72–6.93 (2H, m), 7.02–7.12 (2H, m), 7.16–7.35 (7H, m), 7.42 (1H, d, J=8 Hz)

ESI-MS 793 [M+H]

Example 25-29)

[(2RS)-3-(1-tert-Butoxycarbonyl-2-n-butylimidazol-4-yl)-2-(3,4-methylenedioxyphenyl)propionyl]-L-Trp(Me)-OBzl (2R:2S=1:4)

NMR (CDCl$_3$, δ): 0.88–0.96 (3H, m), 1.30–1.44 (2H, m), 1.52, 1.58 (total 9H, s), 1.60–1.72 (2H, m), 2.80–2.97 (3H, m), 3.07–3.32 (3H, m), 3.56, 3.62 (total 3H, s), 3.74–3.81 (1H, m), 4.86–4.93 (1H, m), 4.97, 5.03 (total 2H, s), 5.88–6.05 (2H, m), 6.12–6.19 (1H, m), 6.59–6.67 (2H, m), 6.72–7.33 (11H, m), 7.42 (1H, d, J=8 Hz)

ESI-MS: 707 [M+H]

Example 25-30)

[(2RS)-3-(1-tert-Butoxycarbonyl-2-n-butylimidazol-4-yl)-2-(3,4-methylenedioxyphenyl)propionyl]-L-Trp (CH$_2$CO$_2$Bzl)-OBzl (2R:2S=1:4)

NMR (CDCl$_3$, δ): 0.88–0.95 (3H, m), 1.30–1.40 (2H, m), 1.53, 1.62 (total 9H, s), 1.59–1.69 (2H, m), 2.78–2.96 (3H, m), 3.09–3.30 (3H, m), 3.74–3.80 (1H, m), 4.60, 4.69 (total 2H, s), 4.86–5.00 (3H, m), 5.16 (2H, s), 5.86–5.89 (2H, m), 6.25 (1H, d, J=8 Hz), 6.48 (1H, s), 6.58–6.68 (2H, m), 6.78, 6.82 (total 1H, s), 6.88, 6.90 (total 1H, s), 7.06–7.35 (13H, m), 7.44 (1H, d, J=8 Hz)

ESI-MS: 841 [M+H]

Example 25-31)

[(2RS)-3-(1-tert-Butoxycarbonyl-2-n-butylimidazol-4-yl)-2-(3,4-methylenedioxyphenyl)propionyl]-L-Trp (CH$_2$CO$_2^t$Bu)-OBzl (2R:2S=1:4)

NMR (CDCl$_3$, δ): 0.89–0.96 (3H, m), 1.32–1.40 (2H, m), 1.45, 1.57 (total 9H, s), 1.55, 1.63 (total 9H, s), 1.64–1.70 (2H, m), 2.84–2.97 (3H, m), 3.09–3.30 (3H, m), 3.75–3.80 (1H, m), 4.47, 4.56 (total 2H, s), 4.86–4.95 (1H, m), 4.96, 5.02 (total 2H, s), 5.87–5.96 (2H, m), 6.13–6.22 (1H, m), 6.50–6.90 (5H, m), 7.05–7.42 (4H, m)

ESI-MS: 807 [M+H]

Example 25-32)

[(2RS)-3-(1-tert-Butoxycarbonyl-2-n-butylimidazol-4-yl)-2-(3,4-methylenedioxyphenyl)propionyl]-L-Trp(Et)-OBzl (2R:2S=1:4)

Rf: 0.75 (10% methanol in chloroform)

Example 25-33)

N$^α$-[3-(1-Triphenylmethylimidazol-4-yl)-2-(3,4-methylenedioxyphenyl)propionyl]-L-tryptophan Benzyl Ester NMR (CDCl$_3$, δ): 2.85–2.94 (1H, m), 3.13–3.30 (3H, m), 3.70–3.80 (1H, m), 4.87–4.96 (1H, m), 4.95, 5.00 (total 2H, s), 5.89, 5.93 (total 2H, s), 6.24–6.47 (2H, m), 6.53–6.75 (3H, m), 6.97–7.00 (6H, m), 7.07–7.32 (20H, m), 7.87–7.95 (1H, m)

ESI-MS: 779 [M+H]

Example 25-34)

N$^α$-[3-(1-Methylimidazol-5-yl)-2-(3,4-methylenedioxyphenyl)propionyl]-L-tryptophan Benzyl Ester NMR (CDCl$_3$, δ): 2.78–2.88 (1H, m), 3.19–3.26 (2H, m), 3.36–3.50 (4H, m), 4.83–4.92 (1H, m), 5.05, 5.08 (total 2H, s), 5.90–5.96 (2H, m), 6.01–6.07 (1H, m), 6.38–6.40 (1H, m), 6.56–6.73 (4H, m), 6.98–7.40 (11H, m), 8.27–8.30 (1H, br)

ESI-MS: 551 [M+H]

Example 25-35)

N$^α$-[3-(1-t-Butoxycarbonyl-2-ethylimidazol-4-yl)-2-(3,4-methylenedioxyphenyl)propionyl]-L-tryptophan benzyl ester NMR (CDCl$_3$, δ): 1.22–1.30 (3H, m), 1.52 (4.5H, s), 1.55 (4.5H, s), 2.78–2.99 (3H, m), 3.10–3.33 (3H, m), 3.74–3.80 (1H, m), 4.85–5.01 (3H, m), 5.88–5.94 (2H, m), 6.18–6.24 (1H, m), 6.60–7.33 (13H, m), 7.45 (1H, d, J=7 Hz), 7.90 (0.5H, s), 7.98 (0.5H, s)

ESI-MS (m/z): 665 [M+H]

Example 25-36)

N$^α$-[(2RS)-3-(1-tert-Butoxycarbonyl-2-n-propylimidazol-4-yl)-2-(3,4-methylenedioxyphenyl) propionyl]-L-tryptophan Benzyl Ester (2R:2S=1:4)

NMR (CDCl₃, δ): 0.97 (3H, t, J=8 Hz), 1.53, 1.56 (total 9H, s), 1.65–1.75 (2H, m), 2.79–2.98 (3H, m), 3.02–3.31 (3H, m), 3.79 (1H, t, J=9 Hz), 4.87–4.95 (1H, m), 4.96, 5.02 (total 2H, s), 5.88–5.95 (2H, m), 6.20 (1H, d, J=8 Hz), 6.60–6.70 (2H, m), 6.79–6.95 (2H, m), 7.03–7.20 (3H, m), 7.26–7.35 (5H, m), 7.45 (1H, d, J=8 Hz), 7.95–7.99 (1H, br s)

ESI-MS: 679 [M+H]

Example 25-37)

N$^\alpha$-[3-(1-t-Butoxycarbonyl-2-pentylimidazol-4-yl)-2-(3,4-methylenedioxyphenyl)propionyl]-L-tryptophan Benzyl Ester NMR (CDCl₃, δ): 0.87–0.93 (3H, m), 1.23–1.38 (4H, m), 1.50 (4.5H, s), 1.54 (4.5H, s), 1.60–1.79 (2H, m), 2.79–2.98 (3H, m), 3.10–3.32 (3H, m), 3.72–3.81 (1H, m), 4.70–5.02 (3H, m), 5.87–5.95 (2H, m), 6.16–6.21 (1H, m), 6.40–7.45 (14H, m), 7.87 (0.5H, s), 7.95 (0.5H, s)

ESI-MS (m/z): 707 [M+H]

Example 25-38)

[(2RS,3RS)-2-(3,4-Methylenedioxyphenyl)-3-hydroxyheptanoyl]-L-Trp(CHO)-NHSO₂CH₃ (245 mg)

NMR (CDCl₃, δ): 0.73–0.90 (3H, m), 1.09–1.49 (6H, m), 3.03–3.45 (3H, m), 3.11, 3.38 (3H, s), 4.00–4.19 (1H, m), 4.62–4.92 (1H, m), 5.91–5.99 (2H, m), 6.28 (1H, d, J=8 Hz), 6.52–6.79 (3H, m), 6.82–7.50 (5H, m), 8.23–8.27 (1H, s)

ESI-MS: 530 [M+H]

The compounds of Examples 26-1) to 3), 14) to 16), 22) to 24), and 26) to 34) were obtained in substantially the same manner as that of Example 7-1). And the compounds of Examples 26-4) to 13), and 17) to 21) were obtained in substantially the same manner as that of 14-1).

Example 26-1)

N$^\alpha$-[(2RS,3RS)-2-(3,4-Methylenedioxyphenyl)-3-acetoxyheptanoyl]-L-tryptophan NMR (CDCl₃, δ): 0.73–0.83 (3H, m), 1.03–1.50 (6H, m), 1.81 (1.5H, s), 1.90 (1.5H, s), 3.08–3.48 (3H, m), 4.73–4.90 (1H, m), 5.40–5.53 (1H, m), 5.83–5.96 (2H, m), 6.22–7.33 (10H, m), 8.33–8.46 (1H, m)

ESI-MS (m/z): 495 [M+H]

Example 26-2)

[(2R,3R)-2-(3,4-Methylenedioxyphenyl)-3-hydroxyoctanoyl]-L-1-Nal-OH (148 mg) [a less polar isomer, obtained by using preparative thin layer chromatography (CHCl₃:MeOH:AcOH=20:1:1)]

mp: 183–184° C.

Rf: 0.71 (CHCl₃:MeOH:AcOH=16:1:1)

NMR (DMSO-d₆, δ): 0.80 (3H, t, J=7 Hz), 0.94–1.42 (8H, m), 3.20–3.52 (4H, m), 3.79–3.92 (1H, m), 4.50–4.60 (1H, m), 5.98 (2H, s), 6.72 (1H, d, J=8 Hz), 6.82 (1H, d, J=8 Hz), 6.87 (1H, s), 7.32–7.42 (2H, m), 7.50–7.63 (2H, m), 7.81 (1H, d, J=8 Hz), 7.94 (1H, d, J=8 Hz), 8.18 (1H, d, J=8 Hz), 8.39 (1H, d, J=8 Hz)

ESI-MS: 478 [M+H]

Example 26-3)

N$^\alpha$-[3-(1-t-Butoxycarbonyl-2-pentylimidazol-4-yl)-2-(3,4-methylenedioxyphenyl)propionyl]-L-tryptophan P NMR (CDCl₃, δ): 0.84–0.92 (3H, m), 1.18–1.38 (4H, m), 1.40–1.67 (11H, m), 2.75–3.43 (6H, m), 3.98–4.08 (1H, m), 4.73–4.97 (1H, m), 5.87–5.97 (2H, m), 6.53–7.58 (9H, m), 7.63–7.90 (1H, m)

ESI-MS (m/z): 617 [M+H]

Example 26-4)

N$^\alpha$-[(2RS,3RS)-2-(3,4-Methylenedioxyphenyl)-3-hydroxyheptanoyl]-3-(benzo[b]thiophen-3-yl)-L-alanine NMR (DMSO-d₆, δ): 0.77 (3H, t, J=6 Hz), 0.97–1.40 (6H, m), 3.00–3.48 (5H, m), 3.87–3.98 (1H, m), 4.49–4.65 (1H, m), 5.98 (2H, s), 6.68–7.48 (6H, m), 7.70–8.00 (2H, m), 8.35 (1H, t, J=7 Hz)

ESI-MS (m/z): 470 [M+H]

Example 26-5

N$^\alpha$-[(2RS,3RS)-2-(3,4-Methylenedioxyphenyl)-3-hydroxyheptanoyl]-3-(benzo[b]thiophen-1,1-dioxide-3-yl)-L-alanine NMR (DMSO-d₆, δ): 0.63–0.95 (3H, m), 0.97–1.50 (6H, m), 2.93–3.70 (4H, m), 3.82–4.07 (1H, m), 4.10–4.36 (1H, m), 4.93–5.12 (1H, m), 5.82–6.17 (2H, m), 6.50–8.10 (8H, m), 8.45–8.70 (1H, m)

ESI-MS (m/z): 502 [M+H]

Example 26-6)

[(2R,3R)-2-(3,4-Methylenedioxyphenyl)-3-hydroxyheptanoyl]-L-Trp(Me)-OH

NMR (CDCl₃, δ): 0.80 (3H, t, J=7 Hz), 1.10–1.50 (6H, m), 3.20 (1H, d, J=8 Hz), 3.25–3.32 (2H, m), 3.69 (3H, s), 3.98–4.08 (1H, m), 4.72–4.82 (1H, m), 5.90 (1H, s), 5.91 (1H, s), 6.16 (1H, d, J=7 Hz), 6.48 (1H, d, J=8 Hz), 6.57–6.63 (2H, m), 6.76 (1H, s), 7.07 (1H, t, J=7 Hz), 7.18–7.28 (2H, m), 7.48 (1H, d, J=7 Hz)

ESI-MS (m/z): 467 [M+H]

Example 26-7

[(2RS,3RS)-2-(3,4-Methylenedioxyphenyl)-3-hydroxyheptanoyl]-L-Trp(Et)-OH

NMR (CDCl₃, δ): 0.79 (1.5H, t, J=7 Hz), 0.80 (1.5H, t, J=7 Hz), 1.05–1.47 (9H, m), 3.15–3.30 (3H, m), 3.97–4.10 (3H, m), 4.73–4.89 (1H, m), 5.89–5.97 (2H, m), 6.17 (0.5H, d, J=7 Hz), 6.30 (0.5H, d, J=7 Hz), 6.45–6.83 (4H, m), 6.97–7.50 (4H, m)

ESI-MS (m/z): 481 [M+H]

Example 26-8)

[(2R,3R)-2-(3,4-Methylenedioxyphenyl)-3-hydroxyheptanoyl]-L-Trp($^i$Pr)-OH

NMR (CDCl₃, δ): 0.81 (3H, t, J=7 Hz), 1.08–1.45 (6H, m), 1.45 (3H, d, J=7 Hz), 1.48 (3H, d, J=7 Hz), 3.18 (1H, d, J=7 Hz), 3.20–3.37 (2H, m), 3.98–4.05 (1H, m), 4.58 (0.5H, q, J=7 Hz), 4.60 (0.5H, q, J=7 Hz), 4.77–4.82 (1H, m), 5.90 (2H, s), 6.13 (1H, d, J=7 Hz), 6.46 (1H, d, J=7 Hz), 6.56 (1H, s), 6.60 (1H, d, J=6 Hz), 6.98 (1H, s), 7.06 (1H, t, J=7 Hz), 7.18 (1H, t, J=7 Hz), 7.32 (1H, d, J=7 Hz), 7.48 (1H, d, J=8 Hz)

ESI-MS (m/z): 495 [M+H]

Example 26-9)

[(2RS,3RS)-2-(3,4-Methylenedioxyphenyl)-3-hydroxyheptanoyl]-DL-Trp(5-Me)-OH

NMR (CDCl₃, δ): 0.74–0.83 (3H, m), 1.07–1.48 (6H, m), 2.40 (1.5H, s), 2.45 (1.5H, s), 3.15–3.37 (3H, m), 4.00–4.10

(1H, m), 4.75–4.88 (1H, m), 5.85–5.92 (2H, m), 6.29–6.83 (5H, m), 7.00–7.03 (1H, m), 7.18–7.31 (2H, m), 8.08–8.19 (1H, s)

ESI-MS (m/z): 467 [M+H]

Example 26-10)

[(2R,3R)-2-(3,4-Methylenedioxyphenyl)-3-hydroxyheptanoyl]-DL-Trp(4-Me)-OH

NMR (CDCl$_3$, δ): 0.74–0.82 (3H, m), 1.08–1.48 (6H, m), 2.60 (3H, s), 3.15–3.33 (2H, m), 3.50–3.60 (1H, m), 3.94–4.07 (1H, m), 4.68–4.80 (1H, m), 5.86–5.92 (2H, m), 6.25–6.38 (1H, m), 6.45–6.53 (1H, m), 6.55–6.63 (2H, m), 6.79–6.82 (2H, m), 7.05 (1H, t, J=7 Hz), 7.17 (1H, d, J=7 Hz), 8.22 (1H, s)

ESI-MS (m/z): 467 [M+H]

Example 26-11)

[(2R,3R)-2-(3,4-Methylenedioxyphenyl)-3-hydroxyheptanoyl]-DL-Trp(6-Me)-OH

NMR (CDCl$_3$, δ): 0.78–0.87 (3H, m), 1.03–1.48 (6H, m), 2.42 (3H, s), 3.17–3.33 (3H, m), 3.98–4.07 (1H, m), 4.77–4.83 (1H, m), 5.88 (1H, s), 5.90 (1H, s), 6.23 (1H, d, J=7 Hz), 6.48 (1H, d, J=7 Hz), 6.59–6.82 (3H, m), 6.91 (1H, d, J=7 Hz), 7.10 (1H, s), 7.38 (1H, d, J=7 Hz), 8.03 (1H, s)

ESI-MS (m/z): 467 [M+H]

Example 26-12)

[(2R,3R)-2-(3,4-Methylenedioxyphenyl)-3-hydroxyheptanoyl]-DL-Trp(7-Me)-OH

NMR (CDCl$_3$+CD$_3$OD, δ): 0.80–0.85 (3H, m), 1.10–1.50 (6H, m), 2.47 (3H, s), 3.18–3.43 (3H, m), 3.98–4.08 (1H, m), 4.73–4.83 (1H, m), 5.90–5.93 (2H, m), 6.52–6.67 (4H, m), 6.93–7.05 (3H, m), 7.25–7.40 (2H, m)

ESI-MS (m/z): 467 [M+H]

Example 26-13)

N$^α$-[(2RS,3RS)-2-(3,4-Methylenedioxyphenyl)-3-hydroxyheptanoyl]-DL-7-azatryptophan NMR (DMSO-d$_6$, δ): 0.76 (3H, t, J=6 Hz), 0.97–1.40 (6H, m), 2.95–3.15 (2H, m), 3.46–3.50 (1H, m), 3.90–3.97 (1H, m), 4.45–4.55 (1H, m), 5.96–5.99 (2H, m), 6.70–7.32 (6H, m), 7.70 (0.5H, d, J=7 Hz), 7.93 (0.5H, d, J=7 Hz), 8.10–8.17 (2H, m)

ESI-MS (m/z): 454 [M+H]

Example 26-14)

[(2RS,3RS)-2-(3,4-Methylenedioxyphenyl)-3-hydroxyheptanoyl]-L-Trp(CHO)-OH (152 mg)

NMR (CDCl$_3$, δ): 0.79, 0.80 (3H, t, J=7 Hz), 1.05–1.48 (6H, m), 3.02–3.38 (4H, m), 4.02–4.16 (1H, m), 4.71–4.95 (1H, m), 5.89–5.98 (2H, s), 6.52–6.85 (5H, m), 7.00–7.62 (4H, m), 8.22–8.95 (1H, m)

ESI-MS: 481 [M+H]

Example 26-15)

[(2RS,3RS)-2-(3,4-Methylenedioxyphenyl)-3-hydroxyheptanoyl]-L-Trp(COOMe)-OH (206 mg)

NMR (CDCl$_3$, δ): 0.72–0.85 (3H, m), 1.08–1.50 (6H, m), 3.00–3.24 (3H, m), 3.97, 3.99 (3H, s), 4.02–4.13 (1H, m), 4.73–4.96 (1H, m), 5.88, 5.93 (2H, s), 6.34–6.66 (4H, m), 7.10–7.51 (14H, m), 8.02–8.18 (1H, m)

ESI-MS: 511 [M+H]

Example 26-16)

[(2RS,3RS)-2-(3,4-Methylenedioxyphenyl)-3-hydroxyheptanoyl]-L-Trp(CH$_2$CO$_2$Et)-OH NMR (CDCl$_3$, δ): 0.78 (1.5H, t, J=7 Hz), 0.81 (1.5H, t, J=7 Hz), 1.07–1.47 (11H, m), 3.19–3.42 (3H, m), 3.90–4.09 (1H, m), 4.12 (1H, q, J=7 Hz), 4.20 (1H, q, J=7 Hz), 4.68 (1H, s), 4.76 (1H, s), 4.77–4.91 (1H, m), 5.88–5.97 (2H, m), 6.40–6.85 (5H, m), 7.00–7.22 (3H, m), 7.40 (0.5H, d, J=7 Hz), 7.52 (0.5H, d, J=7 Hz)

ESI-MS (m/z): 539 [M+H]

Example 26-17)

[(2R,3R)-2-(3,4-Methylenedioxyphenyl)-3-hydroxyheptanoyl]-L-Trp(CH$_2$CONMe$_2$)-OH NMR (CDCl$_3$, δ): 0.79 (3H, t, J=6 Hz), 1.08–1.63 (6H, m), 2.93 (3H, s), 2.98 (3H, s), 3.22–3.37 (3H, m), 3.86–3.92 (1H, m), 4.48–4.72 (2H, m), 4.77–4.83 (1H, m), 5.87 (2H, s), 6.47–6.57 (2H, m), 6.68 (1H, s), 6.93 (1H, s), 7.06–7.22 (4H, m), 7.55 (1H, d, J=7 Hz)

ESI-MS (m/z): 538 [M+H]

Example 26-18)

N$^α$-[3-Hydroxy-3,3-di(2-pyridyl)-2-(3,4-methylenedioxyphenyl)propionyl]-L-tryptophan NMR (CDCl$_3$, δ): 3.13–3.20 (2H, m), 4.58–4.75 (1H, m), 5.26, 5.47 (total 1H, s), 5.77–5.87 (2H, m), 6.29–6.72 (4H, m), 6.84–7.69 (10H, m), 8.12–8.39 (4H, m)

ESI-MS: 551 [M+H]

Example 26-19)

N$^α$-[(2RS,3RS)-2-(3,4-Methylenedioxyphenyl)-3-cyclopropyl-3-hydroxypropionyl]-L-tryptophan NMR (CDCl$_3$, δ): −0.10–0.40 (4H, m), 0.52–0.78 (1H, m), 3.10–3.50 (5H, m), 4.70–4.93 (1H, m), 5.83–5.94 (1H, m), 6.50–6.72 (4H, m), 6.87–7.50 (4H, m), 8.26 (0.5H, s), 8.35 (0.5H, s)

ESI-MS (m/z) 437 [M+H]

Example 26-20)

N$^α$-[(2RS,3SR)-3-Hydroxy-3-(2-biphenylyl)-2-(3,4-methylenedioxyphenyl)propionyl]-L-tryptophan NMR (CDCl$_3$, δ): 3.16–3.26 (2H, m), 3.45–3.53 (2H, m), 4.78–4.86 (1H, m), 5.24 (0.5H, d, J=8 Hz), 5.32 (0.5H, d, J=9 Hz), 5.82 (1H, d, J=7 Hz), 5.88 (1H, d, J=5 Hz), 5.97–6.11 (3H, m), 6.36–6.44 (0.5H, m), 6.66 (0.5H, dd, J=3, 13 Hz), 6.94–7.47 (14H, m), 7.96–8.07 (1H, m)

ESI-MS: 549 [M+H]

Example 26-21)

[(2R,3R)-2-(3,4-Methylenedioxyphenyl)-3-hydroxyoctanoyl]-L-Trp-OH (118 mg)

NMR (CDCl$_3$, δ): 0.82 (3H, t, J=7 Hz), 1.01–1.52 (8H, m), 3.10–3.38 (3H, m), 3.94–4.10 (1H, m), 4.73–4.88 (1H, m), 5.87 (2H, d, J=5 Hz), 6.32 (1H, d, J=9 Hz), 6.48 (1H, d, J=7 Hz), 6.58 (1H, d, J=8 Hz), 6.74 (1H, d, J=3 Hz), 7.08 (1H, t, J=7 Hz), 7.18 (1H, t, J=7 Hz), 7.29 (1H, d, J=7 Hz), 7.48 (1H, d, J=7 Hz), 8.26 (1H, s)

ESI-MS: 467 [M+H]

Example 26-22)

N$^α$-[3-(1-tert-Butoxycarbonyl-2-n-butylimidazol-4-yl)-2-(3,4-methylenedioxyphenyl)propionyl]-L-tryptophan Rf: 0.13 (benzene:ethyl acetate:acetic acid=20:20:1)
ESI-MS: 603 (M+H)

Example 26-23)

[3-(1-t-Butoxycarbonyl-2-pentylimidazol-4-yl)-2-(3,4-methylenedioxyphenyl)propionyl]-L-Trp(CH$_2$CO$_2^t$Bu)-OH
p NMR (CDCl$_3$, δ): 0.83–0.90 (3H, m), 1.16–1.34 (4H, m), 1.37 (4.5H, s), 1.40 (4.5H, s), 1.47–1.63 (11H, m), 2.78–3.02 (2H, m), 3.05–3.38 (3H, m), 3.82–3.98 (1H, m), 4.40–4.50 (2H, m), 4.68–4.87 (1H, m), 5.85–5.98 (2H, m), 6.37–7.60 (10H, m)
ESI-MS (m/z): 731 [M+H]

Example 26-24)

N-[(2S)-3-(1-tert-Butoxycarbonyl-2-n-butylimidazol-4-yl)-2-(3,4-methylenedioxyphenyl)propionyl]-L-3-(1-naphthyl)alanine
NMR (CDCl$_3$, δ): 0.79 (3H, t, J=8 Hz), 1.09–1.19 (2H, m), 1.33–1.46 (2H, m), 1.55 (9H, s), 2.70–2.92 (3H, m), 3.06–3.13 (1H, m), 3.34–3.42 (1H, m), 3.62–3.71 (1H, m), 4.01–4.08 (1H, m), 4.77–4.85 (1H, m), 5.90 (2H, d, J=2 Hz), 6.58–6.63 (2H, m), 6.70 (1H, s), 6.90 (1H, s), 7.19–7.23 (2H, m), 7.40–7.50 (2H, m), 7.66–7.80 (3H, m), 8.33 (1H, d, J=8 Hz)
ESI-MS: 614 [M+H]

Example 26-25)

A mixture of [3-(1-tert-butoxycarbonyl-2-n-butylimidazol-4-yl)-2-(3,4-methylenedioxyphenyl) propionyl]-L-Trp(CH$_2$CO$_2$Et)-OBzl (300 mg) and 10% palladium on activated carbon (300 mg) in ethanol (20 ml) and water (2 ml) was shaken under hydrogen atmosphere (3 atmospheric pressure) at ambient temperature for 1 hour. The mixture was filtered through a bed of celite and the filtrate was evaporated in vacuo. The residue was diluted with ethyl acetate and the solution was dried over magnesium sulfate. Filtering and removal of the solvents afforded a crude product. The crude diastereomers were separated by preparative TLC (benzene:ethyl acetate:acetic acid=20:20:1) to give [(2S)-3-(1-tert-butoxycarbonyl-2-n-butylimidazol-4-yl)-2-(3,4-methylenedioxyphenyl) propionyl]-L-Trp(CH$_2$CO$_2$Et)-OH (70 mg) as a slightly yellow powder.
NMR (CDCl$_3$, δ): 0.87 (3H, t, J=7 Hz), 1.22 (3H, t, J=8 Hz), 1.23–1.32 (2H, m), 1.58–1.67 (2H, m), 1.57 (9H, s), 2.82–2.93 (3H, m), 3.02–3.18 (2H, m), 3.27–3.35 (1H, m), 3.90 (1H, t, J=8 Hz), 4.14 (2H, q, J=8 Hz), 4.68 (2H, s), 4.69–4.77 (1H, m), 5.90 (2H, d, J=2 Hz), 6.63 (2H, s), 6.77 (1H, s), 6.81 (1H, s), 6.84 (1H, s), 6.99–7.16 (4H, m), 7.58 (1H, d, J=8 Hz)
ESI-MS: 689 [M+H]

The following compounds were obtained in substantially the same manner as that of Example 26-25).

Example 26-26

[(2S)-3-(1-tert-Butoxycarbonyl-2-n-butylimidazol- 4-yl)-2-(3,4-methylenedioxyphenyl)propionyl]-L-Trp (CH$_2$CH$_2$CO$_2$Et)-OH as a white solid
NMR (CDCl$_3$, δ): 0.86 (3H, t, J=8 Hz), 1.19 (3H, t, J=8 Hz), 1.21–1.30 (2H, m), 1.45–1.56 (2H, m), 1.54 (9H, s), 2.63–2.71 (2H, m), 2.80–2.93 (3H, m), 3.06–3.16 (2H, m), 3.23–3.32 (1H, m), 3.90–3.97 (1H, m), 4.08 (2H, q, J=8 Hz), 4.24–4.29 (2H, m), 4.67–4.75 (1H, m), 5.89–5.95 (2H, m), 6.62 (2H, s), 6.79 (1H, s), 6.83–6.87 (2H, m), 6.97–7.25 (4H, m), 7.57 (1H, d, J=8 Hz)
ESI-MS: 703 [M+H]

Example 26-27

[(2S)-3-(1-tert-Butoxycarbonyl-2-n-butylimidazol-4-yl)-2-(3,4-methylenedioxyphenyl)propionyl]-L-Trp(Me)-OH
NMR (CDCl$_3$, δ): 0.84 (3H, t, J=8 Hz), 1.20–1.31 (2H, m), 1.42–1.55 (2H, m), 1.56 (9H, s), 2.80–2.92 (3H, m), 3.00–3.18 (2H, m), 3.26–3.34 (1H, m), 3.60 (3H, s), 3.95–4.02 (1H, m), 4.68–4.74 (1H, m), 5.99, 6.01 (total 2H, s), 6.63 (2H, s), 6.73 (1H, s), 6.77 (1H, s), 6.87 (1H, s), 6.98 (1H, t, J=8 Hz), 7.09–7.26 (3H, m), 7.55 (1H, d, J=8 Hz)
ESI-MS: 617 [M+H]

Example 26-28)

[(2RS)-3-(1-tert-Butoxycarbonyl-2-n-butylimidazol-4-yl)-2-(3,4-methylenedioxyphenyl)propionyl]-L-Trp (CH$_2$CO$_2^t$Bu)-OH (2R:2S=1:4)
Rf: 0.28 (10% methanol in chloroform)
ESI-MS: 575 [M+H]

Example 26-29)

[(2S)-3-(1-tert-Butoxycarbonyl-2-n-butylimidazol-4-yl)-2-(3,4-methylenedioxyphenyl)propionyl]-L-Trp(Et)-OH
NMR (CDCl$_3$, δ): 0.84 (3H, t, J=8 Hz), 1.19–1.29 (2H, m), 1.35 (3H, t, J=8 Hz), 1.44–1.55 (2H, m), 1.56 (9H, s), 2.76–2.93 (3H, m), 3.03–3.17 (2H, m), 3.26–3.34 (1H, m), 3.95–4.06 (3H, m), 4.68–4.76 (1H, m), 5.89–6.03 (2H, m), 6.62 (2H, s), 6.77 (1H, s), 6.82 (1H, s), 6.86 (1H, s), 7.00 (1H, t, J=8 Hz), 7.13 (1H, t, J=8 Hz), 7.20–7.27 (2H, m), 7.57 (1H, d, J=8 Hz)
ESI-MS: 631 [M+H]

Example 26-30

N$^\alpha$-[3-(1H-Imidazol-4-yl)-2-(3,4-methylenedioxyphenyl)propionyl]-L-tryptophan Hydrochloride
NMR (DMSO-d$_6$, δ): 2.83–3.13 (4H, m), 3.88–3.97 (1H, m), 4.37–4.46 (1H, m), 5.98 (2H, s), 6.70–7.45 (11H, m), 8.37 (1H, d, J=8 Hz), 8.58–8.65 (1H, m)
ESI-MS: 447 [M+H]

Example 26-31)

N$^\alpha$-[3-(1-Methylimidazol-5-yl)-2-(3,4-methylenedioxyphenyl)propionyl]-L-tryptophan
NMR (DMSO-d$_6$, δ): 2.72–2.98 (4H, m), 3.09–3.18 (1H, m), 3.43, 3.47 (total 3H, s), 3.80–3.90 (1H, br), 4.30–4.39 (1H, br), 5.94, 5.96 (total 2H, s), 6.47–6.50 (1H, br s), 6.74–7.05 (6H, m), 7.28–7.53 (3H, m), 7.93–8.00 (1H, br)
ESI-MS: 461 [M+H]

Example 26-32

[3-(1-t-Butoxycarbonyl-2-ethylimidazol-4-yl)-2-(3,4-methylenedioxyphenyl)propionyl]-L-tryptophan
NMR (DMSO-d$_6$, δ): 1.11–1.19 (3H, m), 1.45 (4.5H, s), 1.52 (4.5H, s), 2.62–2.73 (1H, m), 2.80–2.89 (2H, m), 2.94–3.10 (3H, m), 3.90–3.97 (1H, m), 4.37–4.46 (1H, m), 5.95 (2H, s), 6.70–6.78 (2H, m), 6.82–7.07 (5H, m), 7.32 (1H, d, J=7 Hz), 7.47 (1H, d, J=6 Hz), 8.21–8.29 (1H, m)
ESI-MS (m/z): 575 [M+H]

Example 26-33)

N$^\alpha$-[(2RS)-3-(1-tert-Butoxycarbonyl-2-n-propylimidazol-4-yl)-2-(3,4-methylenedioxyphenyl)propionyl]-L-tryptophan (2R:2S=1:4)

Rf: 0.10 (10% methanol in chloroform)

ESI-MS 589 [M+H]

The following compounds were obtained in substantially the same manner as that of Example 28-3).

Example 27-1)

N(-[3-(2-n-Butylimidazol-4-yl)-2-(3,4-methylenedioxyphenyl)propionyl]-L-tryptophan Ethyl Ester Hydrochloride NMR (DMSO-$d_6$, δ): 0.81–0.90 (3H, m), 0.95–1.11 (3H, m), 1.16–1.27 (2H, m), 1.56–1.68 (2H, m), 2.77–2.90 (3H, m), 2.98–3.18 (4H, m), 3.86–3.98 (3H, m), 4.36–4.49 (1H, m), 5.98 (2H, s), 6.73 (1H, t, J=8 Hz), 6.80 (1H, t, J=8 Hz), 6.86–7.12 (5H, m), 7.29–7.45 (2H, m), 8.52–8.59 (1H, m)

ESI-MS: 531 [M+H]

Example 27-2)

N-[(2S)-3-(2-n-Butylimidazol-4-yl)-2-(3,4-methylenedioxyphenyl)propionyl]-L-3-(1-naphthyl)alanine trifluoroacetic Acid Salt NMR (DMSO-$d_6$, δ): 0.83 (3H, t, J=8 Hz), 1.13–1.23 (2H, m), 1.51–1.61 (2H, m), 2.77 (2H, t, J=8 Hz), 2.78–2.87 (1H, m), 2.99–3.10 (1H, m), 3.17–3.25 (1H, m), 3.50–3.80 (3H, m), 4.45–4.53 (1H, m), 6.00 (2H, s), 6.72 (1H, d, J=8 Hz), 6.82 (1H, d, J=8 Hz), 6.86 (1H, s), 7.01 (1H, s), 7.19 (1H, d, J=8 Hz), 7.32 (1H, t, J=8 Hz), 7.50–7.60 (2H, m), 7.79 (1H, d, J=8 Hz), 7.92 (1H, d, J=8 Hz), 8.08 (1H, d, J=8 Hz), 8.52 (1H, d, J=8 Hz)

ESI-MS: 514 [M+H]

Example 27-3)

[(2S)-3-(2-n-Butylimidazol-4-yl)-2-(3,4-methylenedioxyphenyl)propionyl]-L-Trp(Me)-OH trifluoroacetic Acid Salt NMR (DMSO-$d_6$, δ): 0.83 (3H, t, J=8 Hz), 1.13–1.25 (2H, m), 1.53–1.63 (2H, m), 2.77 (2H, t, J=8 Hz), 2.86–3.18 (4H, m), 3.67 (3H, m), 3.75–3.88 (2H, m), 4.41 (1H, dd, J=8, 14 Hz), 5.98 (2H, s), 6.74 (1H, d, J=8 Hz), 6.83 (1H, d, J=8 Hz), 6.89 (2H, d, J=5 Hz), 7.00 (1H, t, J=8 Hz), 7.08–7.16 (2H, m), 7.36 (1H, d, J=8 Hz), 7.48 (1H, d, J=8 Hz), 8.37 (1H, d, J=8 Hz)

ESI-MS: 517 [M+H]

Example 27-4)

[(2RS)-3-(2-n-Butylimidazol-4-yl)-2-(3,4-methylenedioxyphenyl)propionyl]-L-Trp(CH$_2$CO$_2$Me)-OMe hydrochloride (2R:2S=1:4)

NMR (DMSO-$d_6$, δ): 0.80–0.89 (3H, m), 1.17–1.25 (2H, m), 1.58–1.67 (2H, m), 2.76–3.15 (7H, m), 3.49 (3H, s), 3.64 (3H, s), 3.85–3.93 (1H, m), 4.39–4.48 (1H, m), 5.03–5.06 (2H, br s), 5.96–5.99 (2H, br s), 6.70–6.88 (3H, m), 6.98–7.14 (4H, m), 7.29–7.36 (1H, m), 7.43–7.48 (1H, m), 8.53–8.58 (1H, m)

ESI-MS: 589 [M+H]

Example 27-5)

N$^α$-[(2S)-3-(2-n-Butylimidazol-4-yl)-2-(3,4-methylenedioxyphenyl)propionyl]-L-Trp(Et)-OH trifluoroacetic Acid Salt NMR (DMSO-$d_6$, δ): 0.82 (3H, t, J=8 Hz), 1.12–1.23 (2H, m), 1.28 (3H, t, J=8 Hz), 1.52–1.62 (2H, m), 2.77 (2H, t, J=8 Hz), 2.85–3.15 (4H, m), 3.80–3.88 (1H, m), 4.05–4.13 (2H, m), 4.36–4.45 (1H, m), 5.98 (2H, s), 6.73 (1H, d, J=8 Hz), 6.82 (1H, d, J=8 Hz), 6.90 (1H, s), 6.96–7.02 (2H, m), 7.08–7.15 (2H, m), 7.39 (1H, d, J=8 Hz), 7.48 (1H, d, J=8 Hz), 8.37 (1H, d, J=8 Hz)

ESI-MS: 531 [M+H]

Example 27-6)

A mixture of N$^α$-[3-(1-triphenylmethylimidazol-4-yl)-2-(3,4-methylenedioxyphenyl)propionyl]-L-tryptophan benzyl ester (290 mg) in 80% acetic acid-water (5 ml) was stirred at 50° C. for 5 hours. The resulting mixture was cooled to ambient temperature and the solution was diluted with water. Carbinol was removed by filtration and the filtrate was neutralized with saturated sodium hydroxide aqueous solution, and then the aqueous layer was extracted with ethyl acetate. Drying, filtering and removal of the solvents afforded N$^α$-[3-(imidazol-4-yl)-2-(3,4-methylenedioxyphenyl)propionyl]-L-tryptophan benzyl ester (180 mg) as a yellow powder.

NMR (CDCl$_3$, δ): 2.77–2.88 (1H, m), 3.18–3.32 (2H, m), 3.86–3.97 (1H, m), 4.75–4.86 (1H, m), 4.98–5.06 (2H, m), 5.83–5.89 (2H, m), 6.57–6.77 (5H, m), 6.98 (1H, t, J=8 Hz), 7.08–7.40 (10H, m), 7.88–7.95 (1H, m), 8.67–8.70 (1H, br)

ESI-MS: 537 [M+H]

Example 27-7)

N$^α$-[(2S)-3-(2-Ethylimidazol-4-yl)-2-(3,4-methylenedioxyphenyl)propionyl]-L-tryptophan trifluoroacetic acid salt was obtained according to a similar manner to that of Example 28-3).

NMR (DMSO-$d_6$, δ): 1.18 (3H, t, J=6 Hz), 2.68–3.17 (6H, m), 3.82–3.88 (1H, m), 4.41–4.49 (1H, m), 5.98 (2H, s), 6.73–7.08 (8H, m), 7.32 (1H, d, J=7 Hz), 7.44 (1H, d, J=7 Hz), 8.35 (1H, d, J=7 Hz)

ESI-MS (m/z): 475 [M+H]

Example 27-8)

N-[(2S)-3-(2-n-Propylimidazol-4-yl)-2-(3,4-methylenedioxyphenyl)propionyl]-L-tryptophan trifluoroacetic acid salt was obtained according to a similar manner to that of Preparation 36-21).

NMR (DMSO-$d_6$, δ): 0.79 (3H, t, J=8 Hz), 1.63 (2H, q, J=8 Hz), 2.76 (2H, t, J=8 Hz), 2.82–3.25 (6H, m), 3.85 (1H, t, J=8 Hz), 4.45 (1H, dd, J=7, 15 Hz), 5.98 (2H, s), 6.75 (1H, d, J=9 Hz), 6.82 (1H, d, J=9 Hz), 6.89 (1H, s), 6.93–6.99 (2H, m), 7.02–7.08 (2H, m), 7.33 (1H, d, J=8 Hz), 7.47 (1H, d, J=8 Hz), 8.39 (1H, d, J=8 Hz)

ESI-MS: 489.1 [M+H]

Example 27-9)

N$^α$-[(2S)-3-(2-Pentylimidazol-4-yl)-2-(3,4-methylenedioxyphenyl)propionyl]-L-tryptophan trifluoroacetic acid salt was obtained according to a similar manner to that of Example 28-3).

NMR (DMSO-$d_6$, δ): 0.81 (3H, t, J=7 Hz), 1.07–1.30 (4H, m), 1.52–1.66 (2H, m), 2.70–3.13 (6H, m), 3.83–3.88 (1H, m), 4.40–4.50 (1H, m), 5.97 (2H, s), 6.72–7.07 (8H, m), 7.33 (1H, d, J=8 Hz), 7.47 (1H, d, J=7 Hz), 8.38 (1H, d, J=7 Hz)

ESI-MS (m/z): 517 [M+H]

Example 27-10)

N$^α$-[(2S)-3-(2-n-Butylimidazol-4-yl)-2-(3,4-methylenedioxyphenyl)propionyl]-L-tryptophan hydrochloride was obtained according to a similar manner to that of Example 28-1) from N<sup>α</sup>-[(2S)-3-(1-tert-butoxycarbonyl-2-n-butylimidazol-4-yl)-2-(3,4-methylenedioxyphenyl)propionyl]-L-tryptophan ethyl ester.

NMR (DMSO-$d_6$, δ): 0.83 (3H, t, J=8 Hz), 1.16–1.24 (2H, m), 1.56–1.67 (2H, m), 2.78 (2H, t, J=8 Hz), 2.82–2.99 (2H, m), 3.06–3.15 (2H, m), 3.30–3.40 (1H, m),3.93 (1H, dd, J=8, 10 Hz), 4.45 (1H, dd, J=8, 14 Hz), 5.98 (2H, s), 6.76 (1H, d, J=8 Hz), 6.81 (1H, d, J=8 Hz), 6.90 (1H, s), 6.95–7.08 (4H, m), 7.34 (1H, d, J=8 Hz), 7.47 (1H, d, J=8 Hz), 8.43 (1H, d, J=8 Hz)

ESI-MS: 503 [M+H]

Example 28-1)

A mixture of [(2S)-3-(1-tert-butoxycarbonyl-2-n-butylimidazol-4-yl)-2-(3,4-methylenedioxyphenyl)propionyl]-L-Trp($CH_2CO_2Et$)-OH (60 mg) in ethanol (4 ml) and 1N sodium hydroxide aqueous solution (2 ml) was stirred at ambient temperature for 1 hour. The reaction was quenched with 1N hydrochloric acid (2 ml), and then the resulting mixture was diluted with ethyl acetate followed by washing with water. Drying, filtering and removal of the solvents afforded [(2S)-3-(2-n-butylimidazol-4-yl)-2-(3,4-methylenedioxyphenyl)propionyl]-L-Trp($CH_2CO_2H$)-OH (40 mg) as a slightly yellow powder.

NMR (DMSO-$d_6$, δ): 0.83 (3H, t, J=8 Hz), 1.13–1.25 (2H, m), 1.50–1.63 (2H, m), 2.73 (2H, t, J=8 Hz), 2.80–3.17 (5H, m), 3.87 (1H, t, J=8 Hz), 4.38–4.48 (1H, m), 4.87 (2H, s), 5.97 (2H, s), 6.73 (1H, d, J=8 Hz), 6.81 (1H, d, J=8 Hz), 6.86–6.92 (2H, m), 6.97–7.13 (3H, m), 7.32 (1H, d, J=8 Hz), 7.49 (1H, d, J=8 Hz), 8.36 (1H, d, J=8 Hz)

ESI-MS: 561 [M+H]

The following compound was obtained in substantially the same manner as that of Example 28-1).

Example 28-2)

[(2S)-3-(2-n-Butylimidazol-4-yl)-2-(3,4-methylenedioxyphenyl)propionyl]-L-Trp($CH_2CH_2CO_2H$)-OH NMR (DMSO-$d_6$, δ): 0.80–0.88 (3H, m), 1.10–1.25 (2H, m), 1.56–1.65 (2H, m), 2.66–3.12 (8H, m), 3.84–3.92 (1H, m), 4.26–4.43 (3H, m), 5.97 (2H, s), 6.71–7.02 (6H, m), 7.08–7.15 (1H, m), 7.38–7.49 (2H, m), 8.30–8.36 (1H, m)

ESI-MS: 575 [M+H]

Example 28-3)

A solution of [(2RS)-3-(1-tert-butoxycarbonyl-2-n-butylimidazol-4-yl)-2-(3,4-methylenedioxyphenyl)propionyl]-L-Trp($CH_2CO_2^tBu$)-OMe (190 mg) in trifluoroacetic acid (5 ml) was stirred at ambient temperature for 30 minutes. Trifluoroacetic acid was evaporated in vacuo and the residue was triturated with ether-n-hexane (1:3) to give [(2RS)-3-(2-n-butylimidazol-4-yl)-2-(3,4-methylenedioxyphenyl)propionyl]-L-Trp($CH_2CO_2H$)-OMe trifluoroacetic acid salt (2R:2S=1:4) (173 mg) as a slightly yellow powder.

NMR (DMSO-$d_6$, δ): 0.80–0.89 (3H, m), 1.17–1.30 (2H, m), 1.57–1.67 (2H, m), 2.75–3.18 (9H, m), 3.48, 3.55 (total 3H, s), 3.79–3.86 (1H, m), 4.40–4.48 (1H, m), 4.80, 4.90 (total 2H, s), 5.98 (2H, s), 6.70–6.86 (3H, m), 6.95–7.13 (3H, m), 7.28–7.38 (1H, m), 7.45 (1H, d, J=8 Hz), 8.52–8.58 (1H, m)

ESI-MS: 575 [M+H]

Example 28-4)

A solution of [(2RS)-3-(1-t-butoxycarbonyl-2-pentylimidazol-4-yl)-2-(3,4-methylenedioxyphenyl)propionyl]-L-Trp($CH_2CO_2^tBu$)-OH (160 mg) in trifluoroacetic acid (20 ml) was stirred at ambient temperature for 30 minutes. The solution was concentrated in vacuo and the diastereomers were separated by preparative thin-layer chromatography (chloroform:methanol:acetic acid=8:1:1) to give [(2S)-3-(2-pentylimidazol-4-yl)-2-(3,4-methylenedioxyphenyl)propionyl]-L-Trp($CH_2CO_2H$)-OH acetic acid salt (70 mg) as an amorphous powder.

NMR (DMSO-$d_6$, δ): 0.87–0.90 (3H, m), 1.13–1.35 (4H, m), 1.43–1.70 (2H, m), 2.60–2.78 (2H, m), 2.95–3.22 (5H, m), 3.35–3.45 (1H, m), 4.05–4.18 (2H, m), 4.52–4.68 (1H, m), 5.93 (2H, s), 6.30–6.45 (1H, m), 6.65–6.75 (3H, m), 6.85–6.95 (3H, m), 7.02–7.10 (1H, m), 7.20–7.30 (1H, m), 7.35–7.44 (1H, m)

ESI-MS (m/z): 575 [M+H]

The following compounds were obtained in substantially the same manner as that of Example 14-1).

Example 29-1)

[(2RS,3RS)-2-(3,4-Methylenedioxyphenyl)-3-hydroxyheptanoyl]-L-Trp($CH_2CO_2H$)-OH from [(2RS,3RS)-2-(3,4-methylenedioxyphenyl)-3-hydroxyheptanoyl]-L-Trp($CH_2CO_2Et$)-OBzl Rf: 0.30, 0.40 (chloroform:methanol:acetic acid=8:1:1)

ESI-MS (m/z): 509 [M-H]

Example 29-2)

[(2R,3R)-2-(3,4-Methylenedioxyphenyl)-3-hydroxyheptanoyl]-L-Trp($CH_2CO_2H$)-OH from [(2R,3R)-2-(3,4-methylenedioxyphenyl)-3-hydroxyheptanoyl]-L-Trp($CH_2CO_2Me$)-OMe NMR (DMSO-$d_6$, δ): 0.78 (3H, t, J=7 Hz), 1.00–1.40 (6H, m), 2.95–3.20 (3H, m), 3.42 (1H, d, J=8 Hz), 3.88–3.98 (1H, m), 4.48–4.56 (1H, m), 4.92 (2H, s), 5.96 (1H, s), 5.97 (1H, s), 6.72–6.83 (2H, m), 6.90 (1H, s), 7.00–7.15 (2H, m), 7.18 (1H, s), 7.31 (1H, d, J=7 Hz), 7.56 (1H, d, J=7 Hz), 8.23 (1H, d, J=7 Hz)

ESI-MS (m/z): 511 [M+H]

Example 29-3)

[(2R,3R)-3-Hydroxy-2-(3,4-methylenedioxyphenyl)-heptanoyl]-L-Trp($CH_2CH_2CO_2H$)-OH from [(2R,3R)-3-hydroxy-2-(3,4-methylenedioxyphenyl)heptanoyl]-L-Trp($CH_2CH_2CO_2Et$)-OMe NMR (DMSO-$d_6$, δ): 0.78 (3H, t, J=7 Hz), 1.05–1.34 (6H, m), 2.67–2.74 (2H, m), 2.98–3.16 (2H, m), 3.39–3.46 (2H, m), 3.88–3.96 (1H, br), 4.32 (2H, t, J=8 Hz), 4.49 (1H, dd, J=7, 14 Hz), 5.96 (2H, s), 6.74 (1H, d, J=7 Hz), 6.80 (1H, d, J=7 Hz), 6.88 (1H, s), 7.00 (1H, t, J=8 Hz), 7.12 (1H, t, J=8 Hz), 7.19 (1H, s), 7.42 (1H, d, J=8 Hz), 7.52 (1H, d, J=8 Hz), 8.17 (1H, d, J=8 Hz)

ESI-MS: 525 [M+H]

Example 29-4)

[(2R,3R)-2-(3,4-Methylenedioxyphenyl)-3-hydroxyoctanoyl]-L-Trp($CH_2COOH$)-OH (55 mg), as a less polar isomer from [(2RS,3RS)-2-(3,4-methylenedioxyphenyl)-3-hydroxyoctanoyl]-L-Trp($CH_2COOEt$)-OBzl by using preparative thin layer chromatography ($CHCl_3$:MeOH:AcOH=16:1:1) mp: 116–118° C.

Rf: 0.40 ($CHCl_3$:MeOH:AcOH=8:1:1)

NMR (DMSO-$d_6$ δ): 0.80 (3H, t, J=7 Hz), 1.01–1.45 (8H, m), 2.98 (2H, m), 3.23–3.38 (1H, m), 3.88–3.98 (1H, m), 4.45–4.57 (1H, m), 4.90 (2H, s), 5.92–6.02 (2H, m), 6.75 (1H, d, J=8 Hz), 6.82 (1H, d, J=8 Hz), 7.02 (1H, t, J=8 Hz), 7.12 (1H, t, J=8 Hz), 7.18 (1H, s), 7.32 (1H, d, J=8 Hz), 7.57 (1H, d, J=8 Hz), 8.23 (1H, d, J=8 Hz)

ESI-MS: 525 [M+H]

Example 29-5)

[(2RS)-3-(1-tert-Butoxycarbonyl-2-n-butylimidazol-4-yl)-2-(3,4-methylenedioxyphenyl)propionyl]-L-Trp($CH_2CO_2H$)-OH (2R:2S=1:4) was obtained as a white powder according to a similar manner to that of Example 26-25) from [(2RS)-3-(1-tert-butoxycarbonyl-2-n-butylimidazol-4-yl)-2-(3,4-methylenedioxyphenyl)propionyl]-L-Trp($CH_2CO_2Bzl$)-OBzl.

NMR (CDCl$_3$, δ): 0.86–0.93 (3H, m), 1.22–1.33 (4H, m), 1.52, 1.57 (total 9H, s), 2.80–3.05 (3H, m), 3.55–3.80 (2H, m), 4.60–4.72 (3H, m), 5.80–5.85 (2H, br s), 6.44–6.52 (3H, m), 6.68–6.76 (3H, m), 6.88–7.22 (4H, m), 7.50–7.56 (1H, m)

ESI-MS: 661 [M+H]

Example 30-1)

To a solution of N$^\alpha$-[(2R,3R)-2-(3,4-methylenedioxyphenyl)-3-hydroxyheptanoyl]-L-tryptophan (300 mg) in N,N-dimethylformamide (10 ml) were added potassium carbonate (69 mg) and ethyl iodide (155 mg) and the mixture was stirred at ambient temperature for 3 hours. The mixture was diluted with ethyl acetate (20 ml) and the solution was washed with 0.5N hydrochloric acid (20 ml×2), saturated sodium bicarbonate aqueous solution (20 ml×2) and brine (20 ml) successively and the organic layer was dried over magnesium sulfate. The solution was concentrated in vacuo and the residue was purified by silica gel column chromatography (hexane:ethyl acetate=2:1) to give N [(2R,3R)-2-(3,4-methylenedioxyphenyl)-3-hydroxyheptanoyl]-L-tryptophan ethyl ester as an amorphous powder (260 mg).

NMR (CDCl$_3$, δ): 0.82 (3H, t, J=7 Hz), 1.18 (3H, t, J=7 Hz), 1.20–1.53 (6H, m), 3.13–3.36 (3H, m), 3.97–4.16 (4H, m), 4.78–4.88 (1H, m), 5.90 (2H, s), 6.10 (1H, d, J=8 Hz), 6.53 (1H, d, J=8 Hz), 6.58–6.68 (2H, m), 6.87–6.93 (1H, m), 7.10 (1H, t, J=7 Hz), 7.18 (1H, t, J=7 Hz), 7.32 (1H, d, J=8 Hz), 7.48 (1H, d, J=8 Hz), 8.10 (1H, s)

ESI-MS (m/z): 481 [M+H]

Example 30-2)

To a solution of [(2RS)-3-(1-tert-butoxycarbonyl-2-n-butylimidazol-4-yl)-2-(3,4-methylenedioxyphenyl)propionyl-L-Trp($CH_2CO_2{}^tBu$)-OH (190 mg) in benzene (7 ml) and methanol (2 ml) was added dropwise trimethylsilyldiazomethane (0.2 ml, 2.0M n-hexane solution) and the mixture was stirred at ambient temperature for 2 hours. The mixture was evaporated in vacuo to give [(2RS)-3-(1-tert-butoxycarbonyl-2-n-butylimidazol-4-yl)-2-(3,4-methylenedioxyphenyl)propionyl]-L-Trp($CH_2CO_2{}^tBu$)-OMe (2R:2S=1:4) (200 mg) as a slightly yellow amorphous powder.

NMR (CDCl$_3$, δ): 0.86–0.96 (3H, m), 1.26–1.69 (6H, m), 1.46, 1.57 (total 9H, s), 1.52, 1.62 (total 9H, s), 2.80–2.96 (3H, m), 3.10–3.30 (3H, m), 3.56, 3.60 (total 3H, s), 3.76–3.83 (1H, m), 4.55, 4.66 (total 2H, s), 5.90 (2H, s), 6.18–6.30 (1H, m), 6.65–6.94 (4H, m), 7.04–7.19 (3H, m), 7.30, 7.44 (total 1H, d, J=8 Hz)

ESI-MS: 731 [M+H]

Example 31-1)

To a solution of [(2RS,3RS)-2-(3,4-methylenedioxyphenyl)-3-hydroxyheptanoyl]-L-Trp ($CH_2CO_2H$)-OH (1.15 g) in methanol (20 ml) was added dropwise trimethylsilyldiazomethane (2 ml, 2.0M n-hexane solution) and the mixture was stirred at ambient temperature for 30 minutes. The solution was concentrated in vacuo and the diastereomers were separated by silica gel column chromatography (hexane:ethyl acetate=2:1) to give [(2R, 3R)-2-(3,4-methylenedioxyphenyl)-3-hydroxyheptanoyl]-L-Trp($CH_2CO_2Me$)-OMe (313 mg) as an amorphous powder.

NMR (CDCl$_3$, δ): 0.82 (3H, t, J=7 Hz), 1.12–1.50 (6H, m), 3.20–3.35 (3H, m), 3.65 (3H, s), 3.75 (3H, s), 3.96–3.98 (1H, m), 4.00–4.10 (1H, m), 4.78 (2H, s), 4.81–4.89 (1H, m), 5.91 (1H, s), 5.92 (1H, s), 6.19 (1H, d, J=7 Hz), 6.55–6.68 (3H, m), 6.81 (1H, s), 7.09–7.26 (3H, m), 7.48 (1H, d, J=6 Hz)

ESI-MS (m/z): 539 [M+H]

Example 31-2)

[(2RS)-3-(1-tert-Butoxycarbonyl-2-n-butylimidazol-4-yl)-2-(3,4-methylenedioxyphenyl)propionyl]-L-Trp ($CH_2CO_2Me$)-OMe (2R:2S=1:4) was obtained as a white amorphous powder according to a similar manner to that of Example 31-1).

Rf: 0.72 (10% methanol in chloroform)

NMR (CDCl$_3$, δ): 0.88–0.97 (3H, m), 1.32–1.42 (2H, m), 1.53, 1.62 (total 9H, s), 1.58–1.69 (2H, m), 2.83–2.97 (3H, m), 3.10–3.30 (3H, m), 3.56, 3.60 (total 3H, s), 3.73 (3H, s), 3.76–3.82 (1H, m), 4.78 (2H, s), 4.79–4.86 (1H, m), 5.90 (2H, s), 6.18–6.27 (1H, m), 6.65–6.72 (3H, m), 6.89–6.93 (2H, m), 7.08–7.20 (3H, m), 7.47 (1H, d, J=8 Hz)

ESI-MS 689 [M+H]

Example 32

To a solution of N$^\alpha$-[(2RS,3RS)-2-(3,4-methylenedioxyphenyl)-3-hydroxyheptanoyl]-L-tryptophan benzyl ester (255 mg) in dichloromethane (5 ml) were added pyridine (74 mg), acetic anhydride (72 mg) and 4-(dimethylamino)pyridine (11 mg) at 5° C. and the mixture was stirred at ambient temperature for 18 hours. The mixture was diluted with ethyl acetate (20 ml) and the solution was washed with 0.5N hydrochloric acid (20 ml×2), saturated sodium bicarbonate aqueous solution (20 ml×2) and brine (20 ml) successively and the organic layer was dried over magnesium sulfate. The solution was filtered and concentrated in vacuo to give N$^\alpha$-[(2RS,3RS)-2-(3,4-methylenedioxyphenyl)-3-acetoxyheptanoyl]-L-tryptophan benzyl ester as an oil.

NMR (CDCl$_3$, δ): 0.73–0.85 (3H, m), 1.07–1.55 (6H, m), 1.92 (1.5H, s), 1.96 (1.5H, s), 3.12–3.30 (2H, m), 3.38–3.54 (1H, m), 4.92–5.03 (2H, m), 5.05–5.13 (1H, m), 5.43–5.52 (1H, m), 5.88–6.00 (2H, m), 6.10 (0.5H, d, J=8 Hz), 6.22 (0.5H, d, J=8 Hz), 6.43–6.88 (4H, m), 6.98–7.60 (9H, m), 7.92 (0.5H, 3), 8.00 (0.5H, s)

ESI-MS (m/z): 585 [M+H]

Example 33

To a solution of N-[(2RS,3RS)-2-(3,4-methylenedioxyphenyl)-3-hydroxyheptanoyl]-3-(benzo[b] thiophen-3-yl)-L-alanine methyl ester (280 mg) in dichloromethane (5 ml) was added m-chloroperbenzoic acid (250 mg) and the mixture was stirred at ambient temperature for 2 hours. After the mixture was concentrated in vacuo, the residue was added to 10% sodium thiosulfate aqueous solution (20 ml) and ethyl acetate (20 ml). The organic layer was washed with saturated sodium bicarbonate aqueous solution (20 ml×2) and brine (20 ml) successively and the organic layer was dried over magnesium sulfate. The solution was filtered and concentrated in vacuo to give N$^\alpha$-[(2RS,3RS)-2-(3,4-methylenedioxyphenyl)-3-hydroxyheptanoyl]-3-(benzo[b]thiophen-1,1-dioxide-3-yl)-L-alanine methyl ester as an amorphous powder (323 mg).

NMR (CDCl$_3$, δ): 0.80 (3H, t, J=7 Hz), 1.10–1.50 (6H, m), 2.95–3.21 (2H, m), 3.22–3.33 (1H, m), 3.40–3.53 (1H, m), 5.92–5.98 (2H, m), 6.10 (0.5H, s), 6.54 (0.5H, s), 6.32 (0.5H, d, J=7 Hz), 6.39 (0.5H, d, J=7 Hz), 6.66–6.80 (3H, m), 7.40–7.77 (4H, m)

ESI-MS (m/z): 516 [M+H]

Example 34

A solution of [(2RS,3RS)-2-(3,4-methylenedioxyphenyl)-3-hydroxyheptanoyl]-L-Trp(CH$_2$CO$_2$Et)-OH (72 mg) in ammonia solution (5 ml, 7.5N methanol solution) was stirred at ambient temperature for 72 hours. The solution was concentrated in vacuo to give [(2RS,3RS)-2-( 3,4-methylenedioxyphenyl)-3-hydroxyheptanoyl]-L-Trp (CH$_2$CONH$_2$)-OH (60 mg) as an amorphous powder.

NMR (DMSO-d$_6$, δ): 0.73–0.79 (3H, m), 1.02–1.40 (6H, m), 2.90–3.20 (3H, m), 3.32 (1H, d, J=8 Hz), 3.82–3.98 (1H, m), 4.12–4.22 (1H, m), 4.55 (1H, s), 4.65 (1H, s), 5.95 (1H, s), 5.96 (1H, s), 6.70–7.18 (12H, m)

ESI-MS (m/z): 510 [M+H]

Example 35

[(2RS,3RS)-2-(3,4-Methylenedioxyphenyl)-3-hydroxyheptanoyl]-L-Trp-NHSO$_2$CH$_3$ (190 mg) was separated by using preparative TLC (benzene:ethyl acetate:acetic acid=20:20:1) to give [(2R,3R)-2-(3,4-methylenedioxyphenyl)-3-hydroxyheptanoyl]-L-Trp-NHSO$_2$CH$_3$ (75 mg) as a less polar isomer, as an amorphous powder.

Rf: 0.57 (benzene:ethyl acetate:acetic acid=20:20:1)

NMR (CDCl$_3$, δ): 0.84 (3H, t, J=7 Hz), 1.11–1.42 (6H, m), 3.09 (3H, s), 3.13–3.38 (3H, m), 3.98–4.09 (1H, m), 4.63–4.72 (1H, m), 5.94 (2H, s), 6.32 (1H, d, J=8 Hz), 6.52–6.68 (3H, m), 6.90 (1H, d, J=4 Hz), 7.09 (1H, t, J=7 Hz), 7.20 (1H, t, J=7 Hz), 7.35 (1H, d, J=8 Hz), 7.43 (1H, d, J=8 Hz), 8.26 (1H, s)

ESI-MS: 530 [M+H]

Example 36

[(2R,3R)-2-(3,4-Methylenedioxyphenyl)-3-hydroxyoctanoyl]-L-Trp(CH$_2$COOH)-NHSO$_2$CH$_3$ (118 mg) was obtained according to a similar manner to that of Example 14-1) from [(2R,3R)-2-(3,4-methylenedioxyphenyl)-3-hydroxyoctanoyl]-L-Trp (CH$_2$COOEt)-NHSO$_2$CH$_3$ NMR (DMSO-d$_6$, δ): 0.80 (3H, t, J=7 Hz), 0.94–1.46 (8H, m), 3.00 (3H, s), 3.02–3.18 (2H, m), 3.37–3.48 (1H, m), 3.86–3.98 (1H, m), 4.50–4.70 (1H, m), 4.75–5.00 (3H, m), 5.96 (1H, s), 6.74 (1H, d, J=7 Hz), 6.80 (1H, d, J=7 Hz), 6.86 (1H, s), 6.96–7.40 (5H, m), 7.56–7.72 (1H, m), 8.27 (1H, d, J=7 Hz)

ESI-MS (m/z) 602 [M+H]

What is claimed is:
1. A compound represented by the formula:

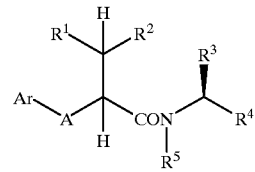

or a pharmaceutically acceptable salt thereof, wherein $R^1$ is lower alkyl, cyclo(lower)alkyl, optionallyy substituted aryl, cyclo(lower)alky(lower)alkyl, or ar(lower)alkyl, $R^2$ is hydroxy or protected hydroxy, $R^3$ is lower alkyl, aryl, ar(lower)alkyl, or optionally substituted heterocyclic-(lower)alkyl, $R^4$ is carboxy, protected carboxy or lower alkylsulfonylcarbamoyl, $R^5$ is hydrogen or lower alkyl, A is a single bond or lower alkylene, and Ar is optionally substituted aryl.

2. The compound of claim 1, wherein $R^1$ is lower alkyl, cyclo(lower)alkyl, or $C_6$–$C_{10}$ aryl optionally substituted by a group selected from the group consisting of hydroxy, protected hydroxy, halogen, lower alkoxy, carboxy, protected carboxy, lower alkylenedioxy, carbamoyl(lower)alkyl, N- or N,N-di(lower)alkylcarbaamoyl(lower)alkyl, carboxy (lower)alkyl, protected carboxy(lower)alkyl, $C_6$–$C_{10}$ ar(lower)alkyl, halo (lower) alkyl, halo (lower) alkoxy, lower alkanoyl, lower alkyl and $C_6$–$C_{10}$ aryl, $R^3$ is lower alkyl, $C_6$–$C_{10}$ aryl, $C_6$–$C_{10}$ ar(lower)alkyl or heterocyclic(lower)alkyl optionally substituted by a group selected from the group consisting of hydroxy, protected hydroxy, halogen, lower alkoxy, carboxy, protected carboxy, lower alkylenedioxy, carbamoyl (lower)alkyl, N- or N,N- di(lower)alkylcarbamoyl (lower)alkyl, carboxy(lower)alkyl, protected carboxy (lower)alkyl, $C_6$-$C_{10}$ ar(lower)alkyl, halo(lower)alkyl, halo (lower)alkoxy, lower alkanoyl and lower alkyl, said heterocyclic group being unsaturated condensed 7- to 12-membered heterocyclic group containing 1 to 5 nitrogen atom(s), unsaturated condensed 7- to 12-membered heterocyclic group containing 1 to 3 sulfur atom(s) or its S,S-dioxide, unsaturated 3- to 8-membered heteromonocyclic group containing 1 to 4 nitrogen atom(s), saturated 3- to 8-membered heteromonocyclic group containing 1 to 4 nitrogen atom(s), unsaturated condensed 7- to 12-membered heterocyclic group containing 1 to 2 oxygen atom(s) and 1 to 3 nitrogen atom(s), unsaturated 3- to 8-membered heteromonocyclic group containing 1 to 2 oxygen atom(s) and 1 to 3 nitrogen atom(s), saturated 3- to 8-membered heteromonocyclic group containing 1 to 2 oxygen atom(s) and 1 to 3 nitrogen atom(s), unsaturated condensed 7- to 1 2-membered heterocyclic group containing 1 to 2 sulfur atom(s)and 1 to 3 nitrogen atom(s), unsaturated 3- to 8-membered heteromonocyclic group containing 1 to 2 sulfur atom(s) and 1 to 3 nitrogen atom(s), saturated 3 to 8-membered heteromonocyclic group containing 1 to 2 sulfur atom(s) and 1 to 3 nitrogen atom(s), or unsaturated 3- to 8-membered heteromonocyclic group containing a sulfur atom, $R^2$ is hydroxy or lower alkanoyloxy, $R^4$ is carboxy, lower alkoxycarbonyl, phenyl(lower)alkoxycarbonyl or alkyl sulfonylcarbamoyl, $R^5$ is hydrogen, and Ar is $C_6$–$C_{10}$ aryl optionally substituted by a group selected from the group consisting of hydroxy, protected hydroxy, halogen, lower alkoxy, carboxy, protected carboxy, lower alkylenedioxy, carbamoyl(lower)alkyl, N- or N,N-di(lower)alkylcarbamoyl(lower)alkyl, carboxy(lower)alkyl, protected carboxy(lower)alkyl, $C_6$–$C_{10}$ ar(lower)alkyl, halo (lower) alkyl, halo (lower) alkoxy, lower alkanoyl, lower alkyl and $C_6$–$C_{10}$ aryl.

3. The compound of claim 2, wherein $R^1$ is lower alkyl, cyclo(lower)alkyl, or $C_6$–$C_{10}$ aryl optionally substituted by a group selected from the group consisting of lower alkoxy, carboxy, protected carboxy, lower alkylenedioxy and $C_6$–$C_{10}$ aryl, $R^3$ is lower alkyl, $C_6$–$C_{10}$ aryl, $C_6$–$C_{10}$ ar(lower)alkyl or heterocyclic(lower)alkyl optionally substituted by a group selected from the group consisting of protected carboxy, carbamoyl(lower)alkyl, N- or N,N- di(lower)alkylcarbamoyl(lower)alkyl, carboxy(lower)alkyl, protected carboxy(lower)alkyl, lower alkanoyl and lower alkyl, said heterocyclic group being unsaturated bicyclic 9- or 10-membered heterocyclic group containing 1 to 5 nitrogen atom(s), or unsaturated bicyclic 9- or 10-membered heterocyclic group containing 1 to 3 sulfur atom(s) or its S,S- dioxide, and Ar is $C_6$–$C_{10}$ aryl optionally substituted by a group selected from the group consisting of hydroxy, protected hydroxy, lower alkoxy, carboxy, protected carboxy and lower alkylenedioxy.

4. The compound of claim 3, wherein $R^1$ is lower alkyl, cyclo(lower)alkyl, or phenyl optionally substituted by a group selected from the group consisting of lower alkoxy, carboxy, lower alkoxycarbonyl, lower alkylenedioxy and phenyl, $R^2$ is hydroxy or lower alkanoyloxy, $R^3$ is lower alkyl, phenyl, phenyl(lower)alkyl, naphthyl(lower)alkyl, or heterocyclic(lower)alkyl optionally substituted by a group selected from the group consisting of lower alkoxycarbonyl, carbamoyl(lower)alkyl, N,N-di(lower)alkylcarbamoyl(lower)alkyl, carboxy(lower)alkyl, lower alkoxycarbonyl(lower)alkyl, phenyl(lower)alkoxycarbonyl(lower)alkyl, lower alkanoyl and lower alkyl, said heterocyclic group being indolyl or benzothienyl or its S,S-dioxide Ar is phenyl or naphthyl, each of which is optionally substituted by a group selected from the group consisting of hydroxy, phenyl(lower)alkoxy, lower alkoxy, carboxy, lower alkoxycarbonyl, phenyl(lower)alkoxycarbonyl and lower alkylenedioxy.

5. The compound of claim 4, wherein $R^1$ is lower alkyl, cyclo(lower)alkyl, or phenyl optionally substituted by a group selected from the group consisting of lower alkoxy, carboxy, lower alkoxycarbonyl, lower alkylenedioxy and phenyl, $R^3$ is lower alkyl, phenyl, phenyl(lower)alkyl, naphthyl(lower)alkyl, indolyl(lower)alkyl, optionally substituted by a group selected from the group consisting of lower alkoxycarbonyl, carbamoyl(lower)alkyl, N,N-di(lower)alkylcarbamoyl(lower)alkyl, carboxy(lower)alkyl, lower alkoxycarbonyl(lower)alkyl, phenyl(lower)alkoxycarbonyl(lower)alkyl, lower alkanoyl and lower alkyl, or benzothienyl(lower)alkyl or its S,S-dioxide, and Ar is phenyl optionally substituted by a group selected from the group consisting of hydroxy, phenyl(lower)alkoxy, lower alkoxy, carboxy, phenyl(lower)alkoxycarbonyl and lower alkylenedioxy, or naphthyl.

6. The compound of claim 5, wherein $R^3$ is optionally substituted indolyl-lower alkyl.

7. The compound of claim 6, wherein $R^3$ is indolyl-lower alkyl substituted with a lower alkyl group.

8. The compound of claim 7, which is N-[(2R,3R)-2-(3,4-methylenedioxyphenyl)-3-hydroxyheptanoyl]-L-Trp(Me)-OH.

9. The compound of claim 1, which is represented by the formula:

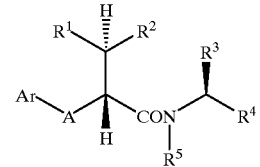

wherein Ar, A, $R^1$, $R^2$, $R^3$, $R^4$ and $R^5$ are as defined in claim 1.

10. A pharmaceutical composition which comprises a compound of claim 1, or a pharmaceutically acceptable salt thereof and a pharmaceutically acceptable carrier or excipient.

11. A method of treating an endothelin mediated disease, comprising administering an effective amount of the compound of claim 1 or a pharmaceutically acceptable salt thereof to a human being or an animal in need thereof.

* * * * *